United States Patent [19]
Davidsen et al.

[11] Patent Number: 5,985,911
[45] Date of Patent: Nov. 16, 1999

[54] C-TERMINAL KETONE INHIBITORS OF MATRIX METALLOPROTEINASES AND TNFα SECRETION

[75] Inventors: Steven K. Davidsen, Libertyville; Alan S. Florjancic, Lake Bluff; George S. Sheppard, Wilmette, all of Ill.; Jamie R. Giesler, Oak Creek, Wis.; Lianhong Xu, Libertyville; Yan Guo, Gurnee, both of Ill.; Michael L. Curtin, Kenosha, Wis.; Michael R. Michaelides, Gurnee, Ill.; Carol K. Wada, Grayslake, Ill.; James H. Holms, Gurnee, Ill.

[73] Assignee: Abbott Laboratories, Abbott Park, Ill.

[21] Appl. No.: 08/992,578

[22] Filed: Dec. 17, 1997

Related U.S. Application Data
[60] Provisional application No. 60/035,781, Jan. 7, 1997.

[51] Int. Cl.⁶ ............... C07C 259/10; A61K 31/165
[52] U.S. Cl. .............. 514/419; 514/575; 546/315; 548/200; 548/236; 548/492; 548/540; 549/72; 560/41; 562/444; 562/622; 562/623
[58] Field of Search .............. 518/309.7; 562/623, 562/444, 622; 514/419, 575; 546/315; 548/200, 236, 492, 540; 549/72; 560/41

[56] References Cited

U.S. PATENT DOCUMENTS

| | | |
|---|---|---|
| 4,996,358 | 2/1991 | Handa et al. . |
| 5,300,501 | 4/1994 | Porter . |
| 5,442,110 | 8/1995 | Isomura et al. . |

FOREIGN PATENT DOCUMENTS

| | | |
|---|---|---|
| 0489577 | 6/1992 | European Pat. Off. . |
| 0498665 | 8/1992 | European Pat. Off. . |
| 0575844 | 12/1993 | European Pat. Off. . |
| 9102716 | 3/1991 | WIPO . |
| 9213831 | 8/1992 | WIPO . |
| 9324449 | 12/1993 | WIPO . |
| 9402446 | 2/1994 | WIPO . |
| 9402447 | 2/1994 | WIPO . |
| 9410990 | 5/1994 | WIPO . |
| 9421612 | 9/1994 | WIPO . |
| 9422309 | 10/1994 | WIPO . |
| 9424140 | 10/1994 | WIPO . |
| 9425435 | 11/1994 | WIPO . |
| 9504735 | 2/1995 | WIPO . |
| 9506031 | 3/1995 | WIPO . |
| 9519956 | 7/1995 | WIPO . |
| 9519961 | 7/1995 | WIPO . |
| 9522966 | 8/1995 | WIPO . |
| 9523790 | 9/1995 | WIPO . |
| 9529892 | 11/1995 | WIPO . |
| 9532944 | 12/1995 | WIPO . |
| 9616027 | 5/1996 | WIPO . |
| 9616931 | 6/1996 | WIPO . |
| 9633161 | 10/1996 | WIPO . |
| 9718207 | 5/1997 | WIPO . |

OTHER PUBLICATIONS

Nature vol. 370 Aug. 18, 1994, pp. 555–557 "Processing of tumor necrosis factor–α precursor by metalloproteinases."
Nature vol. 370 Jul. 21, 1994, pp. 218–220 "Protection against a lethal dose of endotoxin be an inhibitor of tumor necrosis factor processing."
Nature vol. 370 Aug. 18, 1994, pp. 558–561 "Regulation of tumour necrosis factor–α processing by a metalloproteinase inhibitor."
F.B. Ibrahim, "Quantitative Determination of Oxaprozin and Several of its Related Compounds by high Performance Reversed–Phase Liquid Chromatography", *J. Liq. Chromatogr.*, vol. 18, No. 13, (1995), 2621–2633.
Goldsmith et al., "Identification of Impurities in a Novel Antiinflammatory Oxazole Derivative", *Proc. Soc. Anal. Chem.*, vol. 9, No. 2, (1972), pp.; 32–35.
K. Brown et al., Antiinflammatory 3–[4,5–bis (p–chlorophenyl) oxazol–2–yl] propionic acid and derivatives, Brit. 4 pp.,Addn. to. Brit. 1,206,403. (abstract).
F.W. Short et al., Synthesis of 5–aryl–2–oxazolepropionic Acids Analogs. Anti–inflammatory Agents, *J. Heterocycl. Chem.*, vol. 6, No. 5, (1969), pp. 707–712.

*Primary Examiner*—Robert Gerstl
*Attorney, Agent, or Firm*—Gregory W. Steele

[57] ABSTRACT

C-terminal compounds of formula

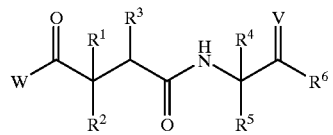

are potent inhibitors of matrix metalloproteinase and are useful in the treatment of diseases in which matrix metalloproteinase play a role. Also disclosed are matrix metalloproteinase inhibiting compositions and a method of inhibiting matrix metalloproteinase in a mammal.

13 Claims, No Drawings

C-TERMINAL KETONE INHIBITORS OF MATRIX METALLOPROTEINASES AND TNFα SECRETION

This application claims the benefit of U.S. Provisional Application No. 60/035,781, filed Jan. 7, 1997.

TECHNICAL FIELD

This invention relates to compounds having activity to inhibit matrix metalloproteinases and TNFα secretion, to pharmaceutical compositions comprising these compounds, and to a medical method of treatment. More particularly, this invention concerns C-terminal ketone compounds which inhibit matrix metalloproteinases and TNFα secretion, pharmaceutical compositions comprising these compounds and a method of inhibiting matrix metalloproteinases and TNFα secretion.

BACKGROUND OF THE INVENTION

The matrix metalloproteinases (MMP's) are a class of extracellular enzymes including collagenase, stromelysin, and gelatinase which are believed to be involved in the tissue destruction which accompanies a large number of disease states varying from arthritis to cancer.

Typical connective tissue cells are embedded within an extracellular matrix of high molecular weight proteins and glycoproteins. In healthy tissue, there is a continual and delicately-balanced series of processes which include cell division, matrix synthesis, and matrix degradation. In certain pathological conditions, an imbalance of these three processes can lead to improper tissue restructuring. For example, in arthritis, joint mobility can be lost when there is improper remodelling of load-bearing joint cartilage. In the case of cancer, lack of coordination of cell division and the two processes of matrix synthesis and degradation can lead to conversion of transformed cells to invasive phenotypes in which increased matrix turnover permits tumor cells to penetrate basement membranes surrounding capillaries leading to subsequent metastasis.

There has been heightened interest in discovering therapeutic agents which bind to and inhibit MMP's. The discovery of new therapeutic agents possessing this activity will lead to new drugs having a novel mechanism of action for combatting disease states involving tissue degenerative processes including, for example, rheumatoid arthritis, osteoarthritis, osteopenias such as osteoporosis, periodontitis, gingivitis, corneal, epidermal or gastric ulceration, and tumor growth and metastasis or invasion.

Tumor Necrosis Factor α (TNFα) is a potent proinflammatory mediator which has been implicated in inflammatory conditions including arthritis, asthma, septic shock, non-insulin dependent diabetes mellitus and inflammatory bowel disease. TNFα is originally expressed as a membrane-bound protein of about 26 kD, which is proteolytically cleaved to release a soluble 17 kD fragment (TNFα processing) which combines with two other secreted TNFα molecules to form a circulating 51 kD homotrimer. Recently, several MMP inhibitors were found to inhibit TNFα processing (see Mohler, et al., *Nature*, 1994, 370, 218; Gearing, et al., *Nature*, 1994, 370, 555; and McGeehan, et al., *Nature*, 1994, 370, 558), leading to the hypothesis that TNFα processing is caused by an as yet uncharacterized metalloproteinase residing in the plasma membrane of cells producing TNFα. Inhibitors of this metalloproteinase would therefore be useful as therapeutics to treat disease states involving TNFα secretion.

Transforming growth factor alpha (TGFα) is a potent mitogen which ellicites its biological activity by binding to cell surface receptors, in particular epidermal growth factor (EGF) receptor. It is known to promote angiogenesis and to stimulate epithelial cell migration and therefore has been implicated in a number of malignant disorders such as breast cancer and ovarian carcinoma. TGFα is produced by proteolytic cleavage of a 160 amino acid membrane bound precursor. Several cleavage sites have been identified including Ala38-Val39, similar to the cleavage site of proTNFα (Ala-76-Val77). This common cleavage site suggests that inhibitors of TNFα processing may also block the cleavage of proTGFα and therefore would be therapeutically useful in diseases mediated by TGFα.

SUMMARY OF THE INVENTION

The present invention provides a novel class of C-terminal ketone inhibitors of matrix metalloproteinases and/or TNFα secretion.

In its principle embodiment, the present invention provides a macrocyclic compound of formula I

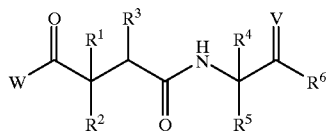

or a pharmaceutically acceptable salt, ester or prodrug thereof wherein

W is NHOH or —OH.

$R^1$ and $R^4$ are independently selected at each occurrence from hydrogen or alkyl of one to four carbon atoms.

V is or $NOR^1$.

$R^2$ is selected from the group consisting of
(a) hydrogen,
(b) hydroxy,
(c) alkoxy of one to six carbon atoms,
(d) alkyl of one to six carbon atoms,
(e) alkyl of one to six carbon atoms substituted with
 (1) halogen,
 (2) hydroxy,
 (3) alkoxy of one to six carbon atoms,
 (4) cycloalkyl of three to eight carbon atoms,
 (5) alkanoyloxy wherein the alkyl portion is of one to four carbon atoms,
 (6) pyridyl,
 (7) pyridyl substituted with alkyl of one to four carbon atoms,
 (8) phenoxy wherein the phenyl ring is unsubstituted or substituted with 1, 2 or 3 substituents independently selected from (8a) alkyl of one to four carbon atoms, (8b)hydroxy, (8c) alkoxy of one to four carbon atoms, (8d) halogen, (8e) haloalkyl of one to four carbon atoms, (8f) cyano, (8 g) cyanoalkyl, (8h) —$CO_2R^7$ wherein $R^7$ is hydrogen or alkyl of one to four carbon atoms, (8i) —$CONR^7R^8$ wherein $R^7$ is defined above and $R^8$ is selected from hydrogen, alkyl of one to four carbon atoms, alkanoyl of one to four carbon atoms, phenyl, and phenyl substituted with 1, 2, or 3 substituents independently selected from alkyl of one to four carbon atoms, hydroxy, alkoxy of one to four carbon atoms, halogen, haloalkyl of one to four carbon atoms, cyano, cyanoalkyl, —$CONR^9R^{10}$ wherein $R^9$ and $R^{10}$ are independently selected from hydrogen and alkyl of one to four carbon atoms, and —$CO_2R^9$,

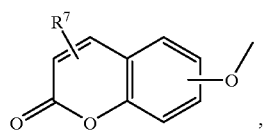

(10) —S(O)$_n$R$^{11}$ wherein n is 0, 1 or 2 and R$^{11}$ is selected from (10a) alkyl of one to six carbon atoms, (10b) phenyl, (10c) phenyl substituted with 1, 2 or 3 substituents independently selected from alkyl of one to four carbon atoms, hydroxy, alkoxy of one to four carbon atoms, halogen, haloalkyl of one to four carbon atoms, cyano, cyanoalkyl, —CO$_2$R$^7$, —CONR$^7$R$^8$, (10d) thienyl, (10e) thienyl substituted with alkyl of one to four carbon atoms, (10f) phenylalkyl wherein the alkyl portion is of one to four carbon atoms, (10 g) phenylalkyl wherein the alkyl portion is of one to four carbon atoms, and the phenyl ring is substituted with 1, 2 or 3 substituents independently selected from alkyl of one to four carbon atoms, hydroxy, alkoxy of one to four carbon atoms, halogen, haloalkyl of one to four carbon atoms, cyano, cyanoalkyl, —CO$_2$R$^7$, and —CONR$^7$R$^8$, (10h) thienyl alkyl wherein the alkyl portion is of one to four carbon atoms, and (10i) thienyl alkyl wherein the alkyl portion is of one to four carbon atoms and the thienyl ring is substituted with alkyl of one to four carbon atoms, and

(11) —NR$^{12}$R$^{13}$ wherein R$^{12}$ is hydrogen or alkyl of one to four carbon atoms and R$^{13}$ is selected from (11a) hydrogen, (11b) alkyl of one to four carbon atoms, (11c) —CO$_2$R$^{14}$ wherein R$^{14}$ is independently selected at each occurrence from (i) alkyl of one to four carbon atoms, (ii) haloalkyl of one to four carbon atoms, (iii) phenyl, (iv) phenyl substituted with 1, 2, or 3 substituents independently selected from alkyl of one to four carbon atoms, alkoxy of one to four carbon atoms, halogen, haloalkyl of one to four carbon atoms, nitro, cyano, cyanoalkyl, —SO$_2$NH$_2$, —CO$_2$R$^7$, and —CONR$^7$R$^8$, (v) phenylalkyl wherein the alkylene portion is of one to four carbon atoms, (vi) phenylalkyl wherein the alkylene portion is of one to four carbon atoms, and the phenyl ring is substituted with 1, 2, or 3 substituents independently selected from alkyl of one to four carbon atoms, alkoxy of one to four carbon atoms, halogen, haloalkyl of one to four carbon atoms, cyano, cyanoalkyl, —SO$_2$NH$_2$, —CO$_2$R$^7$, and —CONR$^7$R$^8$, (vii) heteroarylalkyl wherein the alkylene portion is of one to four carbon atoms, and the heteroaryl group is selected from furyl, pyridyl, thienyl, benzimidazolyl, imidazolyl, thiazolyl, and benzothiazolyl wherein the heteroaryl group is unsubstituted or substituted with alkyl of one to four carbon atoms, and (11d) —SO$_2$R$^{14}$, or R$^{12}$ and R$^{13}$, together with the N atoms to which they are attached define a heterocycle selected from morpholinyl, thiomorpholinyl, thiomorpholinyl sulfone, pyrrolidinyl, piperazinyl, piperidinyl, succinimidyl, maleimidyl, glutarimidyl, phthalimidyl, naphthalimidyl,

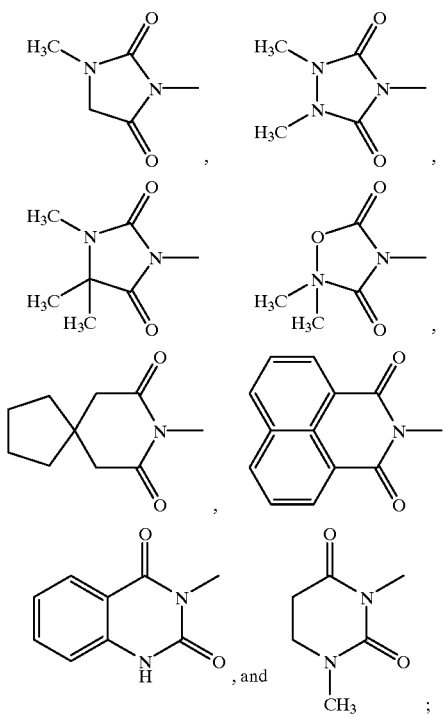

(f) alkenyl of two to six carbon atoms.
(g) alkenyl of two to six carbon atoms substituted with
(1) halogen,
(2) hydroxy,
(3) alkoxy of one to six carbon atoms,
(4) cycloalkyl of three to eight carbon atoms
(5) alkanoyloxy wherein the alkyl portion is of one to four carbon atoms,
(6) pyridyl,
(7) pyridyl substituted with alkyl of one to four carbon atoms,
(8) phenoxy wherein the phenyl ring is unsubstituted or substituted with 1, 2 or 3 substituents independently selected from (8a) alkyl of one to four carbon atoms, (8b) hydroxy, (8c) alkoxy of one to four carbon atoms, (8d) halogen, (8e) haloalkyl of one to four carbon atoms, (8f) cyano, (8 g) cyanoalkyl, (8h) —CO$_2$R$^7$, (8i) —CONR$^7$R$^8$, (8j) phenyl, and (8k) phenyl substituted with 1, 2, or 3 substituents independently selected from alkyl of one to four carbon atoms, hydroxy, alkoxy of one to four carbon atoms, halogen, haloalkyl of one to four carbon atoms, cyano, cyanoalkyl, —CO$_2$R$^9$, and —CONR$^9$R$^{10}$,

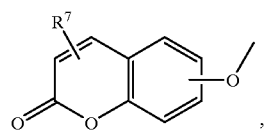

(10) —S(O)$_n$R$^{11}$ and
(11) —NR$^{12}$R$^{13}$;

R³ is selected from the group consisting of
(a) alkyl of one to ten carbon atoms,
(b) alkenyl of two to ten carbon atoms,
(c) cycloalkyl of three to eight carbon atoms,
(d) (cycloalkyl)alkyl wherein the cycloalkyl portion is of three to eight carbon atoms, and the alkylene portion is of one to six carbon atoms,
(e) cycloalkylene of five to eight carbon atoms,
(f) (cycloalkylene)alkyl wherein the cycloalkylene portion is of three to eight carbon atoms, and the alklene portion is of one to six carbon atoms,
(g) phenyl wherein the phenyl ring is unsubstituted or substituted with 1, 2 or 3 substituents independently selected from (g1) alkyl of one to four carbon atoms, (g2) alkoxy of one to four carbon atoms, (g3) halogen, (g4) haloalkyl of one to four carbon atoms, (g5) cyano, (g6) cyanoalkyl, (g7) —$CO_2R^7$, (g8) —$CO_2NR^7R^8$, (g9), alkoxyalkyloxy and (g10) phenyl substituted with 1, 2, or 3 substituents independently selected from alkyl of one to four carbon atoms, hydroxy, alkoxy of one to four carbon atoms, halogen, haloalkyl of one to four carbon atoms, cyano, cyanoalkyl, —$CO_2R^9$, and —$CONR^9R^{10}$,
(h) phenylalkyl wherein the alkylene portion is of one to six carbon atoms, and the phenyl ring is unsubstituted or substituted with 1, 2 or 3 substituents independently selected from (h1) alkyl of one to four carbon atoms, (h2) alkoxy of one to four carbon atoms, (h3) halogen, (h4) haloalkyl of one to four carbon atoms, (h5) cyano, (h6) cyanoalkyl, (h7) —$CO_2R^7$, (h8) —$CO_2NR^7R^8$, phenyl, and (h10) phenyl substituted with 1, 2, or 3 substituents independently selected from alkyl of one to four carbon atoms, alkoxy of one to four carbon atoms, halogen, haloalkyl of one to four carbon atoms, cyano, cyanoalkyl, —$CO_2R^7$ and —$CO_2NR^7R^8$,
(i) —$(CH_2)_m$—T—$(CH_2)_n$—$R^{15}$ wherein m and n are independently 0, 1, 2, 3 or 4, T is O or S, and $R^{15}$ is selected from the group consisting of (i1) alkyl of one to four carbon atoms, (i2) phenyl, and (i3) phenyl substituted with 1, 2, or 3 substituents selected from (i) alkyl of one to four carbon atoms, (ii) hydroxy, (iii) alkoxy of one to four carbon atoms, (iv) halogen, (v) haloalkyl of one to four carbon atoms, (vi) cyano, (vii) cyanoalkyl, (viii) —$CO_2R^7$, (ix) —$CONR^7R^8$, (x) phenyl, and (xi) phenyl substituted with 1, 2, or 3 substituents independently selected from alkyl of one to four carbon atoms, hydroxy, alkoxy of one to four carbon atoms, halogen, haloalkyl of one to four carbon atoms, cyano, cyanoalkyl, —$CO_2R^7$, and —$CONR^7R^8$, and
(j) fluorenylalkyl wherein the alkylene portion is of one to four carbon atoms, and R⁵ is selected from the group consisting of
(a) alkyl of one to six carbon atoms,
(b) alkyl of one to six carbon atoms substituted with (b1) cycloalkyl of three to eight carbon atoms, (b2) hydroxy, (b3) alkoxy, (b4) —$SR^7$, (b5) —$NR^7R^8$, (b6) —$CO_2R^7$, (b7) —$CONR^7R^8$, (b8) guanidyl, (b9) phenyl, (b10) phenyl substituted with 1, 2, or 3 substituents independently selected from alkyl of one to four carbon atoms, hydroxy, alkoxy of one to four carbon atoms, nitro, cyano, cyanoalkyl, carboxyalkyloxy, —$S(O)_nR^{16}$ wherein n is 0, 1 or 2 and $R^{16}$ is alkyl of one to four carbon atoms, —$SO_2NH_2$, —$CO_2R^7$, and —$CONR^7R^8$, and (b11) phenyl substituted with 1, 2, or 3 substituents independently selected from alkyl of one to four carbon atoms, hydroxy, alkoxy of one to four carbon atoms, halogen, and haloalkyl of one to four carbon atoms, (b10) naphthyl, (b11) naphthyl substituted with 1, 2, or 3 substituents independently selected from alkyl of one to four carbon atoms, hydroxy, alkoxy of one to four carbon atoms, halogen, haloalkyl of one to four carbon atoms, (b12) indolyl, (b13) indolyl substituted with alkyl of one to four carbon atoms, hydroxy, alkoxy of one to four carbon atoms, halogen, haloalkyl of one to four carbon atoms, —$SO_2R^{13}$, —$SO_2NH_2$, —$CO_2R^7$ and —$CONR^7R^8$, (b14) pyridyl, (b15) pyridyl substituted with alkyl of one to four carbon atoms, (b16) pyrazolyl, (b17) pyrazolyl substituted with alkyl of one to four carbon atoms, (b18) 5-oxadiazolyl, (b19) imidazolyl, and (b-20) imidazolyl substituted with alkyl of one to four carbon atoms,
(c) phenyl and
(d) phenyl substituted with 1, 2, or 3 substituents independently selected from alkyl of one to four carbon atoms, hydroxy, alkoxy of one to four carbon atoms, halogen, and haloalkyl of one to four carbon atoms, R⁶ is selected from the group consisting of
(a) alkyl of one to six carbon atoms,
(b) alkyl of one to six carbon atoms substituted with hydroxy, alkoxy, halogen, and —$CO_2R^{17}$ wherein $R^{17}$ is selected from hydrogen, alkyl of one to four carbon atoms and alkenyl of two to four carbon atoms,
(c) phenyl,
(d) phenyl substituted with 1, 2, or 3 substituents selected from (d₁) alkyl of one to four carbon atoms, (d2) halogen, (d3) hydroxy, (d4) hydroxyalkyl of one to four carbon atoms, (d5) haloalkyl of one to four carbon atoms, (d6) alkoxy of one to four carbon atoms, (d7) cyano, (d8) —$NR^7R^8$, (d9) —$SO_2NR^7R^8$, (d10) —$SO_2R^{16}$, (d11) —$CH_2NR^{18}R^{19}$, wherein $R^{18}$ and $R^{19}$ are independently selected at each occurrence from hydrogen and alkyl of one to four carbon atoms, or $R^{18}$ and $R^{19}$ together with the N atom to which they are attached define a a 5- or 6-membered heterocyclic ring selected from morpholinyl, thiomorpholinyl, thiompholinyl sulfone, pyrrolidinyl, piperazinyl, 3-ketopiperazinyl and piperidinyl, (d12) —$CONR^7R^8$, (d13) —$CO_2R^7$, and (d14) phenyl, wherein the phenyl ring may be substituted with 1, 2, or 3 substituents selected from alkyl of one to four carbon atoms, halogen, and haloalkyl of one to four carbon atoms,
(e) 1,3-benzodioxole,
(f) indolyl,
(g) indolyl substituted with (g1) alkyl of one to four carbon atoms, (g2) halogen, (g3) haloalkyl of one to four carbon atoms, (g4) alkoxy of one to four carbon atoms, (g5) —$SO_2NR^7R^8$, (g6) —$CO_2R^7$, (g7) alkylsulfonyl of one to four carbon atoms, and (g8) phenyl, wherein the phenyl ring may be substituted with 1, 2, or 3 substituents selected from alkyl of one to four carbon atoms, halogen, haloalkyl of one to four carbon atoms, and alkoxy of one to four carbon atoms,
(h) pyrrolyl,
(i) pyrrolyl substituted with alkyl of one to four carbon atom
(j) imidazolyl,
(k) imidazolyl substituted with alkyl of one to four carbon atoms,
(l) benzimidazolyl,
(m) benzimidazolyl substituted with 1, 2 or 3 substituents independently selected from alkyl of one to four carbon atoms, halogen and haloalkyl of one to four carbon atoms, provided that in (f)–(m) above, when the heterocycle is attached at a carbon atom, the N atom may bear a substituent selected from the group consisting of alkyl of one to six carbon atoms, —$CONR^7R^8$, —$SO_2NR^7R^8$ and —$SO_2R^{14}$, (n) pyridyl,
(o) pyridyl substituted with alkyl of one to four carbon atoms,
(p) thienyl,
(q) thienyl substituted with halogen, alkyl of one to four carbon atoms, and haloalkyl of one to four carbon atoms,
(r) thiazolyl,
(s) thiazolyl substituted with halogen, alkyl of one to four carbon atoms, and haloalkyl of one to four carbon atoms,
(t) oxazolyl,
(u) oxazolyl substituted with halogen, alkyl of one to four carbon atoms, and haloalkyl of one to four carbon atoms,
(v) furyl,
(w) furyl substituted with halogen, alkyl of one to four carbon atoms, and haloalkyl of one to four carbon atoms,
(x) benzofuryl,
(y) benzofuryl substituted with 1, 2, or 3 substituents selected from alkyl of one to four carbon atoms, halogen, and haloalkyl of one to four carbon atoms,
(z) benzothiazolyl, and
(aa) benzothiazolyl substituted with 1, 2, or 3 substituents selected from alkyl of one to four carbon atoms, halogen, and haloalkyl of one to four carbon atoms.

In another aspect, the present invention provides pharmaceutical compositions which comprise a therapeutically effective amount of compound of formula I in combination with a pharmaceutically acceptable carrier.

In yet another aspect, the present invention provides a method of inhibiting matrix metalloproteinases and/or TNFα secretion in a host mammal in need of such treatment comprising administering to a mammal in need of such treatment a therapeutically effective amount of a compound of formula I.

DETAILED DESCRIPTION

As used throughout this specification and the appended claims, the following terms have the meanings specified.

The term alkyl refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term alkylsulfonyl represents an alkyl group, as defined above, attached to the parent molecular group through a $SO_2$ group.

The term "alkanoyl" represents an alkyl group, as defined above, attached to the parent molecular moiety through a carbonyl group. Alkanoyl groups are exemplified by formyl, acetyl, propionyl, butanoyl and the like.

The terms alkoxy and alkoxyl denote an alkyl group, as defined above, attached to the parent molecular moiety through an oxygen atom. Representative alkoxy groups include methoxy, ethoxy, propoxy, butoxy, and the like.

The term "alkoxycarbonyl" represents an ester group; i.e. an alkoxy group, attached to the parent molecular moiety through a carbonyl group such as methoxycarbonyl, ethoxycarbonyl, and the like.

The term alkenyl as used herein refer to monovalent straight or branched chain groups of 2 to 6 carbon atoms containing a carbon-carbon double bond, derived from an alkene by the removal of one hydrogen atom and include, but are not limited to groups such as ethenyl, 1-propenyl, 2-propenyl, 2-methyl-1-propenyl, 1-butenyl, 2-butenyl and the like.

The term alkylene denotes a saturated divalent hydrocarbon group derived from a straight or branched chain saturated hydrocarbon containing by the removal of two hydrogen atoms, for example —$CH_2$—, —$CH_2CH_2$—, —$CH(CH_3)CH_2$— and the like.

The term alkenylene denotes a divalent group derived from a straight or branched chain hydrocarbon containing at least one carbon-carbon double bond. Examples of alkenylene include —CH═CH—, —$CH_2$CH═CH—, —C($CH_3$)═CH—, —$CH_2$CH═CH$CH_2$—, and the like.

The terms alkynylene refers to a divalent group derived by the removal of two hydrogen atoms from a straight or branched chain acyclic hydrocarbon group containing at least one carbon-carbon triple bond. Examples of alkynylene include —CH≡CH—, —CH≡C—$CH_2$—, —CH≡CH—CH($CH_3$)— and the like.

The term cycloalkyl as used herein refer to a monovalent saturated cyclic hydrocarbon group. Representative cycloalkyl groups include cyclopropyl, cyclobutyl, cyclopentyl, cyclohexyl, cycloheptyl, bicyclo[2.2.1]heptane and the like.

Cycloalkylene denotes a divalent radical derived from a cycloalkane by the removal of two hydrogen atoms.

The terms "(cycloalkyl)alkyl" and "(cycloalkenylene) alkyl" refer, respectively, to a cycloalkyl group or cycloalkenylene group as defined above attached to the parent molecular moiety through an alkylene group.

The term cyanoalkyl denotes an alkyl group, as defined above, substituted by a cyano group and includes, for example, cyanomethyl, cyanoethyl, cyanopropyl and the like.

The term haloalkyl denotes an alkyl group, as defined above, having one, two, or three halogen atoms attached thereto and is exemplified by such groups as chloromethyl, bromoethyl, trifluoromethyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "phenoxy" refers to a phenyl group attached to the parent molecular moiety through an oxygen atom.

By pharmaceutically acceptable salt is meant those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in *J. Pharmaceutical Sciences*, 1977, 66:1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like.

Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyates, acrylates and ethylsuccinates.

The term "pharmaceutically acceptable prodrugs" as used herein refers to those prodrugs of the compounds of the present invention which are, within the scope of sound medical judgement, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products followed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts.

PREFERRED EMBODIMENTS

Preferred compounds of the present invention have formula I wherein $R^6$ is defined therein; $R^1$ and $R^4$ are hydrogen; $R^2$ is selected from the group consisting of (a) hydrogen,
(b) hydroxy,
(c) alkoxy of one to six carbon atoms,
(d) alkyl of one to six carbon atoms,
(e) alkyl of one to six carbon atoms substituted with

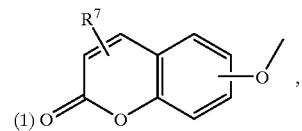

(2) —S(O)$_n$R$^{11}$ wherein n is 0, 1 or 2 and R$^{11}$ is selected from (2a) phenyl, (2b) phenyl substituted with 1, 2 or 3 substituents independently selected from alkyl of one to four carbon atoms, hydroxy, alkoxy of one to four carbon atoms, halogen, haloalkyl of one to four carbon atoms, cyano, cyanoalkyl, —CO$_2$R$^7$, and —CONR$^7$R$^8$, (2c) thienyl and (2d) thienyl substituted with alkyl of one to four carbon atoms and (3) —NR$^{12}$R$^{13}$ wherein R$^{12}$ and R$^{13}$ are independently selected from hydrogen and alkyl of one to four carbon atoms or R$^{12}$ and R$^{13}$, together with the N atoms to which they are attached define a

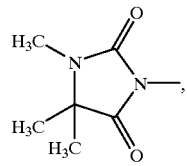

and
(f) alkenyl of two to six carbon atoms; R$^3$ is selected from the group consisting of
(a) alkyl of one to ten carbon atoms,
(b) cycloalkyl of three to eight carbon atoms, and
(c) phenylalkyl wherein the alkylene portion is of one to six carbon atoms, and the phenyl ring is unsubstituted or substituted with 1, 2 or 3 substituents independently selected from (c1) alkyl of one to four carbon atoms, (c2) alkoxy of one to four carbon atoms, (c3) halogen, (c4) haloalkyl of one to four carbon atoms, (c5) cyano, (c6) cyanoalkyl, (c7) —CO$_2$R$^7$, (c8) —CO$_2$NR$^7$R$^8$, (c9) phenyl, and (c10) phenyl substituted with 1, 2, or 3 substituents independently selected from alkyl of one to four carbon atoms, alkoxy of one to four carbon atoms, halogen, haloalkyl of one to four carbon atoms, cyano, cyanoalkyl, —CO$_2$R$^7$ and —CO$_2$NR$^7$R$^8$; and R$^5$ is selected from
(a) alkyl of one to six carbon atoms,
(b) alkyl of one to six carbon atoms substituted with (b1) cycloalkyl of three to eight carbon atoms, (b2) —CO$_2$R$^7$, (b3) —SR$^7$, (b4) phenyl, and (b5) phenyl substituted with 1, 2, or 3 substituents independently selected from alkyl of one to four carbon atoms, hydroxy, alkoxy of one to four carbon atoms, halogen, haloalkyl of one to four carbon atoms, nitro, cyano, cyanoalkyl, —S(O)$_n$R$^{16}$ wherein n is 0, 1 or 2 and R$^{16}$ is alkyl of one to four carbon atoms, —SO$_2$NH$_2$, —CO$_2$R$^7$, and —CONR$^7$R$^8$.

More preferred compounds have the structure immediately above wherein W is —NHOH and V is O.

Still more preferred compounds have the structure immediately above wherein R$^2$ is selected from the group consisting of hydrogen, hydroxy and alkenyl of two to six carbon atoms; R$^3$ is selected from the group consisting of isobutyl, cyclohexyl, 3-phenylpropyl, 3-(4-tolyl)propyl and biphenyloxy; R$^5$ is selected from the group consisting of alkyl of one to six carbon atoms, and alkyl of one to six carbon atoms substituted with cycloalkyl of three to eight carbon atoms, carboxy, phenyl, and hydroxyphenyl; and $R^6$ is selected from
(a) alkyl of one to six carbon atoms,
(b) alkyl of one to six carbon atoms substituted with —$CO_2R^{17}$,
(c) phenyl,
(d) phenyl substituted with 1, 2, or 3 substituents selected from alkyl of one to four carbon atoms, halogen, hydroxy, hydroxyalkyl of one to four carbon atoms, haloalkyl of one to four carbon atoms, alkoxy of one to four carbon atoms, —$NR^7R^8$, cyano, —$SO_2NR^7R^8$, —$SO_2R^{16}$, —$CH_2NR^{18}R^{19}$, —$CONR^7R^8$ and —$CO_2R^7$,
(e) indolyl,
(f) indolyl substituted with alkyl of one to four carbon atoms, halogen, haloalkyl of one to four carbon atoms, alkoxy of one to four carbon atoms and phenyl, wherein the phenyl ring may be substituted with 1, 2, or 3 substituents selected from alkyl of one to four carbon atoms, halogen, haloalkyl of one to four carbon atoms, and alkoxy of one to four carbon atoms,
(g) pyrrolyl,
(h) pyrrolyl substituted with alkyl of one to four carbon atoms,
(i) benzimidazolyl,
(j) benzimidazolyl substituted with 1, 2 or 3 substituents independently selected from alkyl of one to four carbon atoms, halogen and haloalkyl of one to four carbon atoms, provided that in (e)–(j) above, when the heterocycle is attached at a carbon atom, the N atom may bear a substituent selected from the group consisting of alkyl of one to six carbon atoms, —$CONR^7R^8$ and —$SO_2NR^7R^8$,
(k) thienyl,
(l) thienyl substituted with halogen, alkyl of one to four carbon atoms, and haloalkyl of one to four carbon atoms,
(m) thiazolyl,
(n) thiazolyl substituted with halogen, alkyl of one to four carbon atoms, and haloalkyl of one to four carbon atoms,
(o) oxazolyl and
(p) oxazolyl substituted with halogen, alkyl of one to four carbon atoms, and haloalkyl of one to four carbon atoms.

Still yet more preferred compounds have the structure immediately above wherein $R^6$ is selected from the group consisting of
(a) phenyl,
(b) phenyl substituted with 1, 2, or 3 substituents selected from alkyl of one to four carbon atoms, halogen, hydroxy, hydroxyalkyl of one to four carbon atoms, haloalkyl of one to four carbon atoms, alkoxy of one to four carbon atoms, —$NR^7R^8$, cyano, —$SO_2NR^7R^8$, —$SO_2R^{16}$, —$CH_2NR^{18}R^{19}$, —$CONR^7R^8$ and —$CO_2R^7$,
(c) indolyl,
(d) indolyl substituted with alkyl of one to four carbon atoms, halogen, haloalkyl of one to four carbon atoms, alkoxy of one to four carbon atoms and phenyl, wherein the phenyl ring may be substituted with 1, 2, or 3 substituents selected from alkyl of one to four carbon atoms, halogen, haloalkyl of one to four carbon atoms, and alkoxy of one to four carbon atoms,
(e) pyrrolyl,
(f) pyrrolyl substituted with alkyl of one to four carbon atoms,
(g) benzimidazolyl,
(h) benzimidazolyl substituted with 1, 2 or 3 substituents independently selected from alkyl of one to four carbon atoms, halogen and haloalkyl of one to four carbon atoms, provided that in (c)–(h) above, when the heterocycle is attached at a carbon atom, the N atom may bear a substituent selected from the group consisting of alkyl of one to six carbon atoms, —$CONR^{15}R^{16}$ and —$SO_2NR^{15}R^{16}$,
(i) thienyl,
(j) thienyl substituted with halogen, alkyl of one to four carbon atoms, and haloalkyl of one to four carbon atoms,
(k) thiazolyl,
(l) thiazolyl substituted with halogen, alkyl of one to four carbon atoms, and haloalkyl of one to four carbon atoms,
(m) oxazolyl and
(n) oxazolyl substituted with halogen, alkyl of one to four carbon atoms, and haloalkyl of one to four carbon atoms.

The most preferred compounds of this invention have the structure immediately above wherein $R^6$ is selected from the group consisting of phenyl and phenyl substituted with 1, 2, or 3 substituents selected from alkyl of one to four carbon atoms, halogen, hydroxy, hydroxyalkyl of one to four carbon atoms, haloalkyl of one to four carbon atoms, alkoxy of one to four carbon atoms, —$NR^7R^8$, cyano, —$SO_2NR^7R^8$, —$SO_2R^{16}$, —$CH_2NR^{18}R^{19}$, —$CONR^7R^8$, —$CO_2R^7$, and phenyl, wherein the phenyl ring may be substituted with 1, 2, or 3 substituents selected from alkyl of one to four carbon atoms, halogen, and haloalkyl of one to four carbon atoms.

DETERMINATION OF STROMELYSIN INHIBITION

The efficacy of the compounds of this invention as matrix metalloproteinase inhibitors was determined by measuring the inhibition of stromelysin. The inhibition of stromelysin by the compounds of this invention was determined as follows: Recombinant truncated stromelysin (human sequence) produced in *E. coli* was prepared by expression and purification of the protein as described by Ye et al., *Biochemistry*, 1992, 31, 11231–11235. The enzyme was assayed by its cleavage of the thiopeptide ester substrate Ac-Pro-Leu-Gly-[2-mercapto-4-methyl-pentanoyl]-Leu-Gly-OEt described by Weingarten and Feder, *Anal. Biochem.*, 1985, 147, 437–440 (1985), as a substrate of vertebrate collagenase. The reported conditions were modified to allow assays to be carried out in a microtiter plate. Upon hydrolysis of the thioester bond, the released thiol group reacts rapidly with 5,5'-dithio-bis(2-nitrobenzoic acid) (DTNB), producing a yellow color which is measured by a microtiter plate reader set at 405 nm. The rates of cleavage of the substrate by stromelysin in the presence or absence of inhibitors are measured in a 30 min assay at ambient temperature. Solutions of the compounds in DMSO are prepared, and these are diluted at various concentrations into the assay buffer (50 mM MES/NaOH pH 6.5 with 10 mM $CaCl_2$ and 0.2% Pluronic F-68), which is also used for dilution of the enzyme and substrate. The potency of the compounds [$IC_{50}$] are calculated from the inhibition/inhibitor concentration data. The compounds of this invention inhibit stromelysin as shown by the data for representative examples in Table 1.

TABLE 1

Inhibitory Potencies against Stromelysin of Representative Compounds

| Example | $IC_{50}$ (nM) |
|---|---|
| 1 | 36 |
| 1G | 2.3 |
| 1H | 88 |
| 2 | 3.6 |
| 5 | 5.6 |

TABLE 1-continued

Inhibitory Potencies against Stromelysin of Representative Compounds

| Example | $IC_{50}$ (nM) |
|---|---|
| 6 | 12 |
| 7 | 8.0 |
| 8 | 8.6 |
| 9 | 1.2 |
| 10 | 7100 |
| 11 | 93000 |
| 12 | 7.8 |
| 13 | 99 |
| 14 | 1.2 |
| 15 | 27 |
| 16 | 36 |
| 17 | 16 |
| 18 | 4.5 |
| 19 | 1.5 |
| 20 | 7.3 |
| 21 | 1.7 |
| 22 | 10 |
| 23 | 6.6 |
| 24 | 3.2 |
| 25 | 1.8 |
| 26 | 220 |
| 27 | 2.7 |
| 28 | 320 |
| 30 | 320 |
| 31 | 740 |
| 33 | 110 |

PHARMACEUTICAL COMPOSITIONS

The present invention provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parental" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

PREPARATION OF COMPOUNDS OF THIS INVENTION

The compounds of this invention may be prepared by a variety of synthetic routes. Representative procedures are outlined in the following Schemes 1–3.

Abbreviations which have been used in the descriptions of the schemes and the examples that follow are: THF for tetrahydrofuran; DMF for N,N-dimethylformamide; ETOAc for ethyl acetate; $Et_2O$ for diethyl ether, IPA for isopropanol; ETOH for ethanol; MeOH for methanol; AcOH for acetic acid; HOBT for 1-hydroxybenzotriazole hydrate; EDC for 1-(3-dimethylaminopropyl)-3-ethylcarbodiimide hydrochloride; NMM for N-methylmorpholine; $Bu_3P$ for tributylphosphine; ADDP for 1,1'-(azodicarbonyl)dipiperidine; and DMPU for 1,3-dimethyl-3,4,5,6-tetrahydro-2(1H)-pyrimidinone.

The preparation of representative compounds of the invention, wherein $R^1$–$R^6$ and W are defined above, is outlined in Scheme 1. Coupling of succinic acid derivative 1 with keto amine 2 in the presence of an tertiary amine base, hydroxybenzotriazole (HOBt), and a suitable coupling agent such as 1-(3-dimethylaminopropyl)-3-ethylcarbodiimide hydrochloride (EDCI.HCl) gives 3. Conversion of 3 to the corresponding carboxylic acid 4 is accomplished by acidic removal of the tert-butyl ester using, for example, trifluoroacetic acid or hydrogen chloride in dioxane. Treatment of this acid with hydroxylamine or a hydroxylamine equivalent such as O-tert-butyldimethylsilylhydroxylaminne in the presence of a suitable coupling agent such as EDCI.HCl gives hydroxamate 5. O-Benzylhydroxylamine can also be employed in this coupling reaction. The resulting O-benzylhydroxamate can then be treated with hydrogen and a palladium catalyst such as 10% palladium on carbon to produce hydroxamate 5.

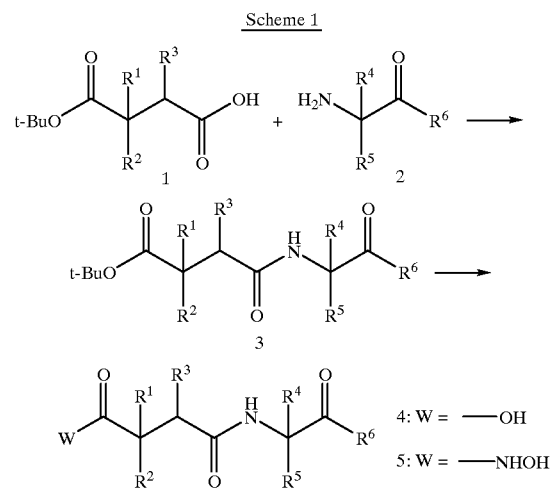

Scheme 1

Preparation of keto amine 2 is accomplished as shown in Scheme 2. Conversion of the protected amino acid 6 to the methyl ester or N,O-dimethylamide is accomplished by known methods. Reaction of 7 with $R^6MgX$ wherein X is Br, Cl or I, or $R^6Li$ generates ketone 8. Acidic removal of the tert-butyl protecting groups gives amino ketone 2. Alternatively, 6 can be treated with a carbon anion such as phenyllithium which gives 8 directly.

Scheme 2

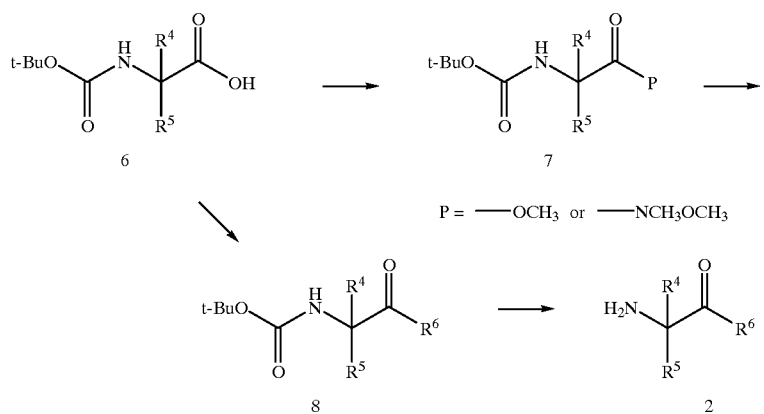

P = —OCH₃ or —NCH₃OCH₃

The preparation of the succinic acid derivative 1 is shown in Scheme 3. Treatment of oxazolidinone 9 with a suitable base such as lithium diisopropylamide followed by addition of tert-butyl bromoacetate and basic hydrolysis gives carboxylic acid 10. This acid is treated with at least two equivalents of a strong base such as lithium diisopropylamide followed by an alkylating agent $R^2X$ wherein X is Br, Cl or I. The resulting dialkyl succinate 11 is again treated with a strong base such as lithium diisopropylamide followed by either methanol ($R^1$=H) or an alkyl halide ($R^1$= alkyl) such as methyl iodide to give substituted succinate 1.

The foregoing may be better understood by reference to the following examples which are presented for illustration and are not intended to limit the scope of the invention as defined in the appended claims.

PREPARATION OF SUCCINATE ESTER 1

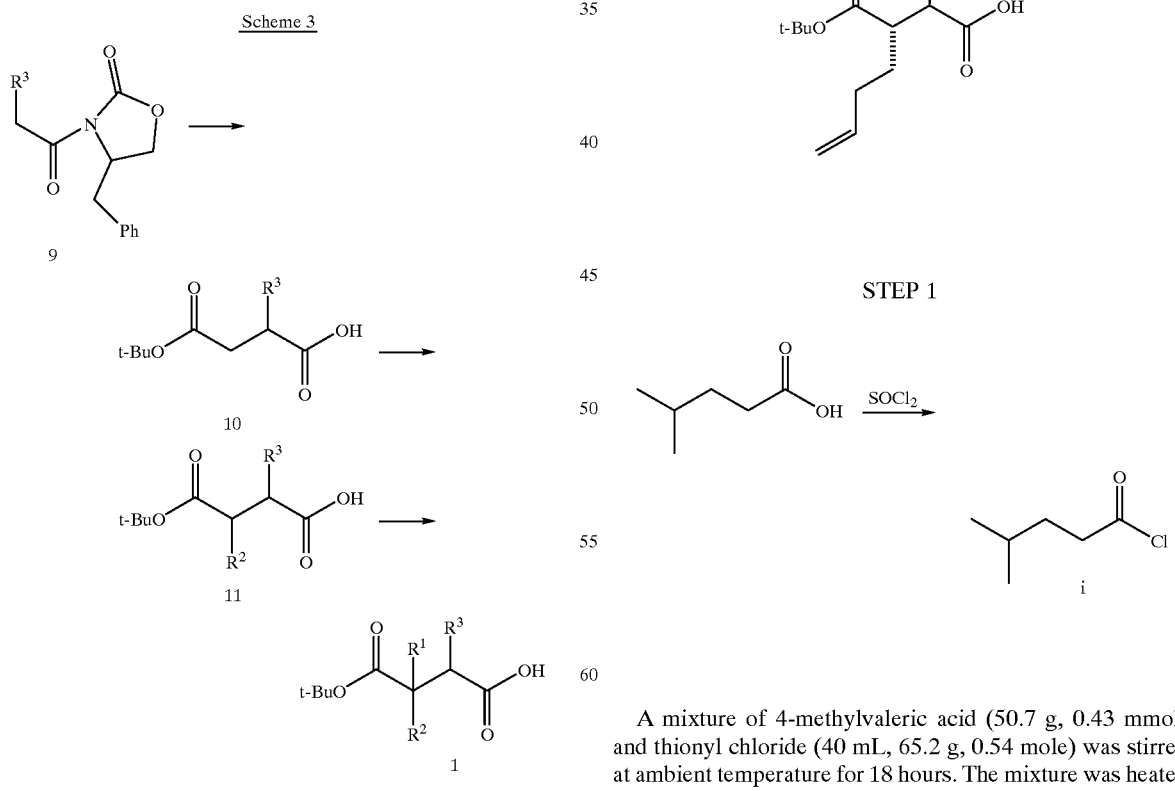

STEP 1

A mixture of 4-methylvaleric acid (50.7 g, 0.43 mmol) and thionyl chloride (40 mL, 65.2 g, 0.54 mole) was stirred at ambient temperature for 18 hours. The mixture was heated to distill the excess reagent through a 10 cm Vigreux column. The acid chloride was then distilled to give i (48.43 g, 84%), bp 135–138° C.

STEP 2

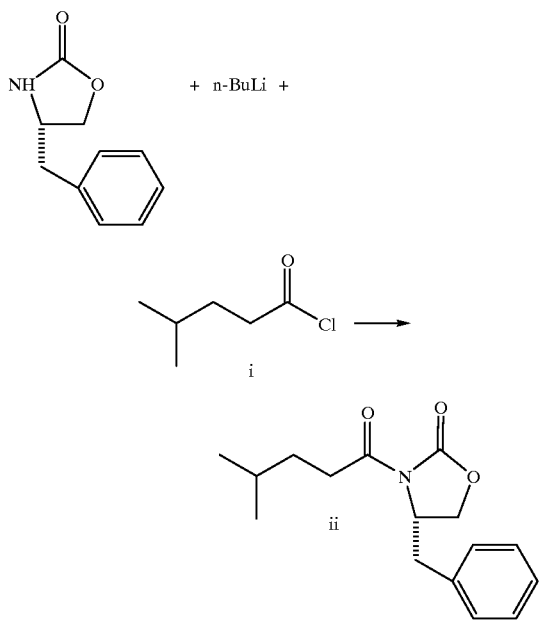

To a –78° C. solution of 4S-benzyl-2-oxazolidinone (62.2 g, 0.35 mole) in THF (600 mL) was added n-butyllithium (140 mL, 2.5 M in hexane) over 1 hour. After 30 minutes i (0.359 mole) was added over 10 minutes during which time the temperature rose to –60° C. After 1 hour the bath was removed and the reaction mixture was warmed to 0° C. The reaction was quenched with saturated ammonium chloride, the mixture was allowed to settle, and the supernatant was decanted and concentrated. The combined residues were partitioned between water and ethyl acetate. The organic layer was washed with water, 1M sodium bicarbonate, water and brine, dried over sodium sulfate, filtered and concentrated. The residue was distilled discarding a small forerun to give ii (92.9 g, 96%), bp 154–156° C./0.15 mm.

STEP 3

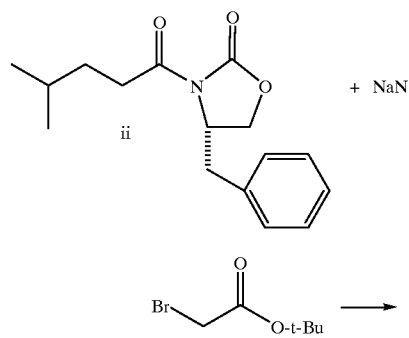

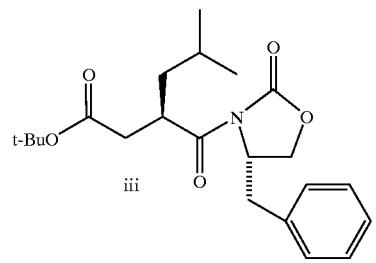

To a mechanically-stirred –78° C. solution of ii (92.9 g, 0.337 mole) in THF (1 L) was added sodium bis(trimethylsilyl)amide (375 mL, 1M in THF) over 40 minutes. The reaction mixture was stirred for 30 minutes and t-butyl bromoacetate (55 mL, 72.6 g, 0.372 mole) was added over 30 minutes. The reaction mixture was stirred for 30 minutes and then the cold bath was removed and the mixture was warmed to 0° C. The reaction was quenched with saturated ammonium chloride. After mixing well, the mixture was allowed to settle and the supernatant was decanted, concentrated, and recombined with the residue. This mixture was partitioned between water and ethyl acetate. The organic layer was washed with water, 1 M sodium bicarbonate, water and brine, dried over sodium sulfate and concentrated by distillation to about 250 mL. After dilution with 750 mL hexane and cooling in an ice bath the resulting crystals were collected and washed with hexane to provide iii (104.6 g) mp 101–102° C. The mother liquors were concentrated and the residue was purified by chromatography on silica gel (5–10% ethyl acetate-hexane) and the product fraction crystallized to yield 7.6 g more for a total of 112.2 g (85%).

STEP 4

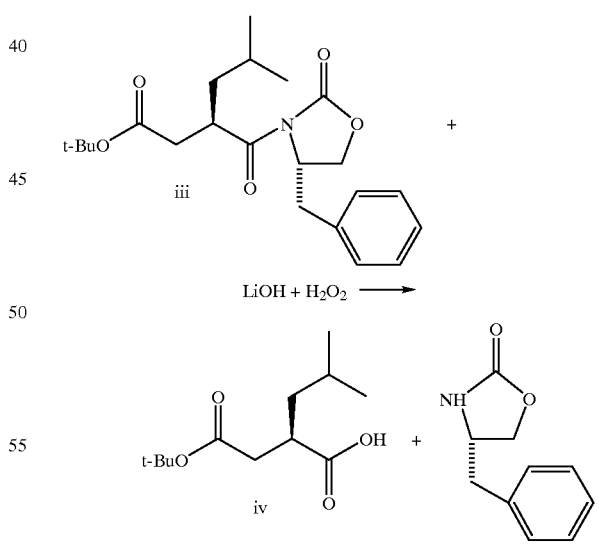

To a 0° C. solution of iii (112.2 g, 0.288 mole) in THF (1.2 L) was added water (100 mL) and 30% hydrogen peroxide (110 mL, 36.6 g, 1.08 mole). A solution of lithium hydroxide monohydrate (17.8 g, 0.424 mole) in water (400 mL) was added in portions over 25 minutes and the resulting solution was stirred for 1 hour. The mixture was concentrated under a slow nitrogen stream to about 800 mL. After seeding with the chiral oxazolidinone the mixture was chilled and filtered removing a portion of the auxiliary which was washed well with water. The filtrate was extracted with dichloromethane (3x) to remove the balance of the chiral oxazolidinone. The combined organic extracts were washed with aqueous 0.5 N sodium hydroxide. The base layers were acidified with 1M sulfuric acid to pH 3 and extracted with ethyl acetate. After washing with water and brine, drying over sodium sulfate, and evaporation of solvents the residue amounted to 64.9 g (98%) of R-2-(i-butyl)-succinic acid-4-t-butyl ester.

STEP 5

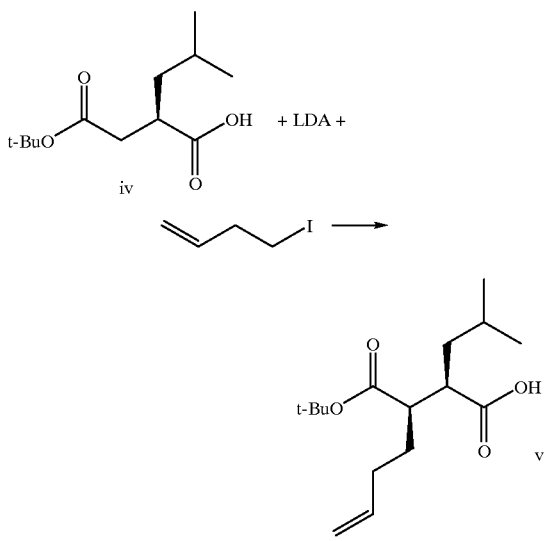

To a −78° C. solution of lithium diisopropylamide, prepared by the addition of n-butyllithium (11.4 ml, 28.4 mmol, 2.5M in hexanes) to a solution of diisopropylamine (3.7 ml, 28.4 mmol) in 60 ml THF at −78° C., was added a solution of iv (2.7 g, 11.8 mmol) in THF (20 mL) at −78° C. by cannula in a stream. The resulting clear, yellow solution was stirred at −78° C. for 1 hour and then butenyl iodide (2.58 g, 14.2 mmol) was added by syringe. This mixture was allowed to warm to ambient temperature and stir overnight. The reaction mixture was poured into 1:1 ether-water and the separated aqueous layer was extracted with ether (2x). The combined organic layers were washed with aq 1M NaHSO$_4$ and brine, dried with MgSO$_4$, filtered and concentrated. Flash chromatography (2%–5% isopropanol-hexane) gave epimeric succinates v (2.30 g, >9:1 syn/anti) as a clear liquid.

STEP 6

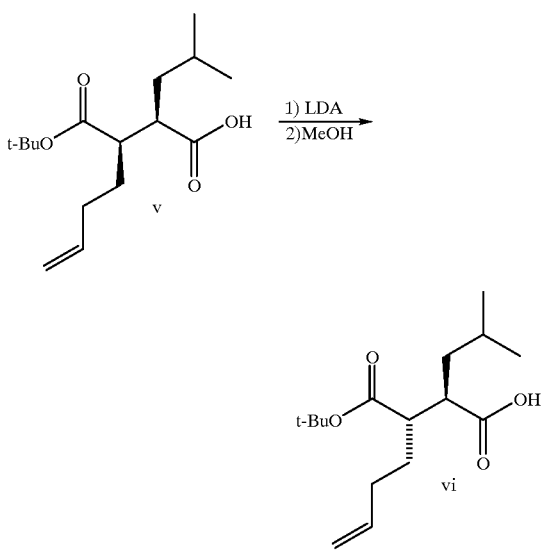

To a −78° C. solution of lithium diisopropylamide, prepared by the addition of n-butyllithium (7.8 ml, 19.5 mmol, 2.5M in hexanes) to a solution of diisopropylamine (2.6 ml, 19.5 mmol) in 30 ml THF at −78° C., was added a solution of epimeric isobutyl succinate v (2.3 g, 8.1 mmol) in THF (10 mL) at −78° C. by cannula in a stream. The resulting clear, yellow solution was stirred at −78° C. for 1 hour, warmed to 0° C. and recooled to −78° C. Methanol (1 ml) was added and the solution was warmed to 0° C. The reaction mixture was poured into 1:1 ether-water and the separated aqueous layer was extracted with ether (2x). The combined organic layers were washed with aq 1M NaHSO$_4$ and brine, dried with MgSO$_4$, filtered and concentrated to give an epimeric mixture (2:1 anti/syn) of succinates vi which could be separated by flash chromatography (10–50% ethyl acetate-hexanes).

PREPARATION OF SUCCINATE ESTER 2

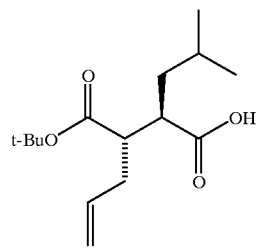

The desired compound was prepared according to the method used to prepare succinate ester 1, except substituting allyl bromide for 4-bromo-1-butene.

PREPARATION OF SUCCINATE ESTER 3

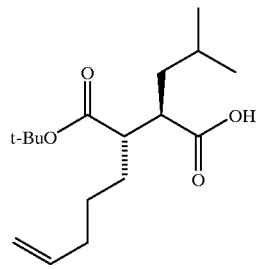

The desired compound was prepared according to the method used to prepare succinate ester 1, except substituting 5-bromo-1-pentene for 4-bromo-1-butene.

PREPARATION OF SUCCINATE ESTER 4

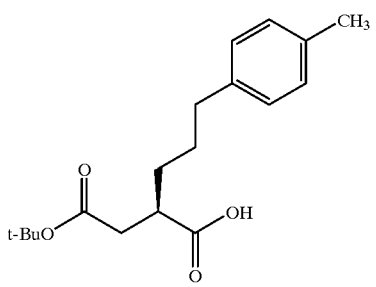

Step 1

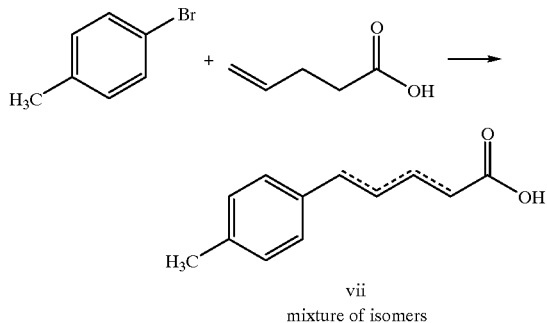

mixture of isomers

A mixture under nitrogen of 4-bromotoluene (36.9 mL, 51.3 g, 0.3 mole), 4-pentenoic acid (30.6 mL, 30.0 g, 0.3 mole), acetonitrile (500 mL), triethylamine (126 mL, 91.5 g, 0.90 mole), palladium acetate (1.35 g, 6 mmole) and tri-(o-tolyl)phosphine (4.65 g, 15 mmole) was heated slowly to a gentle reflux. (A mild exotherm was observed as reflux begins.) After 18 hours at reflux, the mixture was cooled in an ice bath and the solid was removed by filtration and rinsed well with ethyl acetate. The filtrate was concentrated to a small volume and the residue was partitioned between aqueous 1 M sodium carbonate and ether. The aqueous phase was extracted with ether. The combined ether layers were extracted with aqueous 1 M sodium carbonate. The basic solution was treated with charcoal and filtered. The filtrate was acidified with 3 M hydrochloric acid. After cooling in an ice bath, the soft solid was filtered, washed with ice water, and dried over sodium hydroxide to give vii (45 g) as a mixture of isomers which was used without further purification.

STEP 2

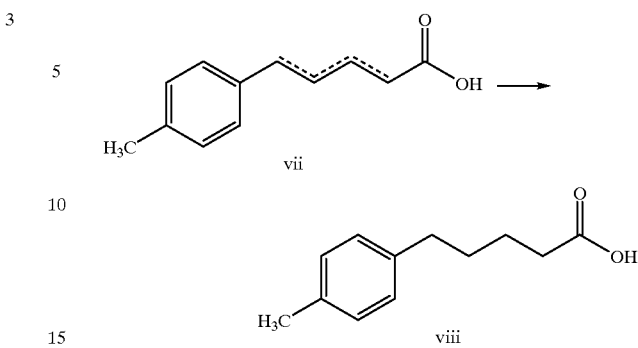

The mixture of isomers vii was hydrogenated in 600 mL THF over 9 g of 10% palladium on carbon at 4 atmospheres of hydrogen for 18 hours. After filtration and concentration of the solution, the residue was crystallized from hexane to yield 5-(4-tolyl)pentanoic acid (viii, 33 g, mp 77–78° C.).

STEP 3

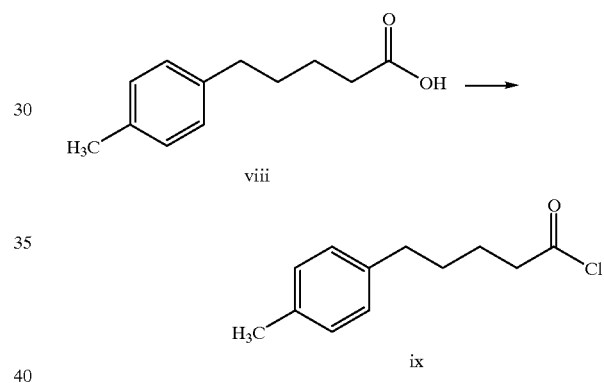

A mixture of 30b (11.02 g, 57 mmole) and 12 mL thionyl chloride was stirred at 24° C. for 18 hours and then heated to distill most of the excess thionyl chloride. Short path distillation gave 11.74 g (97%) of 5-(4-tolyl)pentanoyl chloride (30c, bp~110° C. at 0.35 mm).

STEP 4

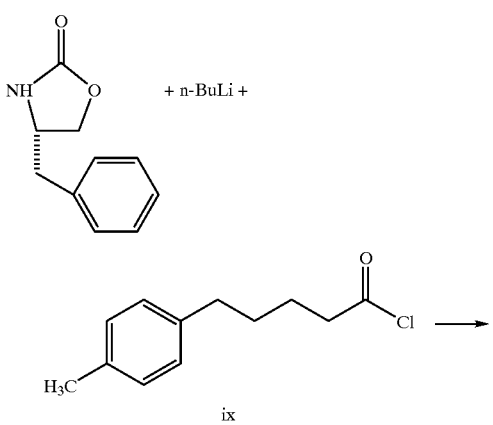

25
-continued

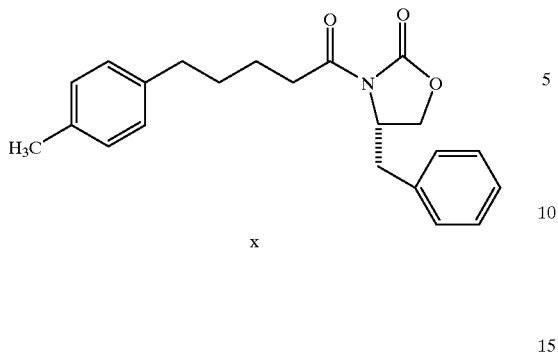

x

To a -78° C. solution of 4S-benzyl-2-oxazolidinone (10.36 g, 58 mmole) in THF (150 mL) was added n-butyllithium (23.5 mL 2.5 M) over 25 minutes. After 30 minutes, 30c (55.7 mmole) was added quickly, during which time the reaction temperature rose to -45° C. The reaction mixture was warmed to 0° C. and the reaction was quenched with saturated aqueous ammonium chloride. The mixture was allowed to settle and the supernatant was decanted and concentrated. The residue was partitioned between water and ethyl acetate. The organic layer was washed with water, aqueous 1M sodium bicarbonate, water and brine. After drying over sodium sulfate the solution was concentrated and the residue was chromatographed (10–20% ethyl acetate-hexane) to give 30d (17.83 g, 89%).

STEP 5

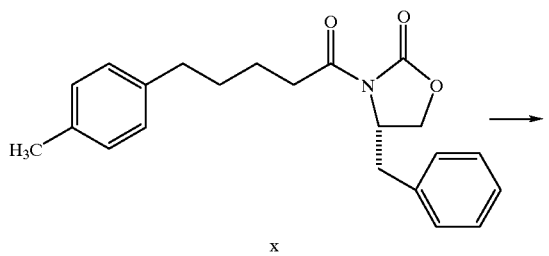

The desired compound was prepared using Step 4 of the preparation of succinate ester 1, except substituting x for iii.

26
PREPARATION OF SUCCINATE ESTER 5

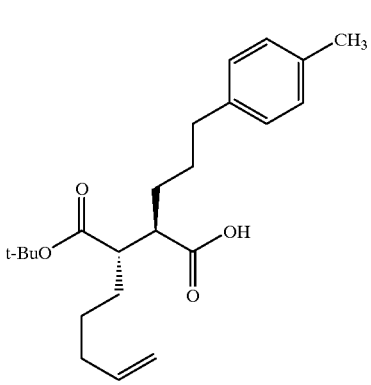

The desired compound was prepared using steps 5 and 6 of the preparation of succinate ester 1, except substituting succinate ester 4 for iv.

PREPARATION OF SUCCINATE ESTER 6

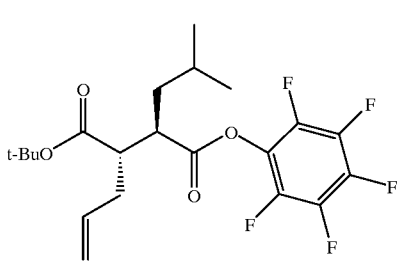

To a cold (0°) solution of succinate ester 2 (0.79 g, 3 mmol) in 10 mL methylene chloride was added pentaflurophenol (0.65 g, 3.5 mmol) and EDCI (0.69 g, 3.5 mmol). The resulting solution was stirred for 16 hours while warming to ambient temperature. The reaction mixture was quenched with 2N Na$_2$CO$_3$. The organic layer was washed with 2N HCl and brine, dried (sodium sulfate) and concentrated to give succinate ester 8 (0.8 g) as a crude yellow oil, which was used without further purification.

PREPARATION OF SUCCINATE ESTER 7

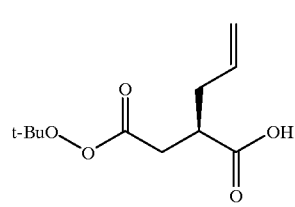

The desired compound was prepared using steps 1–4 of the preparation of succinate ester 1, except substituting 4-pentenoic acid for 4-methyl valeric acid in step 1.

PREPARATION OF SUCCINATE ESTER 8

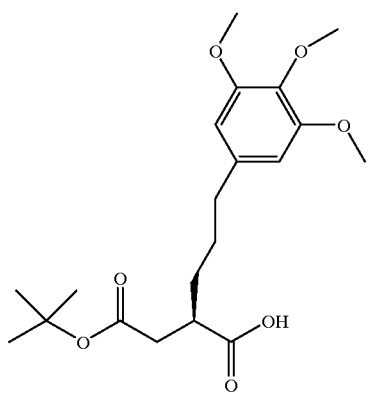
8

The desired compound was prepared from the succinate ester 7 using the Suzuki coupling conditions described in Example 41B.

PREPARATION OF SUCCINATE ESTER 9

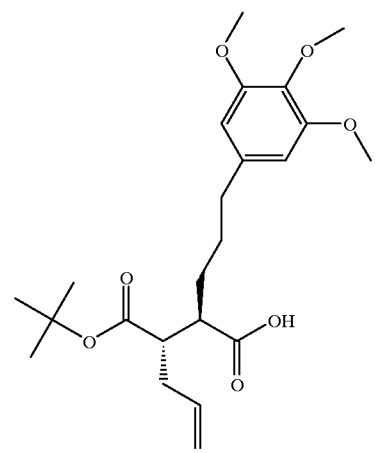
9

The desired compound was prepared from succinate ester 8, using step 5 of the preparation of succinate ester 1, except substituting allyl iodide for butenyl iodide.

PREPARATION OF SUCCINATE ESTER 10

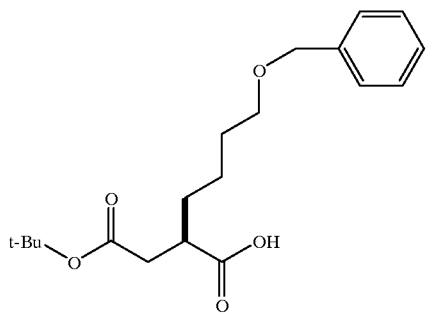
10

The desired compound was prepared using steps 1–4 of the preparation of succinate ester 1 except substituting 6-benzyloxyhexanoic acid for 4-methyl valeric acid in step 1.

PREPARATION OF SUCCINATE ESTER 11

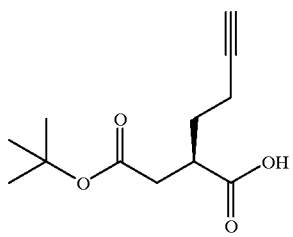
11

STEP 1

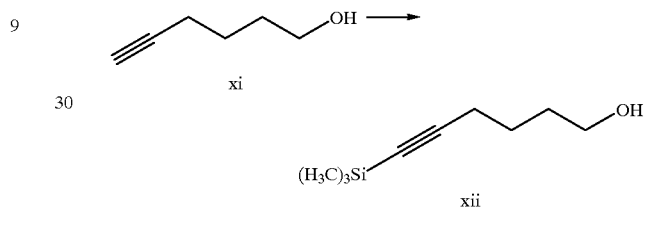

Prepared as described for 4-(trimethylsilyl)-3-butyn-1-ol in Organic Syntheses 1993, Volume VIII, p. 609.

$^1$H NMR (300 MHz, CDCl$_3$) δ3.68 (t, 2H), 2.27 (t, 2H), 1.68–1.62 (m, 4H), 0.14 (s,9H).

STEP 2

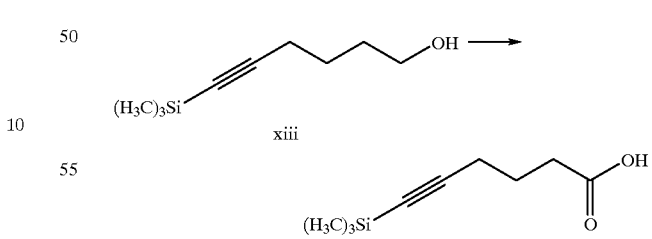

Prepared as described in Tetrahedron Letters 1979, p. 399.

$^1$H NMR (300 MHz, CDCl$_3$) δ2.50 (t, 2H), 2.32 (t, 2H), 1.84 (t, 2H), 0.14 (s, 9H).

STEP 3

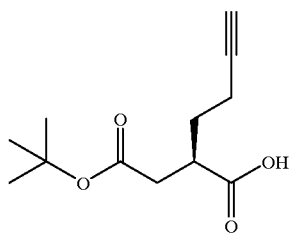

The desired compound was prepared using steps 1–4 of the preparation of succinate ester 1 except substituting 6-(trimethylsilyl)-5-hexynoic acid for 4-methyl valeric acid in step 1.

$^1$H NMR (300 MHz, CDCl$_3$) δ3.03–2.94 (m, 1H), 2.64 (dd, 1H), 2.47 (dd, 1H), 2.31 (td, 2H), 2.00 (t, 1H), 1.99–1.90 (m, 1H), 1.81–1.69 (m, 1H), 1.45 (s, 9H).

MS (DCI/NH$_3$) m/e 227 (M+1)$^+$.

EXAMPLE 1

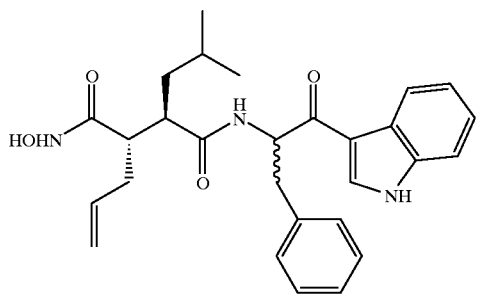

EXAMPLE 1A

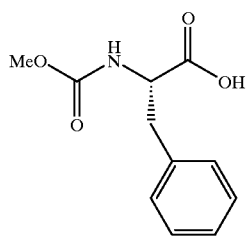

To a 0° C. solution of L-phenylalanine (25 g, 151 mmol) in aqueous 1N NaOH (175 mL) was added methyl chloroformate (15 g, 159 mmol) via syringe over several minutes. The pH was adjusted to 14 with 1N NaOH and the resulting clear solution was stirred for 1 hour. The basic solution was extracted with ether (3×) and the organics were discarded. The pH was adjusted to 3 with a cold phosphoric acid (~1N) and the acidic solution was extracted with methylene chloride (3×). The combined organics were washed with brine, dried (Na$_2$SO$_4$) and concentrated in vacuo to give 1a (32 g) as an extremely viscous oil which was carried on without further purification.

EXAMPLE 1B

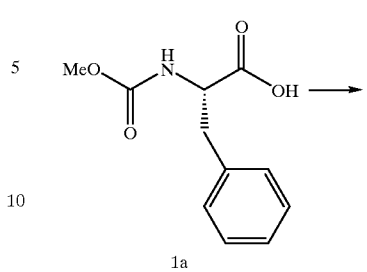

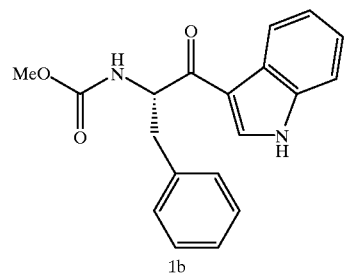

To a 0° C. solution of 1a (4.9 g, 21 mmol) in anhydrous diethyl ether (250 mL) was added PCl$_5$ (5.25 g, 25.5 mmol) over several minutes. The resulting suspension was allowed to stir for 1 hour during which time it slowly became a pale yellow solution. Solvent was removed in vacuo and the resulting acid chloride was dried under high vacuum for 1 hour. The crude acid chloride was then dissolved in methylene chloride (250 mL), cooled to 0° C., and indole (2.9 g, 25.2 mmol) was added over 10 minutes. AlCl$_3$ (5.5 g, 50 mmol) was then added over a period of 5 minutes, during which time the solution became a blood-red color, and the reaction mixture was allowed to warm to ambient temperature and stir for 16 hours. The reaction mixture was poured into cold water and extracted with methylene chloride. The combined organics were washed with brine, dried (Na$_2$SO$_4$) and concentrated in vacuo to give 7.5 g of a crude red solid. Flash chromatography (hexane-ethyl acetate, gradient elution 3:1 to 1:1) gave 2.6 g of a product 1b containing ~60% of the desired acylation product which was carried on without further purification.

EXAMPLE 1C

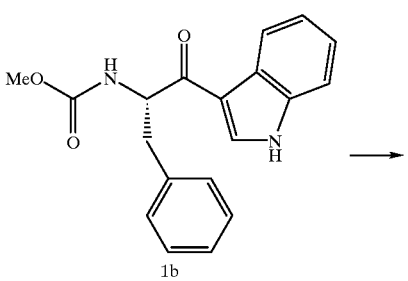

-continued

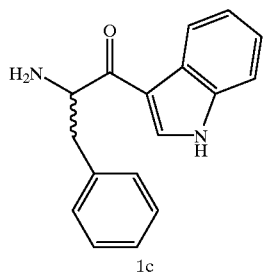

1c

To a solution of 1b (2.4 g) in 3:1 MeOH/water (40 mL) was added KOH (2.1 g, 37.3 mmol). The resulting solution was heated at reflux for 18 hours, cooled and acidifed with 1N phosphoric acid. The acidic aqueous layer was extracted with ethyl acetate (3×) and the organic layer discarded. The aqueous layer was made basic with aqueous 3N NaOH solution and extracted with methylene chloride (3×). The combined organics were washed with brine, dried ($Na_2SO_4$) and concentrated in vacuo to give the desired compound 1c (482 mg) as a racemic mixture.

EXAMPLE 1D

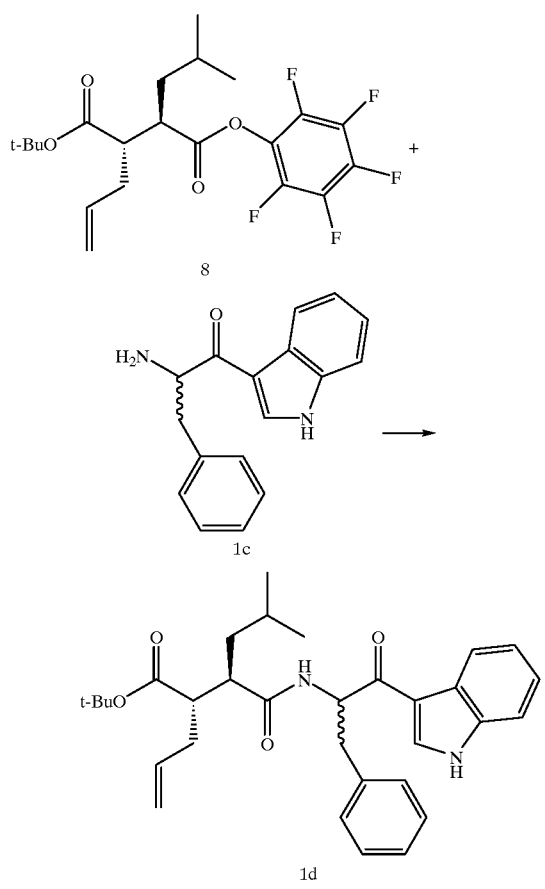

To a solution of 1c (0.48 g, 1.8 mmol) in DMF was added succinate ester 6 (0.8 g, 1.8 mmol). The reaction was allowed to stir at ambient temperature for 16 hours, then was warmed to 45° C. for 3 days. The reaction mixture was diluted with ethyl acetate and the organic layer washed with 1N NaOH, water (4×), dried ($Na_2SO_4$), filtered and concen- trated to give 1 g of a tan foam. Flash chromatography (hexane-ethyl acetate 5:1) gave 1d (510 mg) as a 1:1 mixture of epimers at the Phe center.

EXAMPLE 1E

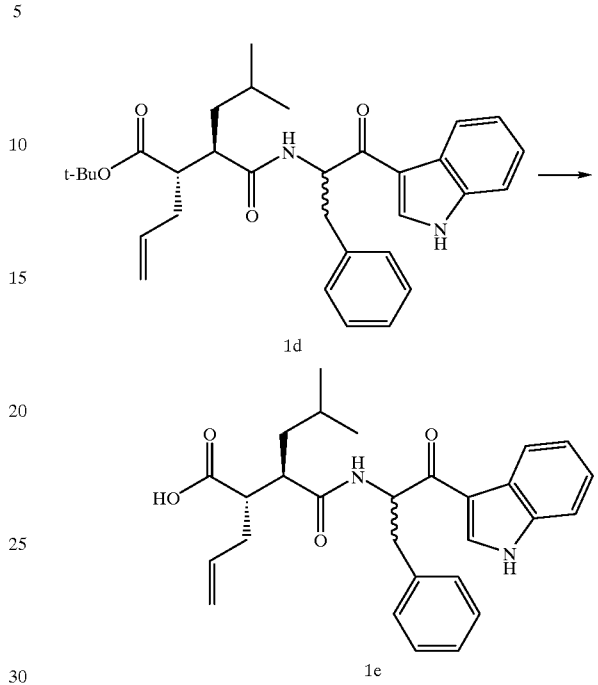

Ester 1d (0.5 g, 1.0 mmol) was dissolved in cold (0°) TFA and stirred for 5 hours while warming to ambient tempera- ture. Solvent was removed under a stream of nitrogen and the residue was azeotroped with methylene chloride and dried on high vacuum for 16 hours to give 1e (250 mg) as a 1:1 mixture of epimers at the Phe center.

EXAMPLE 1F

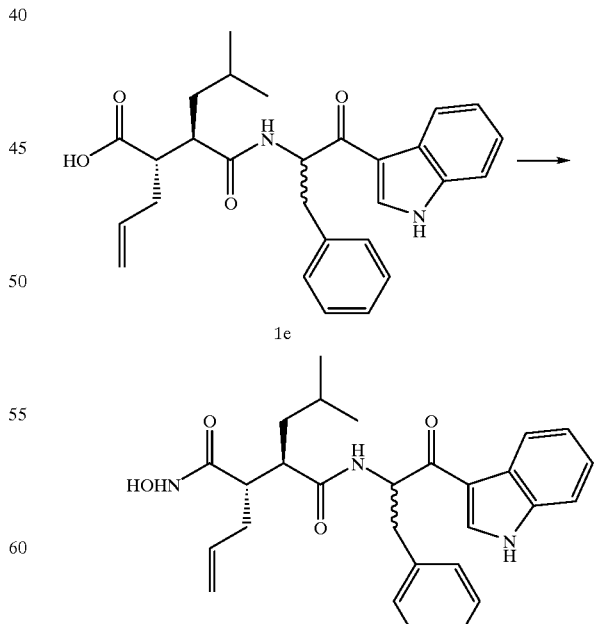

To a cold (0°) solution of 1e (0.25 g, 0.54 mmol) in DMF was added NMM (0.08 g, 0.81 mmol, 0.09 mL), HOBT (0.08 g, 0.59 mmol) and EDCI (0.11 g, 0.59 mmol). The resulting solution was stirred for 5 minutes and tertr-butyltrimethylsilylhydroxylamine (0.09 g, 0.59 mmol) was added in one portion. The resulting solution was warmed to ambient temperature and allowed to stand for 97 hours. The reaction mixture was diluted with EtOAc, washed with water (3×) and brine, dried ($Na_2SO_4$), filtered and concentrated in vacuo. Flash chromatography (1–3% methanol-methylene chloride) gave the desired compound (80mg) as a tan solid which was a 1:1 mixture of epimers at the Phe center. mp 180–210° (dec). $^1$H NMR (300 MHz, DMSO-d6) δ12.02 (s, 1H), 10.4 (s, 1H), 8.64–8.17 (m, 3H), 8.22–8.17 (m, 2H), 7.48–7.13 (m, 7H), 5.42–5.39 (m, 2H), 4.82–4.52 (m, 3H), 3.12–30.7 (m, 2H), 2.97–2.91 (m, 2H), 2.41–2.38 (m, 2H), 2.0–1.94 (m, 3H), 1.30–1.25 (m, 2H), 1.10–1.01 (m, 2H), 0.8–0.56 (m, 8H). MS ($DCI/NH_3$) m/e 476 (M+H)$^+$. Anal calcd for $C_{28}H_{33}N_3O_4$: C, 70.71; H, 6.99; N, 8.83. Found: C, 70.50; H, 6.99; N, 8.60.

EXAMPLE 1G

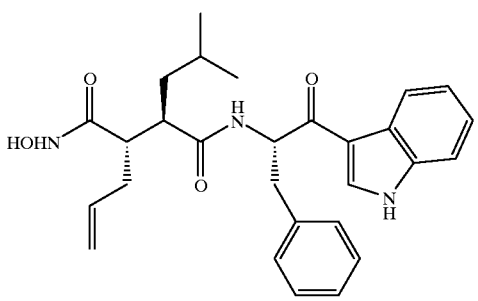

Separation of the diastereomers prepared in Example 1F by HPLC gave the compound of Example 1G. mp 190–210° C. (dec). $^1$H NMR (300 MHz, DMSO-d6) δ11.95 (s, 1H), 10.36 (s, 1H), 8.68 (s, 1H), 8.51–8.46 (m, 2H), 7.48–7.46 (m, 1H), 7.40–7.37 (d, 2H, J=7.1 Hz), 7.25–7.10 (m, 4H), 5.44–5.33 (m, 2H), 4.82–4.67 (m, 2H), 3.14–3.12 (dd, 1H, J=4.1, 9.4 Hz), 2.97–2.89 (m, 1H), 2.39–2.35 (m, 1H), 1.98–1.83 (m, 2H), 1.30–1.25 (m, 2H), 1.21–0.99 (m, 1H), 0.85–0.77 (m, 1H), 0.67–0.65 (d, 3H, J=6.4 Hz), 0.55–0.53 (d, 3H, J=6.8 Hz). MS ($DCI/NH_3$) m/e 476 (M+H)$^+$. Anal calcd for $C_{28}H_{33}N_3O_4 \cdot 0.75 H_2O$: C, 68.76; H, 7.11; N, 8.59. Found: C, 68.77; H, 6.66; N, 8.52. $[\alpha]_d$=−4.19° (c, 0.31, DMF).

EXAMPLE 1H

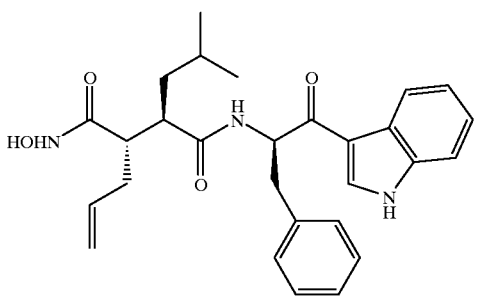

The desired compound was isolated in the chromatography of Example 1G. mp 170–210° C. (dec). $^1$H NMR (DMSO) δ12.03 (s, 1H), 10.39 (s, 1H), 8.71 (s, 1H), 8.64–8.61 (d, 1H, J=7.8 Hz), 8.55 (s, 1H), 8.22–8.19 (d, 1H, J=6.4 Hz), 7.49–7.47 (d, 1H, J=6.4H), 7.38–7.35 (d, 2H, J=7.8 Hz), 7.27–7.17 (m, 5H), 5.41–5.40 (m, 2H), 4.72–4.68 (d, 1H, J=7.8 Hz), 4.56–4.50 (d, 1H, J=14.9 Hz), 3.12–3.07 (m, 1H), 2.95–2.91 (m, 1H), 2.42–2.41 (m, 1H), 2.00–1.99 (m, 1H), 1.76–1.72 (m, 1H), 1.26–1.25 (m, 1H), 0.80–0.72 (m, 1H), 0.62–0.56 (m, 6H). MS ($DCI/NH_3$) m/e 476 (M+H)$^+$. Anal calcd for $C_{28}H_{33}N_3O_4 \cdot 5/4 H_2O$: C, 67.52; H 7.18; N, 8.44. Found: C, 67.54; H, 6.94; N, 8.42. $[\alpha]_d$= 36.67° (c, 0.24, DMF).

EXAMPLE 2

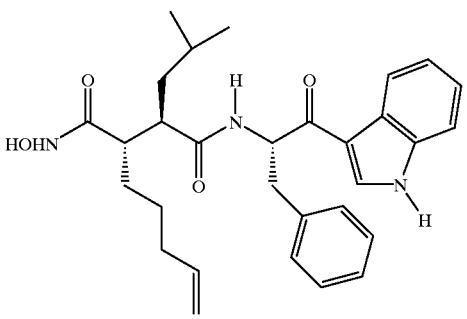

EXAMPLE 2A

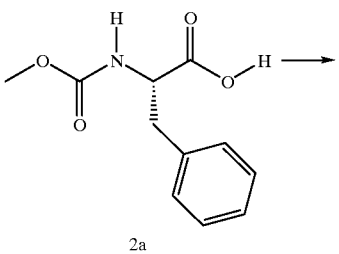

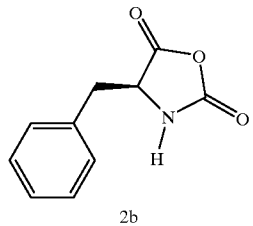

To a solution of methyl carbamate 2a (63.32 g, 280 mmol) in ether (1L) was added $PBr_3$ (10.8 mL, 110 mmol) via syringe at ambient temperature. The solution was allowed to stir overnight. The solvent was removed in vacuo and the resulting N-carboxyanhydride 2b (54.2 g, 100%) was dried on under high vacuum for 2 hours. The product was carried forward without further purification.

EXAMPLE 2B

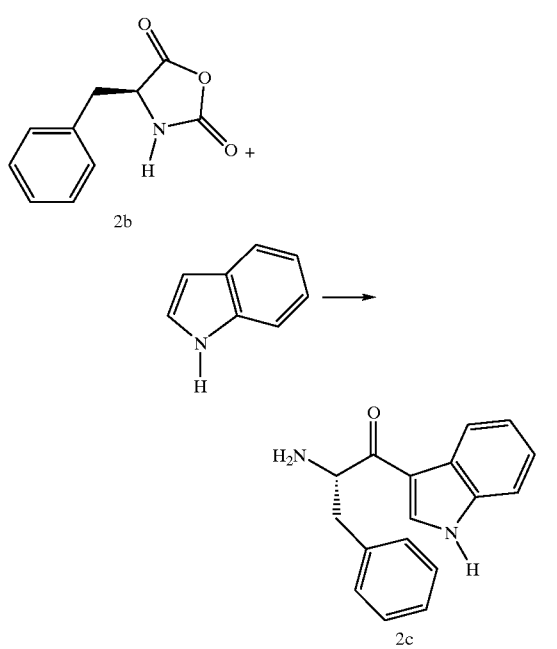

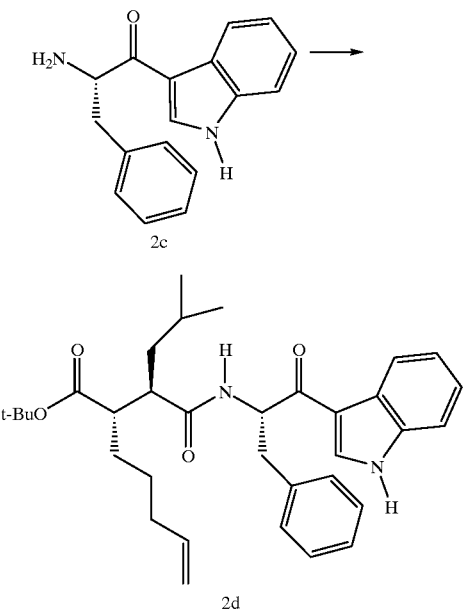

To a solution of 2b (28.35 g, 148 mmol) was added indole (139.12 g, 740 mmol) in one portion. The reaction mixture was cooled to 0° C. and AlCl$_3$ (59.22 g, 445 mmol) was added slowly via solid addition funnel. Upon complete addition of AlCl$_3$, the cold bath was removed and the solution was allowed to stir for 4 hours while warming to ambient temperature. The reaction was quenched by pouring onto 250 mL ice. The pH was adjusted to 12 by the dropwise addition of NH$_4$OH. The aqueous layer was extracted twice with CH$_2$Cl$_2$. The combined organic layers were washed with brine, dried (MgSO$_4$), filtered, and concentrated in vacuo to a brown oil. Flash chromatography (1:2:97 to 1:3:96 NH$_4$OH—MeOH—CH$_2$Cl$_2$) gave 2c (5 g, 16%) as a tan solid.

A solution of acid succinate ester 4 (1.107 g, 3.7 mmol) in 20 mL DMF was cooled to 0° C. NMM (975 mg, 8.9 mmol) was added via syringe, followed by HOBT (602 mg, 4.5 mmol), EDCI (856 mg, 4.5 mmol), and 2c (1.18 g, 4.5 mmol). The solution was allowed to stir overnight while warming to ambient temperature. The reaction was quenched with water and extracted twice with EtOAc. The combined organic layers were washed with brine, dried (MgSO$_4$), filtered, and concentrated in vacuo. The resulting orange foam was chromatographed (1% MeOH—CH$_2$Cl$_2$) to give 2d (1.607 g, 80%).

EXAMPLE 2C

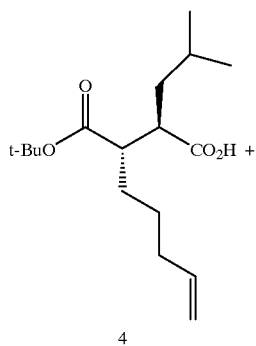

EXAMPLE 2D

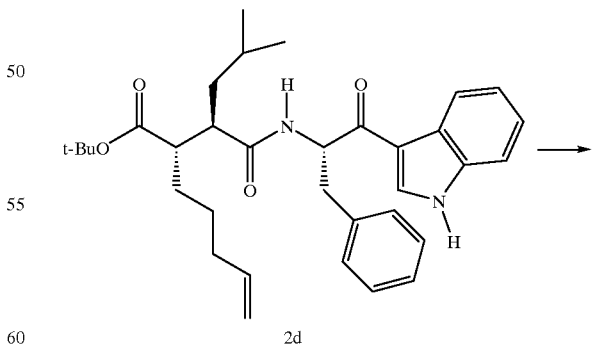

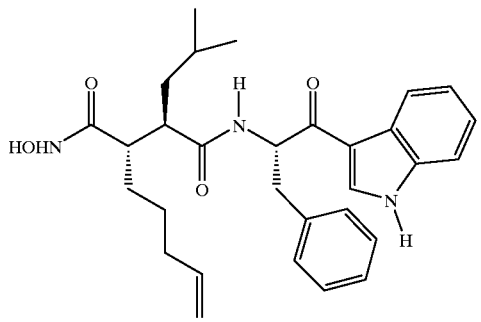

The desired compound was prepared according to the method of Examples 1E and F, except substituting 2d for 1d. mp 188° C. (dec). $^1$H NMR (300 MHz, DMSO-d6) δ11.99 (d, 1H, J=3.0 Hz), 10.41 (d, 1H, J=1.5 Hz), 8.74 (d, 1H, J=1.8 Hz), 8.56–8.44 (m, 2H), 8.20–8.17 (m, 1H), 7.49–7.16 (m, 8H), 5.74–5.58 (m, 1H), 5.49–5.35 (m, 1H), 4.95–4.86 (m, 2H), 3.18–2.93 (m, 2H), 2.42–2.30 (m, 1H), 2.21–2.11 (m, 1H), 1.96–1.56 (m, 3H), 1.47–0.72 (m, 6H), 0.61 (dd, 6H, J=36.4, 6.7 Hz). MS (APCI) m/e 504 (M+1). Anal calcd for $C_{30}H_{37}N_3O_4$: C, 71.54; H, 7.40; N, 8.34. Found: C, 70.72; H, 7.05; N, 7.10. $[\alpha]_d=-35°$.

EXAMPLE 3

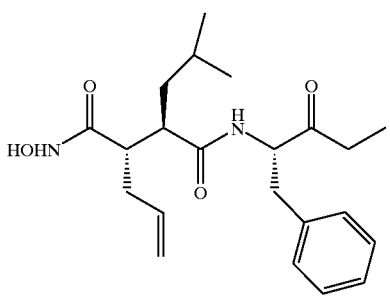

EXAMPLE 3A

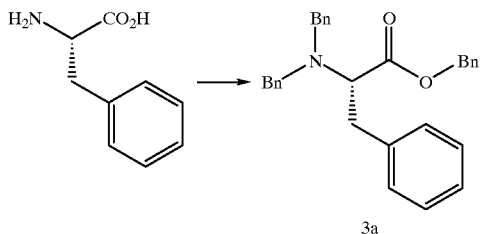

To a solution of phenylalanine (10 g, 61 mmol) in 500 mL of $H_2O$ was added $K_2CO_3$ (27.6 g, 200 mmol) and benzyl bromide (24 mL, 200 mmol). The reaction mixture was heated at reflux for 2.5 days and then was quenched with 1M HCl and extracted with $CH_2Cl_2$. The organic layer was washed with $H_2O$, 1M NaOH and brine. The organic layer was dried (MgSO$_4$), filtered, and concentrated in vacuo. Flash chromatography (20% EtOAc-hexane) gave 3a (48%).

EXAMPLE 3B

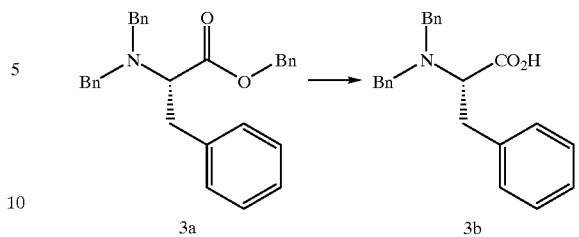

To a solution of 3a (5.05 g, 1.16×10$^{-2}$ mol) in 2:1 dioxane/water (300 mL) was added KOH (0.65 g, 1.16×10$^{-2}$ mol) and the reaction mixture was stirred for 2 days. The reaction mixture was acidified with 1M HCl and extracted with EtOAc. The organic layer was dried (MgSO$_4$), filtered, and concentrated in vacuo. Flash chromatography (40% EtOAc-hexane) gave 3b.

EXAMPLE 3C

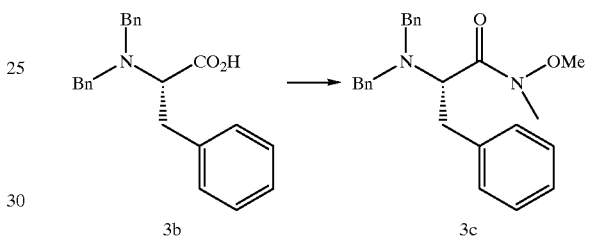

To a 0° C. solution of 3c (2.0 g, 5.8×10$^{-3}$ mol) in 30 mL $CH_2Cl_2$ was added EDCI (1.22 g, 6.36.×10$^{-3}$ mol), N,O-dimethylhydroxylamine hydrochloride (0.62 g, 6.36×10$^{-3}$ mol), and NMM (0.764 mL, 6.96×10$^{-3}$ mol) and the reaction mixture was stirred at 0° C. for 10 minutes. The cold bath was removed and the reaction was allowed to warm to ambient temperature and stir overnight. The reaction was quenched with $H_2O$ and extracted with $CH_2Cl_2$. The organic layer was washed with citric acid, saturated aqueous NaHCO$_3$, pH 7 buffer and brine. The organic layer was dried (MgSO$_4$), filtered, and concentrated in vacuo. Flash chromatography (20% EtOAc-hexane) gave 3c (48% yield).

EXAMPLE 3D

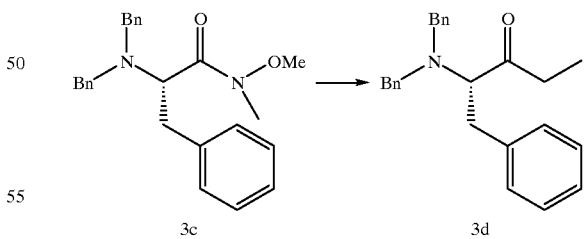

To a 0° C. solution in THF (20 mL) of Weinreb amide 3c (588 mg, 1.5 mmol) was added ethylmagnesium bromide (1 mL, 3 mmol) via syringe. The ice bath was removed and the reaction mixture was allowed to warm to ambient temperature and stir for 3.5 hours. The reaction was quenched with $H_2O$ and extracted with EtOAc. The organic layer was washed with brine, dried (MgSO$_4$), filtered, and concentrated in vacuo. Flash chromatography (5% EtOAc-hexane) gave the desired product 3d in 36% yield.

EXAMPLE 3E

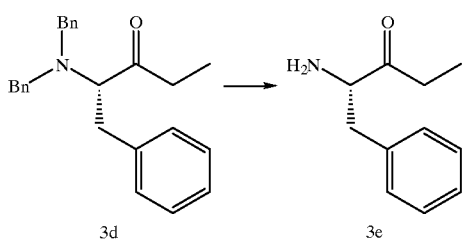

To a solution of ketone 3d (554 mg, 1.55 mmol) in 50 mL MeOH was added 20% Pd(OH)$_2$/C and the reaction was stirred for 24 hours. The reaction was filtered to remove the catalyst and concentrated in vacuo to give the desired product in 3e 91% yield.

EXAMPLE 3F

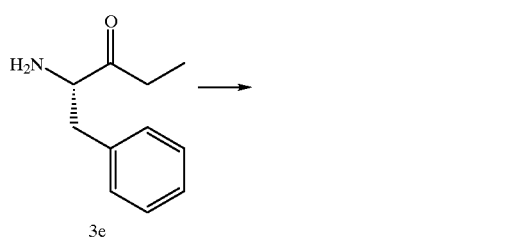

The desired compound was prepared according to the method of Examples 1D–F, except substituting 3e for 1c. mp 145° C. (dec). $^1$H NMR (300 MHz, DMSO-d6) δ10.36 (d, 1H, J=1.7 Hz), 8.69 (d, 1H, J=1.7 Hz), 8.20 (d, 1H, J=8.8 Hz), 7.09–7.30 (m, 5H), 5.23–5.39 (m, 1H), 4.60–5.00 (m, 2H), 4.46–4.57 (m, 1H), 2.56–2.94 (m, 2H), 2.29–2.39 (m, 1H), 1.64–1.94 (m, 3H), 1.26–1.50 (m, 2H), 0.98–1.08 (m, 1H), 0.92 (t, 3H, J=7.4 Hz), 0.84–0.96 (m, 2H), 0.78 (dd, 6H, J=6.4, 16.6 Hz). [α]$_d$=+30.4°

EXAMPLE 4

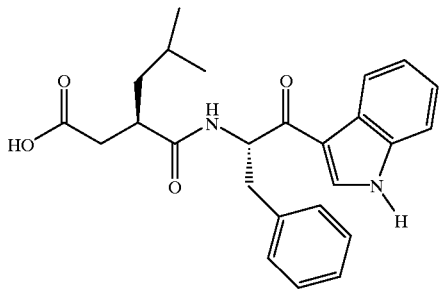

The desired compound was prepared by coupling of 2c and R-2-(i-butyl)-succinic acid-4-t-butyl ester according to the method of Example 2C, followed by hydrolysis of the tert-butyl ester using the method of Example 1E. mp 110° C. (dec). $^1$H NMR (300 MHz, DMSO-d6) δ12.08 (s, 1H), 11.92 (d, 1H, J=2.7 Hz), 8.43 (d, 1H, J=8.5 Hz), 8.30 (d, 1H, J=3.1 Hz), 8.16–8.19 (m, 1H), 7.44–7.47 (m, 1H), 7.11–7.30 (m, 8H), 5.32–5.42 (m, 1H), 2.87–3.19 (m, 2H), 2.61–2.74 (m, 1H), 2.04–2.25 (m, 2H), 1.18–1.40 (m, 2H), 0.97–1.08 (m, 1H), 0.69 (dd, 6H, J=6.5, 16.3 Hz). MS (APCI) m/e 421 (M+1), 438 (M+18). Anal calcd for C$_{25}$H$_{28}$N$_2$O$_4$. 0.5H$_2$O: C, 69.90; H, 6.80; N, 6.52. Found: C, 69.83; H, 6.80; N, 6.49. [α]$_d$=+7.2°.

EXAMPLE 5

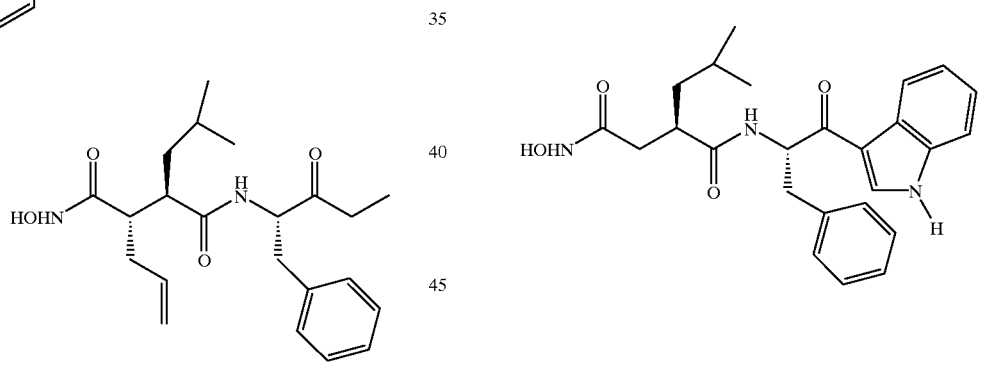

EXAMPLE 5A

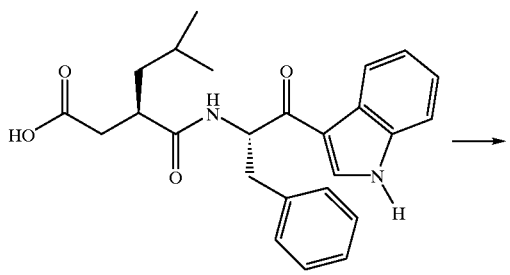

41
-continued

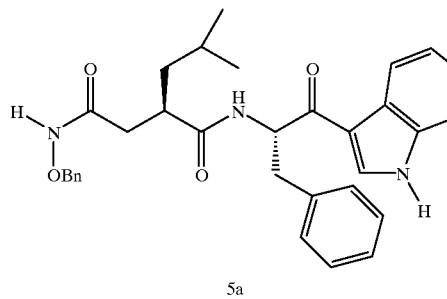

5a

A pH 4 solution in 1.5:1 THF-H₂O of the compound of Example 4 (50 mg, 1.0×10⁻¹ mmol) and O-benzylhydroxylamine hydrochloride (26 mg, 1.6×10⁻¹ mmol) was cooled to 0° C. and EDCI (63 mg, 3.3×10⁻¹ mmol) was added. The reaction stirred at 0° C. for 1 hour. The ice bath was removed and the reaction mixture was warmed to ambient temperature and stirred overnight. The THF was removed in vacuo and the remaining liquid was partioned between EtOAc and citric acid. The organic layer was washed with brine, dried (MgSO₄), filtered and concentrated in vacuo. Flash chromatography (1% MeOH—CH₂Cl₂) gave the desired product 5a in 46% yield.

EXAMPLE 5B

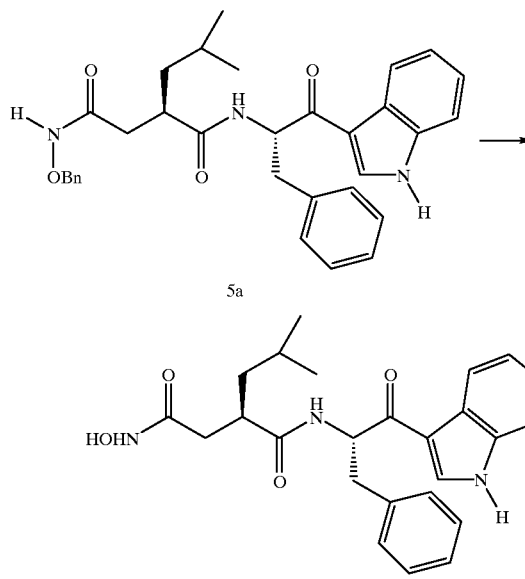

5a

A mixture of benzyl hydroxamate 5a (0.266 g, 5.1×10⁻⁴ mol) and Pd/C (0.133 g) in 10 mL of THF was stirred overnight under 1 atm of H₂. The reaction mixture was gravity filtered through a plug of celite. Solvent was removed in vacuo to give the desired product in 82% yield as a tan solid. mp 120° C. ¹H NMR (300 MHz, DMSO-d6) δ11.94 (s, 1H), 10.33 (s, 1H), 8.71 (s, 1H), 8.47 (d, 1H, J=8.5 Hz), 8.33 (s, 1H), 8.16–8.20 (m, 1H), 7.44–7.48 (m, 1H), 7.11–7.31 (m, 7H), 5.30–5.39 (m, 1H), 2.89–3.16 (m, 2H), 2.64–2.77 (m, 1H), 1.83 (d, 2H, J=7.4 Hz), 1.29–1.40 (m, 1H), 1.14–1.26 (m, 1H), 0.86–0.97 (m, 1H), 0.66 (dd, 6H, J=0.66, 10.3 Hz). MS (CI) m/e 436 (M+1). Anal calcd for C₂₅H₂₉N₃O₄. 1.00 H₂O: C, 66.20; H, 6.88; N, 9.26. Found: C, 66.34; H, 6.74; N, 8.99. [α]_d=-11.5°.

42
EXAMPLE 6

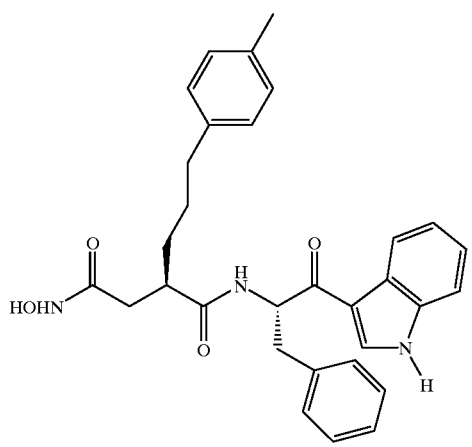

The desired compound was prepared by coupling of 2c and succinate ester 5 according to the method of Example 2C, followed by hydrolysis of the tert-butyl ester using the method of Example 1E, and conversion of the acid to the hydroxamate according to the method of Example 5. mp 185° C. ¹H NMR (300 MHz, DMSO-d6) δ11.94 (d, 1H, J=2.6 Hz), 10.35 (s, 1H), 8.70 (s, 1H), 8.53 (d, 1H, J=8.8 Hz), 8.35 (d, 1H, J=3.4 Hz), 8.20–8.23 (m, 1H), 7.46–7.51 (m,1H), 7.10–7.31 (m, 7H), 6.70 (dd, 4H, J=8.1, 25.7 Hz), 5.33–5.43 (m, 1H), 2.87–3.19 (m, 2H), 2.61–2.75 (m, 1H), 2.14–2.44 (m, 2H), 2.14 (s, 3H), 1.88 (d, 2H, J=7.3 Hz), 1.11–1.42 (m, 4H). MS (CI) m/e 512 (M+1). Anal calcd for C₃₁H₃₃N₃O₄.0.75 H₂O: C, 70.90; H, 6.62; N, 8.00. Found: C, 71.20; H, 6.63; N, 7.72. [α]_d=-5.8°.

EXAMPLE 7

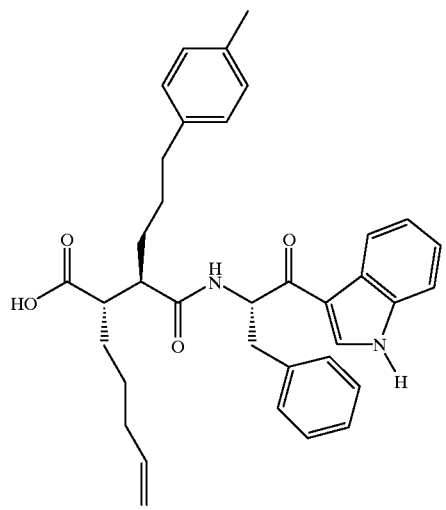

The desired compound was prepared by coupling of 2c and succinate ester 6 according to the method of Example 2C, followed by hydrolysis of the tert-butyl ester using the method of Example 1E. ¹H NMR (300 MHz, DMSO-d6) δ12.01 (d, 1H, J=3.0 Hz), 8.63 (d, 1H, J=9.2 Hz), 8.49 (d, 1H, J=3.3 Hz), 8.25–8.22 (m, 1H), 7.52–7.48 (m, 1H), 7.37–7.13 (m, 7H), 6.68 (dd, 4H, J=34.2, 8.1 Hz), 5.7405.61 (m, 1H), 5.52–5.45 (m, 1H), 4.97–4.87 (m, 2H), 3.91 (br, 1H), 3.16–2.92 (m, 2H), 2.40–2.10 (m, 4H), 2.15 (s, 3H), 1.87–1.63 (m, 2H), 1.44–0.96 (m, 7H), 0.84–0.70 (m, 1H). MS (CI) m/e 565 (M+1). Anal calcd for $C_{36}H_{40}O_4N_2 \cdot 1.5$ $H_2O$: C, 73.07; H, 7.32; N, 4.73. Found: C, 73.13; H, 6.97; N, 4.98.

EXAMPLE 8

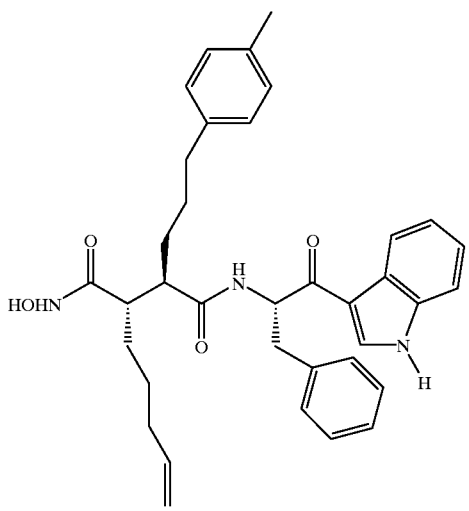

The desired compound was prepared according to the method of Example 5, except substituting the compound of Example 7 for the compound of Example 4. mp 220° C. $^1$H NMR (300 MHz, DMSO-d6) δ12.02 (s, 1H), 10.48 (s, 1H), 8.77 (s, 1H), 8.60 (d, 1H, J=9.2 Hz), 8.53 (s, 1H), 8.29–8.26 (m, 1H), 7.56–7.15 (m, 8H), 6.70 (dd, 4H, J=34.6, 7.8 Hz), 5.80–5.64 (m, 1H), 5.55–5.44 (m, 1H), 5.02–4.90 (m, 2H), 3.23–2.90 (m, 2H), 2.44–2.28 (m, 3H), 2.19 (s, 3H), 2.08–1.96 (m, 1H), 1.91–1.66 (m, 2H), 1.48–0.96 (m, 7H), 0.76–0.63 (m, 1H). MS (ESI) m/e 580 (M+1), 602 (M+Na). Anal calcd for $C_{36}H_{41}N_3O_4 \cdot 1.25$ $H_2O$: C, 71.79; H, 7.28; N, 6.97. Found: C, 71.59; H, 7.05; N, 7.06. $[\alpha]_d=-20.4°$.

EXAMPLE 9

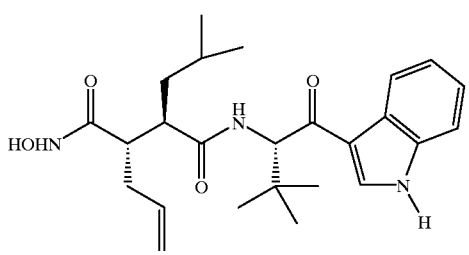

EXAMPLE 9A

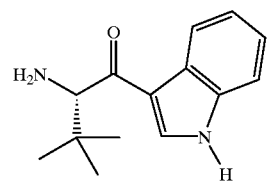

9a

The desired compound was prepared according to the method of Examples 1A–C, except substituting L-tert-leucine for L-phenylalanine.

EXAMPLE 9B

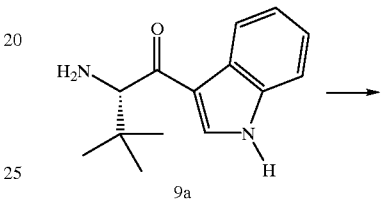

9a

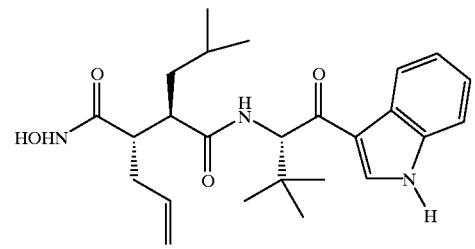

The desired compound was prepared according to the method of Examples 2B and C, except substituting 9a for 2c and substituting succinate ester 2 for succinate ester 4. mp 218° C. (dec). $^1$H NMR (300 MHz, DMSO-d6) δ11.92 (s, 1H), 10.45 (s, 1H), 8.73 (s, 1H), 8.36 (d, 1H, J=3.1 Hz), 8.17–8.21 (m, 1H), 8.12 (d, 1H, J=8.8 Hz), 7.44–7.47 (m, 1H), 7.13–7.25 (m, 2H), 5.54–5.70 (m, 1H), 5.10 (d, 1H, J=8.8 Hz), 4.87–4.97 (m, 2H), 2.73 (dt, 1H, J=2.7, 10.9 Hz), 2.23–2.37 (m, 1H), 1.98–2.20 (m, 2H), 1.28–1.39 (m, 1H), 0.96–1.16 (m, 1H), 1.00 (s, 9H), 0.82–0.94 (m, 1H), 0.62 (dd, 6H, J=6.1, 40.3 Hz). MS (DCI) m/e 442 (M+H)$^+$. Anal calcd for $C_{25}H_{35}N_3O_4 \cdot 0.5$ $H_2O$: C, 66.64; H, 8.05; N, 9.32. Found: C, 66.59; H, 8.01; N, 9.10. $[\alpha]_d=-55.9°$.

EXAMPLE 10

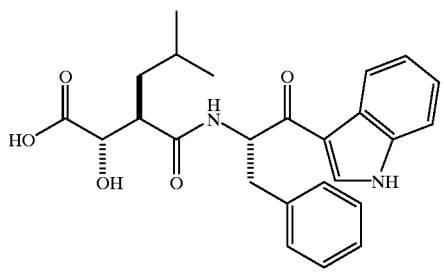

EXAMPLE 10A

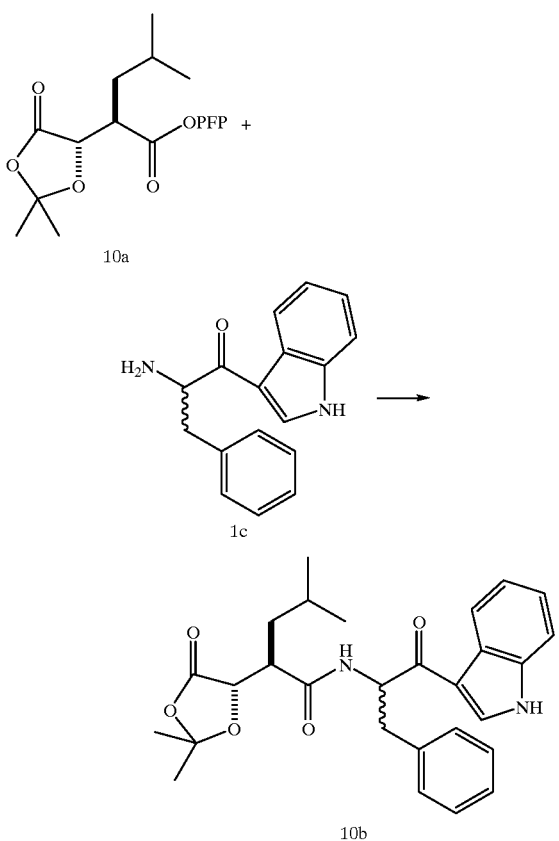

Pentafluorophenol ester 10a (0.605 g, 1.53 mmol), prepared as described in WO94/02446, and 1c (0.448 g, 1.70 mmol) were combined in dry DMF (6 mL). The solution was heated at 30° C. for 24 hours, then reduced in volume by rotary evaporation under high vacuum. The residue was diluted with ethyl acetate, then washed successively with brine, pH3 buffer, aqueous Na₂CO₃, pH7 buffer and brine. The organics were dried over Na₂SO₄ and evaporated to give 10b (0.764 g) as a tan solid which was carried forward without purification.

EXAMPLE 10B

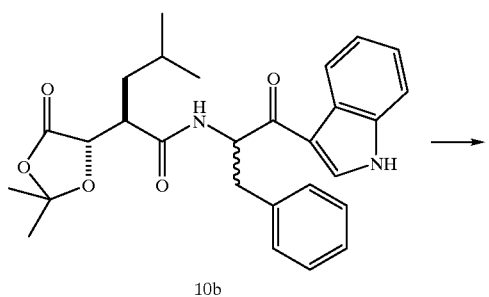

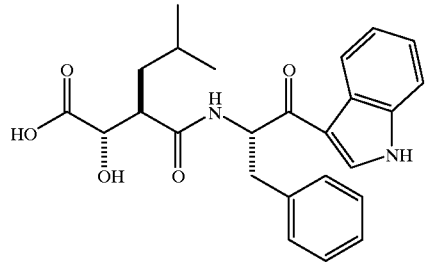

To a 0° C. solution in THF (12 mL) of dioxolanone 3 (0.728 g, 1.5 mmol) was added 2.1 M HCl (12 mL) and the solution allowed to warm to ambient temperature over 18 hours. The solution was evaporated to dryness to give a tan foam (0.70 g). The crude material was purified by reverse phase HPLC to give the desired compound (0.223 g) as a white foam. $^1$H NMR (DMSO-d6) 0.65 (d, 3H, J=6.4 Hz), 0.72 (d, 3H, J=6.5 Hz), 1.02 (m, 1H), 1.23 (m, 1H), 1.41 (m, 1H), 2.62 (m, 1H), 2.94 (dd, 1H, J=7.4, 13.9 Hz), 3.17 (dd, 1H, J=6.5, 13.9 Hz), 3.91 (d, 1H, J=7.1 Hz), 5.38 (m, 1H), 7.22 (m, 6H), 7.45 (dd, 1H, J=2.3, 6.4 Hz), 8.16 (dd, 1H, J=2.3, 6.1 Hz), 8.27 (d, 1H, J=3.0 Hz), 8.41 (d, 1H, J=3.0 Hz), 8.58 (bds, 1H), 11.91 (d, 1H, J=2.7 Hz). MS (DCI/NH₃) M/e 454 (M+NH₄)⁺, 437 (M+H)⁺, 419, 265. Anal. Calcd for $C_{25}H_{28}N_2O_5 \cdot .75 H_2O$: C, 66.72; H, 6.61; N, 6.22. Found: C, 66.71; H, 6.30; N, 5.90.

EXAMPLE 11

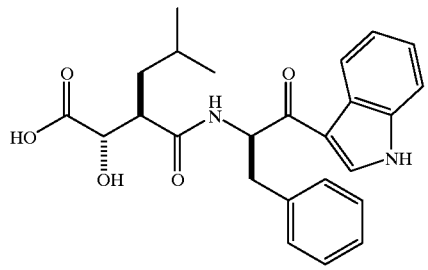

The desired compound was the slower eluting species in the chromatography described in Example 1. $^1$H NMR (DMSO-d6) 0.63 (d, 3H, J=5.5 Hz), 0.71 (d, 3H, J=5.5 Hz), 0.87 (m, 2H), 1.27 (m, 1H), 2.59 (m, 1H), 2.89 (dd, 1H, J=10.0, 13.6 Hz), 3.09 (dd, 1H, J=4.7, 13.6 Hz), 3.83 (d, 1H, J=7.8 Hz), 5.43 (m, 1H), 7.21 (m, 4H), 7.32 (d, 2H, J=6.9 Hz), 7.46 (dd, 1H, J=1.8, 5.5 Hz), 8.21 (dd, 1H, J=2.6, 5.5 Hz), 8.47 (d, 1H, J=3.3 Hz), 8.64 (d, 1H, J=8.9 Hz), 11.98 (d, 1H, J=2.6 Hz). MS (DCI/NH₃) m/e 454 (M+NH₄)⁺, 437 (M+H)⁺, 265. Anal calcd for $C_{25}H_{28}N_2O_5$: C, 68.79; H, 6.47; N, 6.42. Found: C, 67.87; H, 7.14; N, 5.54.

EXAMPLE 12

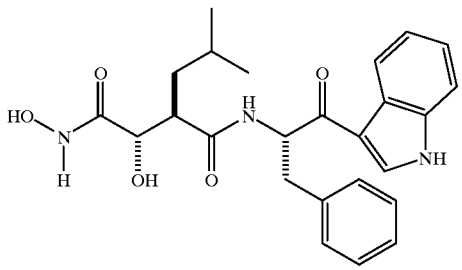

The desired compound was prepared according to the method of Example 5, except substituting the compound of Example 10 for the compound of Example 4. mp 122–125° C. $^1$H NMR (DMSO-d6) 0.63 (d, 3H, J=6.8 Hz), 0.68 (d, 3H, J=6.4 Hz), 0.85 (m, 1H), 1.08 (d, 1H), 1.37 (m, 1H), 2.63 (m, 1H), 2.94 (dd, 1H, J=6.8, 13.9 Hz), 3.18 (dd, 1H, J=7.2, 13.9 Hz), 3.77 (dd, 1H, J=6.8, 8.5 Hz), 5.22 (d, 1H, J=6.8 Hz), 5.37 (dd, 1H, J=6.8, 7.2 Hz), 7.19 (m, 6H), 7.45 (dd, 1H, J=0.7, 7.8 Hz), 8.13 (dd, 1H, J=2.0, 5.7 Hz), 8.25 (d, 1H, J=2.0 Hz), 8.37 (d, 1H, J=8.1 Hz), 8.83 (s. 1H), 10.59 (s, 1H), 11.92 (s, 1H). MS (DCI/NH$_3$) m/e 469 (M+NH$_4$)$^+$, 452 (M+H)$^+$. Anal calcd for C$_{25}$H$_{29}$N$_3$O$_5$. 0.33 H$_2$O: C, 65.64; H,6.53; N, 9.19. Found: C, 65.65; H, 6.54; N, 8.20. [α]$_d$=+12° (C=0.95, CH$_3$OH).

EXAMPLE 13

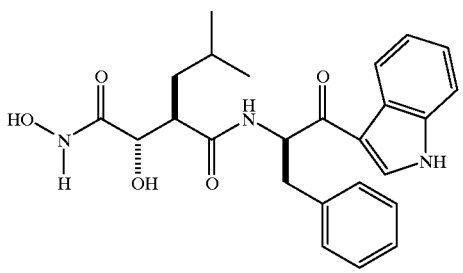

The desired compound was prepared according to the method of Example 5, except substituting the compound of Example 11 for the compound of Example 4. mp 172–175° C. $^1$H NMR (DMSO-d6) 0.62 (d, 3H, J=6.4 Hz), 0.69 (d, 3H, J=6.1 Hz), 0.79 (m, 1H), 0.88 (m, 1H), 1.23 (m, 1H), 2.62 (m, 1H), 2.90 (dd, 1H, J=9.5, 13.9 Hz), 3.09 (dd, 1H, J=4.7, 13.9 Hz), 3.68 (dd, 1H, J=6.5, 8.8 Hz), 5.01 (d(OH), 1H, J=6.1 Hz), 5.41 (m, 1H), 7.22 (m, 5H), 7.30 (s, 1H), 7.31 (dd, 1H, J=1.7, 7.0 Hz), 7.46 (dd, 1H, J=1.3, 8.5 Hz), 8.20 (dd, 1H, J=2.6, 8.5 Hz), 8.44 (d, 1H, J=9.5 Hz), 8.46 (s, 1H), 8.75 (s, 1H), 10.51 (s, 1H), 11.92 (s, 1H). MS (DCI/NH$_3$) m/e 469 (M+MH$_4$)$^+$, 452 (M+H)$^+$, 391. Anal calcd for C$_{25}$H$_{29}$N$_3$O$_5$.0.33 H$_2$O: C, 65.64; H, 6.53; N, 9.19. Found: C, 65.63; H, 6.74; N, 8.31. [α]$_d$=−9.1° (C=1.1, CH$_3$OH).

EXAMPLE 14

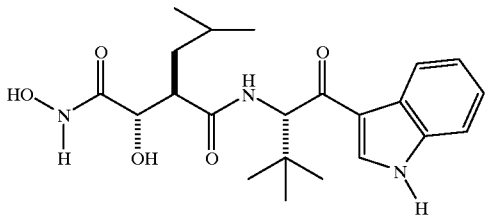

The desired compound was prepared according to the method of Examples 10 and 12, except substituting 9a for 1c. mp 144–146° C. $^1$H NMR (DMSO-d6) 0.65 (d, 3H, J=6.8 Hz), 0.69 (d, 3H, J=6.5 Hz), 0.89 (m, 1H), 0.98 (s, 9H), 1.20 (m, 1H), 1.41 (m, 1H), 2.77 (m, 1H), 3.73 (t, 1H, J=8.2 Hz), 5.12 (d, 1H, J=9.5 Hz), 5.24 (d, 1H, J=8.1 Hz), 7.12 (m, 2H), 7.46 (d, 1H, J=6.8 Hz), 7.78 (d, 1H, J=9.4 Hz), 8.21 (dd, 1H, J=1.7, 6.1 Hz), 8.36 (d, 1H, J=2.7 Hz), 8.84 (bds, 1H), 10.59 (bds, 1H), 11.96 (bds, 1H). $^{13}$C NMR (DMSO-d6) 21.58, 23.49, 25.12, 27.05, 34.42, 37.22, 47.57, 60.23, 71.47, 112.07, 116.61, 121.45, 121.68, 122.81, 125.49, 134.45, 136.59, 168.77, 172.44, 193.57. MS (DCI/NH$_3$) m/e 435 (M+NH$_4$)$^+$, 418 (M+H)$^+$. Anal calcd for C$_{22}$H$_{31}$N$_3$O$_5$.0.5 H$_2$O: C, 61.95; H, 7.56; N, 9.95. Found: C, 61.64; H, 7.69; N, 9.67. [α]$_d$=−57° (C=1.2, CH$_3$OH).

EXAMPLE 15

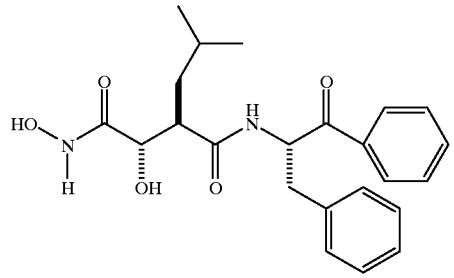

EXAMPLE 15A

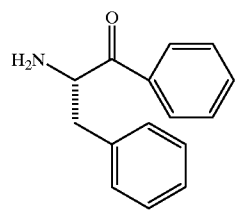

15a

The desired compound was prepared according to the method of Examples 3A–E, except substituting phenyllithium for ethylmagnesium bromide.

EXAMPLE 15B

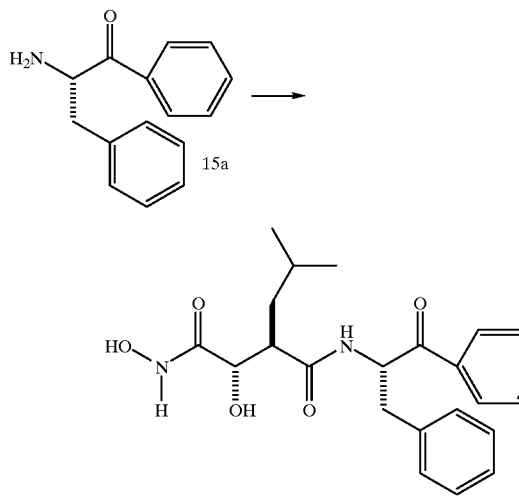

The desired compound was prepared according to the method of Examples 10 and 12, except substituting 15a for 1c. $^1$H NMR (CD$_3$OD) δ0.78 (d, 3H, J=6.5 Hz), 0.80 (d, 3H, J=6.5 Hz), 1.10 (m, 1H), 1.30 (m, 1H), 1.54 (m, 1H), 2.77 (m, 1H), 3.01 (dd, 1H, J=6.5, 13.6 Hz), 3.20 (dd, 1H, J=6.8, 13.9 Hz), 3.98 (d, 1H, J=7.1 Hz), 5.73 (t, 1H, J=6.8 Hz), 7.18 (m, 5H), 7.45 (t, 2H, J=7.8 Hz), 7.58 (m, 1H), 7.93 (d, 2H, J=7.1 Hz). MS (DCI/NH$_3$) m/e 430 (M+NH4)$^+$, 413 (M+H)$^+$. Anal calcd for C$_{23}$H$_{28}$N$_2$O$_5$·0.5H$_2$O: C, 65.54; H, 6.93; N, 6.65. Found: C, 65.57; H, 6.99; N, 6.52.

EXAMPLE 16

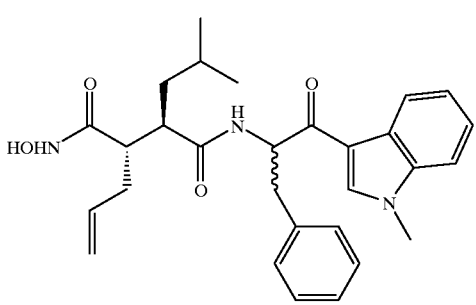

The desired compound was prepared according to the method of Example 1, except substituting 1-methylindole for indole. $^1$H NMR (300 MHz, DMSO-d6) δ10.36 (s, 1H), 8.68–8.46 (m, 3H), 8.32–8.18 (m, 1H), 7.56–7.18 (m, 7H), 5.43–5.33 (m, 2H), 4.82–4.6 (m, 2H), 3.88 (s, 3H), 3.12–3.07 (m, 1H), 2.95–2.90 (m, 1H), 2.40–2.39 (m, 1H), 2.03–1.88 (m, 2H), 1.34–1.26 (m, 2H), 0.81–0.56 (m, 7H). MS (DCI/NH$_3$) m/e 490 (M+H)$^+$. Anal calcd for C$_{29}$H$_{35}$N$_3$O$_4$·0.25 H$_2$O: C, 70.49; H, 7.24; N, 8.42. Found: C, 70.39; H, 7.37; N, 8.35.

EXAMPLE 17

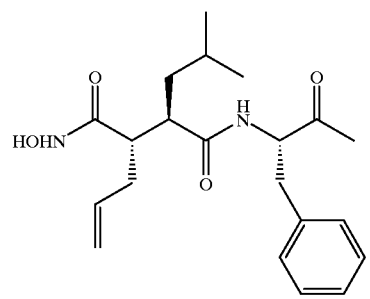

EXAMPLE 17A

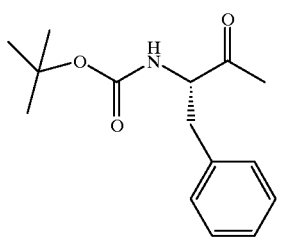

To a −78° C. solution of N-Boc-phenylalanine (2.69 g, 10 mmol) in 10 mL THF was added MeLi (22.9mL, 32 mmoL, 1.4M in ether) via addition funnel over 10 minutes. The cold bath removed and the solution allowed to warm to ambient temperature and stirred 2 hours. The reaction was quenched with 25 mL of 2N HCl solution, stirred for 10 minutes, and the aqueous layer was extracted with ether (3×). The combined organics were washed with brine, dried (Na$_2$SO$_4$) and concentrated in vacuo. Flash chromatography (hexane-ethyl acetate 5:1) gave 17a (1.31 g) as a waxy solid.

EXAMPLE 17B

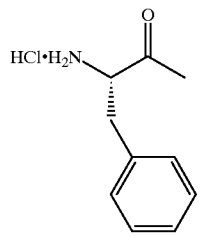

A 0° C. solution of 17a (1.31 g, 4.83 mmol) in 4N HCl/dioxane was stirred for 2 hours and then was diluted with diethyl ether. The residual solid was filtered and dried under high vacuum to give 17b (0.9 g) as the HCl salt.

EXAMPLE 17C

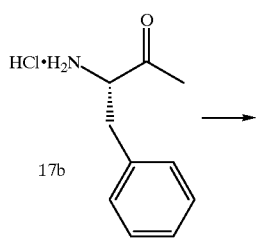

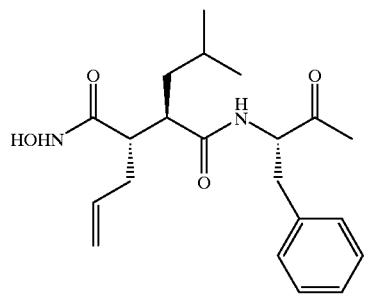

The desired compound was prepared according to the method of Examples 1D–F, except substituting 17b for 1c. mp 180° C. (dec). $^1$H NMR (DMSO-D6) δ10.37 (S, 1H), 8.71 (S, 1H), 8.47–8.38 (D, 1H, J=8.1 Hz), 7.30–7.13 (M, 5H), 5.36–5.30 (M, 1H), 4.80–4.06 (M, 3H), 3.10–3.04 (M, 1H), 2.72–2.64 (M, 1H), 2.41–2.39 (M, 1H), 2.11 (S, 3H), 1.92–1.90 (M, 1H), 1.79–1.70 (M, 1H) 1.39–1.35 (M, 2H), 1.23–1.20 (M, 2H), 0.84–0.75 (M, 7H). MS (DCI/NH$_3$) m/e 375 (M+H). Anal calcd for C$_{21}$H$_{30}$N$_2$O$_4$C: C, 67.35; H, 8.01; N, 7.48. Found: C, 66.95; H, 8.0 1; N, 7.31.

EXAMPLE 18

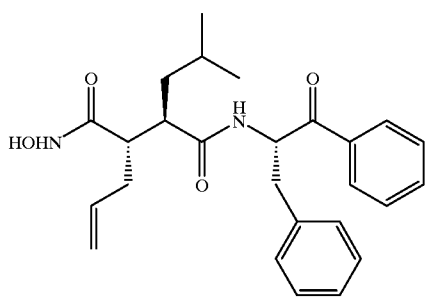

EXAMPLE 18A

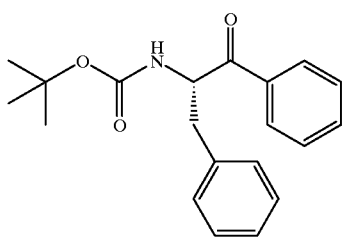

To a cold 0° C. solution of bromobenzene (5 g, 32 mmol) in THF was added nBuLi (12.8 mL, 32 mmol, 2.5M in diethyl ether) over the course of 5 minutes. The resulting yellow solution was stirred at 0° C. for 25 minutes and then was added to a –78° C. solution of N-BOC-1-phenylalanine (2.69 g, 10 mmol) over 25 minutes. The resulting yellow solution was allowed to warm to room temperature overnight (16 hours) and then was quenched with 1N HCl solution. The aqueous layer was extracted with ether (3×) and the combined organics were washed with 1N NaHCO$_3$ and brine, dried (MgSO$_4$) and concentrated in vacuo. Flash chromatography (hexane-ethyl acetate 6:1) gave 18a (0.25 g) as a waxy solid.

EXAMPLE 18B

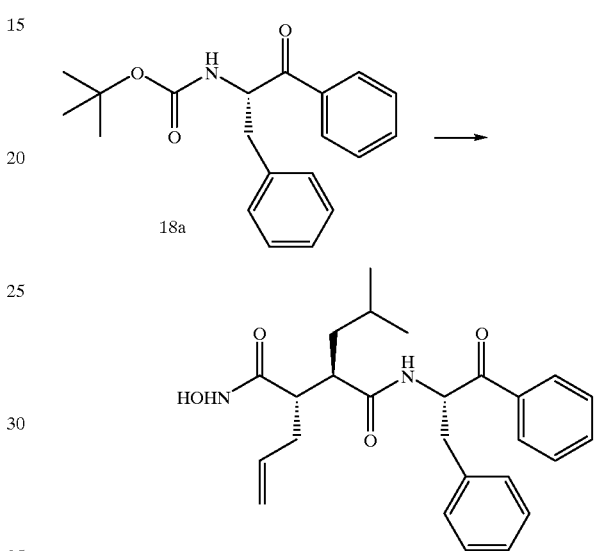

The desired compound was prepared according to the method of Examples 17B and C, except substituting 18a for 17a. mp 209–211°. 1H NMR (DMSO-d6) δ10.39 (s, 1H), 8.72 (s, 1H), 8.59–8.57 (d, 1H, J=8.5 Hz), 8/06–8.02 (d, 2H, J=8.1 Hz), 7.69–7.64 (t, 1H, J=7.1 Hz), 7.55–7.52 (t, 2H, J=8.1 Hz), 7.40–7.38 (d, 2H, J=7.4 Hz), 7.30–7.28 (m, 2H), 7.20–7.18 (m, 1H), 5.66–5.62 (m, 1H), 5.44–5.35 (m, 1H), 4.86–4.70 (m, 2H), 3.19–3.13 (dd, 1H, J=7.9, 4.1 Hz), 2.94–2.86 (m, 1H), 2.38–2.34 (m, 1H), 1.96–1.81 (m, 2H), 1.33–1.26 (m, 2H), 0.88–0.81 (m, 2H), 0.68–0.59 (m, 6H). MS (DCI/NH4) 437 (M+1). Anal. Calcd for: C$_{26}$H$_{32}$N$_2$O$_4$: C 70.57; H, 7.44; N, 6.33. Found: C, 70.60; H, 7.13; N, 6.42.

EXAMPLE 19

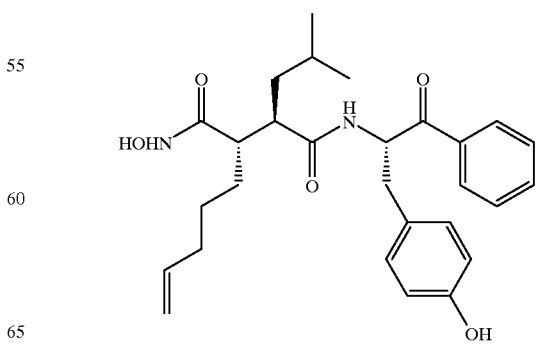

EXAMPLE 19A

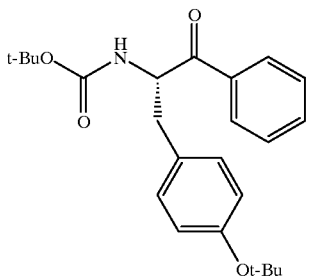
19a

The desired compound was prepared according to the method of Example 18A, except substituting N-Boc-O-tBu-L-tyrosine for N-BOC-1-phenylalanine.

EXAMPLE 19B

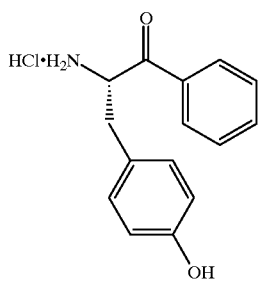
19b

A cold 0° C. solution of 19a (1.8 g, 4.7 mmol) in trifluoroacetic acid was stirred for 30 minutes. The excess TFA was removed in vacuo and the residue was taken up in 1N HCl in Et$_2$O, allowed to stir for 30 minutes, diluted with diethyl ether, and the residual solid was filtered. The extremely hygroscopic solid was dried in a vacuum oven for several hours and then was dried under high vacuum for 16 hours to give 19b (0.48 g) as a hygroscopic, white HCl salt.

EXAMPLE 19C

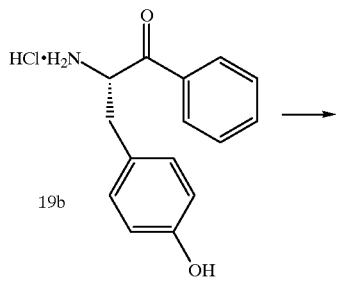

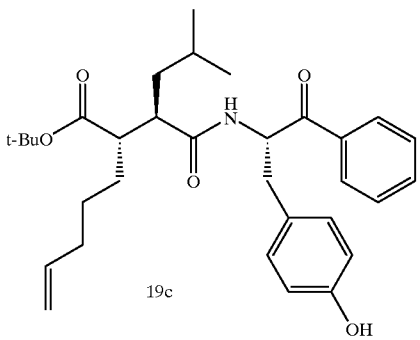
19c

To a 0° C. solution of succinate ester 3 (1.5 g, 5 mmol) in 20 mL of methylene chloride was added HOBT (0.81 g, 6 mmol) and EDCI (1.17 g, 6 mmol). The suspension became a clear solution after 10 minutes and was allowed to stir for 4 hours total. The solution was diluted with methylene chloride and the organics were washed with water (3×) and brine and concentrated in vacuo. The crude HOBT ester was dissolved in DMF (10 mL) and added to a solution of 19b (1.7 g, 6 mmol) and NMM (1.2 g, 10 mmol) in 10 mL of DMF. The reaction stirred for 3 days and then was diluted with ethyl acetate and the organic layer was washed with water (3×) and brine, dried (Na$_2$SO$_4$) and concentrated in vacuo. Flash chromatography (gradient elution: methanol-methylene chloride 0–2%) gave 19c (2.45 g) as a while solid.

EXAMPLE 19D

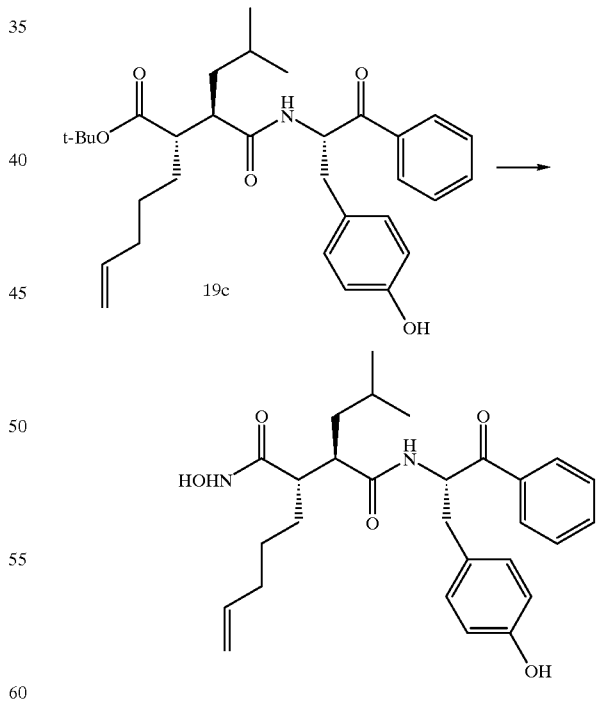

The desired compound was prepared according to the method of Examples 1E and F, except substituting 19c for 1d. mp 208–210° C. (dec). $^1$H NMR (300 MHz, DMSO-d6) δ10.42 (s, 1H), 9.15 (s, 1H), 8.71 (s, 1H), 8.49–8.47 (d, 1H, J=7.8 Hz), 7.99–7.97 (d, 2H, J=7.4 Hz), 7.63–7.60 (t, 1H, J=7.2 Hz), 7.53–7.48 (t, 2H, J=7.8 Hz), 7.13–7.10 (d, 2H, J=8.2 Hz), 6.65–6.62 (d, 2H, J=8.5 Hz), 5.73–5.64 (m, 1H), 5.49–5.48 (m, 1H), 4.95–4.86 (m, 2H), 3.01–2.95 (m, 1H), 2.77–2.69 (m, 1H), 2.36–2.34 (m, 1H), 1.89–1.68 (m, 3H), 1.28–1.18 (m, 5H), 0.82–0.58 (m, 7H). MS (DCI/NH₃) m/e 481 (M+H)⁺.

EXAMPLE 20

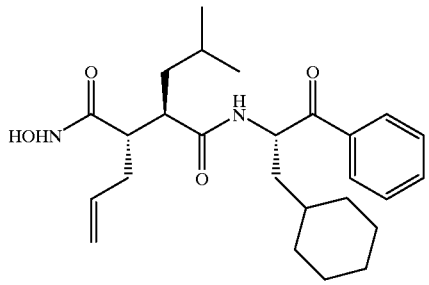

The desired compound was prepared according to the method of Example 19, except substituting N-BOC-alpha-cyclohexyl alanine for N-Boc-O-tBu-L-tyrosine. mp 209–210° C. ¹H NMR (300 MHz, DMSO-d6) δ10.47 (s, 1H), 8.76 (s, 1H), 8.54–8.52 (d, 1H, J=7.5 Hz), 7.92–7.89 (d, 2H, J=8.1 Hz), 7.66–7.60 (t, 1H, J=8.5 Hz), 7.55–7.49 (t, 2H, 7.8 Hz), 5.62–5.50 (m, 1H), 5.33–5.29 (m, 1H), 4.93–4.86 (m, 2H), 2.20–2.08 (m, 2H), 1.91–1.87 (m, 2H), 1.61–1.32 (m, 7H), 1.13–1.10 (m, 4H), 0.9–0.80 (m, 3H), 0.76–0.74 (d, 3H, J=6.4 Hz), 0.67–0.65 (d, 3H, J=6.8 Hz). MS (DCI/NH₃) m/e 443 (M+H)⁺. Anal calcd for C₂₆H₃₈N₂O₄: C, 70.55; H, 8.65; N, 6.32. Found: C, 70.21; H, 8.65; N, 6.32.

EXAMPLE 21

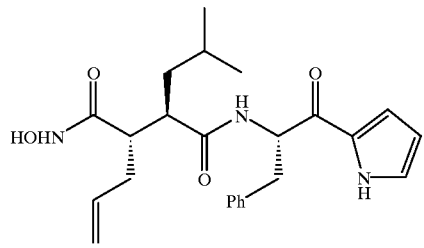

EXAMPLE 21A

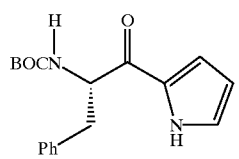

To a –40° C. solution under nitrogen of methylmagnesium bromide (9.54 ml, 3.0 M in Et₂O, 28.6 mmol) in dry toluene (20 ml) was added pyrrole (3.2 ml, 46.5 mmol) dropwise and the resulting solution was stirred at –10° C. for 10 minutes. The Grignard reagent was cannulated into a solution of BOC-L-phenylalanine-methyl ester (1.0 g, 3.58 mmol) in dry toluene (10 ml) at –65° C., the temperature was allowed to warm up to 0° C. over 4 hours, and the reaction was quenched by addition of sat. NH₄Cl solution, extracted with CH₂Cl₂ (3×), dried over Na₂SO₄, filtered and concentrated in vacuo to give 1.9 g of a crude mixture which was purified by flash chromatography(15% ethyl acetate-hexane) followed by recrystallization from Et₂O-hexanes to give 21a (677 mg) as a white solid.

EXAMPLE 21B

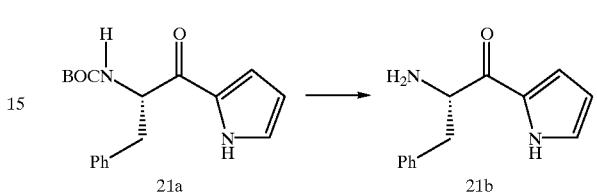

A solution of 21a (600 mg, 1.91 mmol) in 4M HCl/dioxane (8 ml) was stirred at room temperature for 50 minutes. The solvent was evaporated to give 21b (507 mg) as a purple solid which was used in the next step without further purification.

EXAMPLE 21C

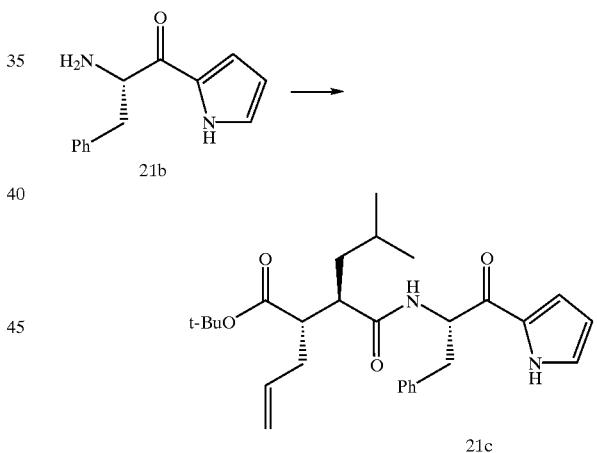

To a 0° C. solution in DMF (20 mL) of 21b (600 mg, 1.91 mmol) was added HOBT (258 mg, 1.91 mmol), NMM(630 μl, 1.91 mmol), succinate ester 2 (515.7 mg, 1.91 mmol) and EDC (366 mg, 1.91 mmol) and the reaction mixture was stirred for 20 minutes at 0° C. and for 15 hours at ambient temperature. The reaction mixture was diluted with ethyl acetate and washed with brine-H₂O (1:1). The aqueous wash was extracted with ethyl acetate (3×) and the combined organic extracts were washed with brine-H₂O (1:1), dried over Na₂SO₄, filtered and concentrated in vacuo to give a brown foam. Purification by chromatography on silica gel (20% ethyl acetate-hexanes to give 21c (797 mg) as a yellow foam.

EXAMPLE 21D

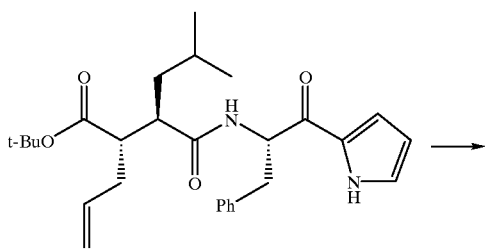

21c

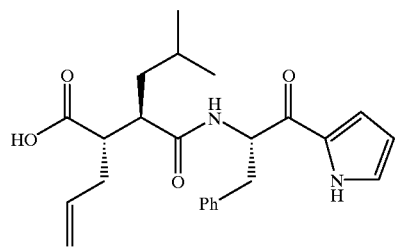

21d

A solution of 21c (781 mg, 1.67 mmol) in trifluoroacetic acid (8 ml) was stirred at ambient temperature for 50 minutes. The solvent was evaporated to give 21d (808 mg) as a yellow foam.

EXAMPLE 21E

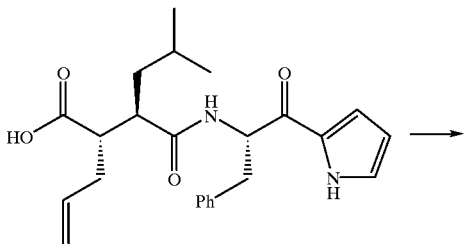

21d

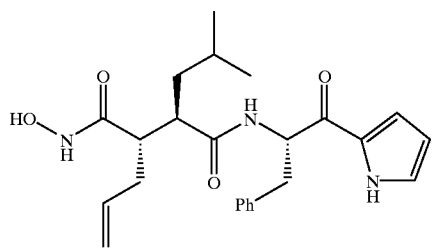

To a 0° C. solution in DMF (15 mL) under nitrogen of 21d (753 mg, 1.84 mmol) was added HOBT (273 mg, 2.02 mmol), NMM(443 µl, 4.04 mmol), TBDMSONH$_2$ (298 mg, 2.02 mmol) and EDC (387 mg, 2.02 mmol). The reaction mixture was stirred at 0° C. for 1 hour and at ambient temperature for 17 hours. The reaction mixture was diluted with ethyl acetate and washed with brine-H$_2$O (1:1). The aqueous wash was extracted with ethyl acetate (3×) and the combined organic extracts were washed with brine-H$_2$O (1:1), dried over Na$_2$SO4, filtered and concentrated in vacuo to give a yellow solid. Purification by chromatography on silica gel (10% MeOH—CH$_2$Cl$_2$) gave the desired compound (448 mg) as a white solid. mp 204–205° C. (dec). $^1$H NMR (300 MHz, DMSO-d6) δ0.65 (d, 3H, J=3 Hz), 0.77 (d, 3H, J=3 Hz), 0.83 (m, 1H), 1.13–1.38 (m, 3H), 1.77–1.98 (m, 2H), 2.41 (dt, 1H, J=3, 12 Hz), 2.88 (dd, 1H, J=3, 10.5 Hz), 3.07 (dd, 1H, J=4.5, 15 Hz), 4.66–4.84 (m, 2H), 5.23–5.46 (m, 2H), 6.22 (m, 1H), 7.09–7.40 (m, 7H), 8.44 (d, 1H, J=9 Hz), 8.685 (s, 1H), 10.36 (s, 1H), 11.88 (s, 1H). MS (DCI/NH$_3$) m/z 426 (M+H)$^+$. [α]$_d$=+19.69°(EtOH).

EXAMPLE 22

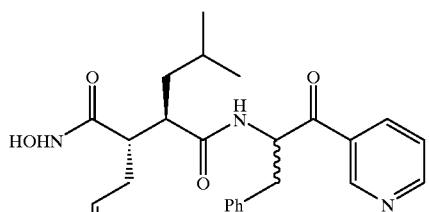

EXAMPLE 22A

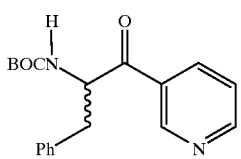

22a

To a –78° C. solution under nitrogen of n-butyl lithium (2.5M in hexanes, 21.5 ml, 53.8 mmol) in ether (180 ml) was added 3-bromopyridine (5.18 ml, 53.8 mmol) dropwise and the reaction mixture was stirred for 1 hour. A solution of BOC-L-phenylalanine methyl ester (6.0 g, 21.5 mmol) in ether (25 ml) was added and the reaction mixture was stirred at –78° C. for 3 hours and 0° C. for two hours. The reaction mixture was poured onto water, extracted with CH$_2$Cl$_2$ (3×), dried over Na$_2$SO$_4$, filtered and concentrated in vacuo to give an orange oil which was purified by flash chromatography (30% ethyl acetate-hexanes) to give 22a (1.2 g) as a yellow oil.

EXAMPLE 22B

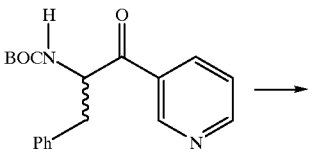

22a

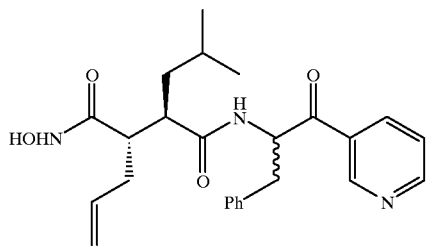

The desired compound was prepared according to the method of Examples 21B–E, except substituting 22a for 21a.

mp 196.3–197.7° C. ¹H-NMR (300 MHz, DMSO-d6) δ0.49–0.62 (m, 6H), 0.69–0.82 (m, 2H ), 1.04–1.28 (m, 2H), 1.66–1.80 (m, 1H), 1.825–1.97 (m, 1H), 2.23–2.35 (m, 1H), 2.84–2.98 (m, 1H), 3.08–3.21 (m, 1H), 4.62–4.84 (m, 2H), 5.24–5.63 (m, 2H), 7.09–7.38 (m, 6H), 7.49–7.57 (m, 1H), 8.26–8.37 (1H), 8.61–8.78 (3H), 9.07–9.156 (1H). MS (DCI/NH₃) m/z 438 (M+H)⁺. α]$_d$=–18.86° (EtOH).

EXAMPLE 23

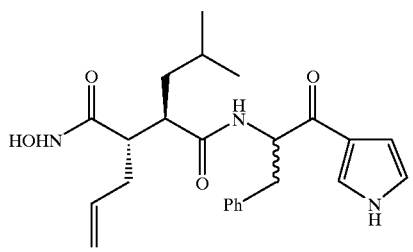

EXAMPLE 23A

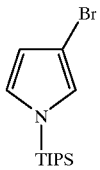

To a –78° C. solution under nitrogen of 1-triisopropylsilylpyrrole (2.8 g, 12.6 mmol) in THF (30 ml) was added NBS (2.23 g, 12.6 mmol) via a solid addition funnel. The reaction mixture was stirred at –78° C. for 1 hour and then was warmed to ambient temperature over 1 hour. The reaction mixture was concentrated, carbon tetrachloride was added to precipitate the succinimide and the solid was filtered and washed with carbon tetrachloride. The filtrate was concentrated, and the crude product was purified by flash chromatography (hexanes) to afford 3-bromo-1-triisopropylsilylpyrrole (3.18 g) as a colorless oil.

EXAMPLE 23B

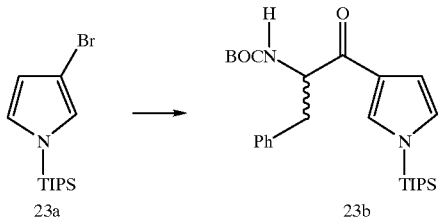

To a –78° C. solution under nitrogen of 3-bromo-1-(triisopropylsilyl-pyrrole (3.18 g, 10.5 mmol) in dry THF (50 ml) was added n-BuLi (1.6 M, 6.56 ml, 10.5 mmol) and the reaction mixture was stirred for 0.5 hours. A solution of BOC-L-phenylalanine methyl ester (1.25 g, 4.2 mmol) in dry THF (2 ml) was then added and the resulting mixture was stirred at –78° C. for 1.5 hours. The reaction mixture was poured onto water, extracted with CH₂Cl₂ (3×), dried over Na₂SO₄, filtered, and concentrated in vacuo. Chromatography on silica gel (10% ethyl acetate-hexanes) provided 23b (268 mg) as a light yellow oil.

EXAMPLE 23C

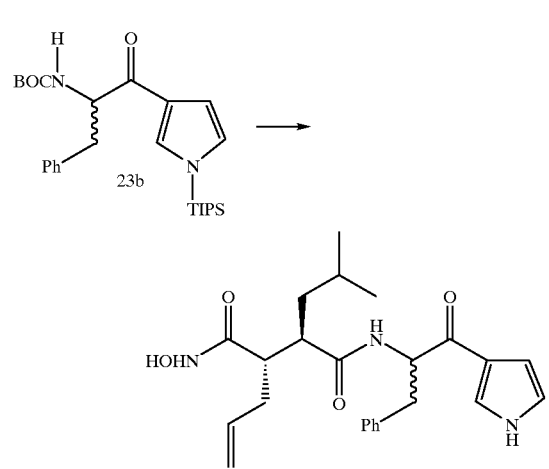

The desired compound was prepared according to the method of Examples 21B–E, except substituting 23b for 21a. ¹H NMR (300 MHz, DMSO-d6) δ0.53–0.88 (7H), 1.06–1.36 (m, 2H), 1.73–2.13 (m, 2H), 2.32–2.46 (m, 1H), 2.70–2.91 (m, 1H), 2.98–3.08 (m, 1H ), 4.65–4.85 (m, 2H), 5.18–5.54 (m, 2H), 6.54 (1H), 6.85 (1H), 7.09–7.40 (m, 5H), 7.75 (1H), 8.34–8.54 (1H), 8.70 (s, 1H). MS (DCI/NH₃) m/z 426 (M+H)⁺.

EXAMPLE 24

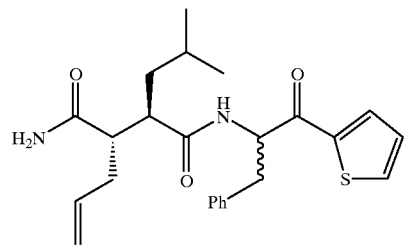

EXAMPLE 24A

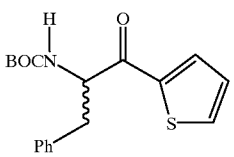

To a –78° C. solution under nitrogen of BOC-L- phenylalanine methyl ester (2.0 g, 7.16 mmol) in dry THF (80 ml) was added 2-thienyllithium (17.9 ml, 17.9 mmol) and the reaction mixture stirred for 1 hour. The reaction mixture was poured onto water, extracted with CH₂Cl₂ (3×), dried over Na₂SO₄, filtered and concentrated in vacuo to give an orange oil. Purification by chromatography on silica gel (0.5% acetone-CH₂Cl₂) gave 24a (882 mg) as a yellow solid.

EXAMPLE 24B

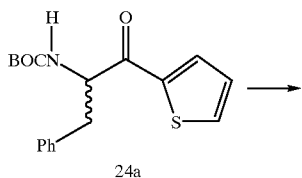

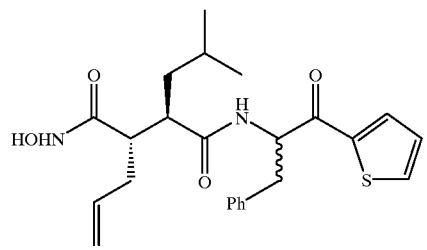

The desired compound was prepared according to the method of Examples 21B–E except substituting 24a for 21a. ¹H NMR(300 MHz, DMSO-d6) δ0.54–0.87 (m, 7H), 0.95–1.35 (m, 2H), 1.68–2.11 (m, 2.5H), 2.32–2.47 (m, 0.5H), 2.83–3.15 (m, 2H), 4.63–4.85 (m, 2H), 5.29–5.52 (m, 2H), 7.11–7.40 (m, 6H), 8.02–8.20 (2H), 8.58–8.75 (1H), 8.73 (s, 1H). MS (DCI/NH$_3$), m/z 443 (M+H)$^+$.

EXAMPLE 25

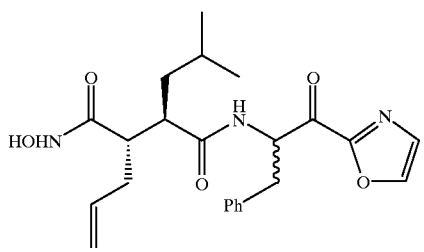

EXAMPLE 25A

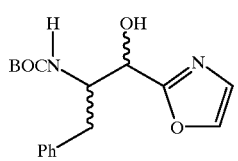

To a –70° C. solution under nitrogen of oxazole (3.36 g, 48.8 mmol) in THF (80 ml) at was added n-BuLi (30.5 ml, 48.8 mmol) and the mixture was stiffed at –70° C. for 20 minutes. A solution of N-BOC-phenylalaninal (4.86 g, 19.5 mmol) in THF (20 ml) was then added and the mixture was stirred at –50–-70° C. for 6 hours. The reaction was quenched with H$_2$O, extracted with CH$_2$Cl$_2$ (3×), dried over Na$_2$SO$_4$, filtered and concentrated in vacuo. Chromatography on silica gel (40% ethyl acetate-hexanes) provided 25a (1.12 g).

EXAMPLE 25B

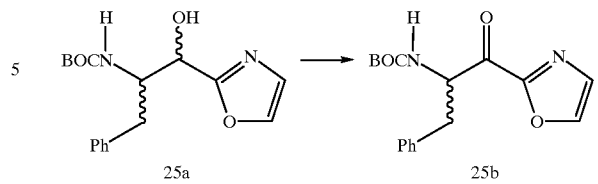

To a 0° C. solution of 25a (969 mg, 3.05 mmol) in CH$_2$Cl$_2$ (60 ml) was added KBr/H$_2$O (36.3 mg, 613 μl) and 2,2,6,6-tetramethyl-1-piperidinyloxy, free radical (4.76 mg, 0.0305 mmol). In another vial, NaOCl solution (10.9 ml) was adjusted to pH 8 with saturated aqueous NaHCO$_3$ solution, and the resulting solution was added to the 25a solution and the reaction mixture was stirred at 0° C. for 5 hours. The reaction mixture was poured into H$_2$O-brine, extracted with CH$_2$Cl$_2$ (3×), dried over Na$_2$SO$_4$, filtered and concentrated in vacuo. Chromatography on silica gel (30%–40% ethyl acetate-hexanes) gave 25b (731 mg).

EXAMPLE 25C

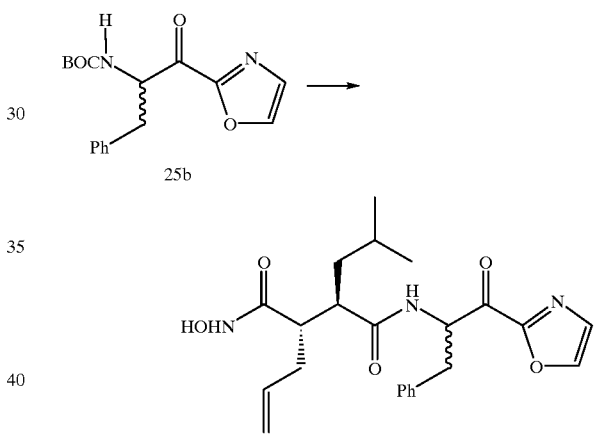

The desired compound was prepared according to the method of Examples 21B–E except substituting 25b for 21a. ¹H NMR (300 MHz, DMSO-d6) δ0.54–0.90 (m, 7H), 1.14–1.39 (m, 3H ), 1.75–2.06 (m, 2H), 2.71–2.82 (m, 1H), 3.11–3.22 (m, 1H), 4.64–4.91 (m, 2H), 5.29–5.42 (m, 2H), 7.12–7.41 (m, 5H), 8.53 (d, 1H, J=7.5 Hz), 8.60–8.65 (1H), 8.74 (s, 1H). 9.02–9.08 (1H), 10.36–10.48 (1H). MS (DCI/NH$_3$) m/z 428 (M+H)$^+$.

EXAMPLE 26

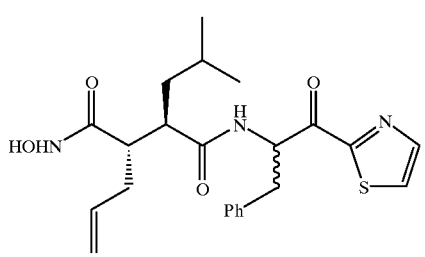

EXAMPLE 26A

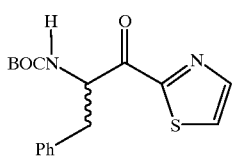

26a

To a −78° C. solution under nitrogen of thiazole (1.1 ml, 15.8 mmol) in THF (80 ml) was added n-butyl lithium (1.6M in hexanes, 9.88 ml, 15.8 mmol) and the reaction mixture was stirred for 0.5 hours. A solution of BOC-L-phenylalanine methyl ester (2.0 g, 7.17 mmol) in THF (5 ml) was added and the mixture was stirred at −78° C. for 30 minutes. The reaction mixture was poured into water, extracted with $CH_2Cl_2$ (3×), dried over $Na_2SO_4$, filtered, and concentrated in vacuo. Chromatography on silica gel (20% ethyl acetate-hexanes) gave 26a (1.95 g) as a yellow solid.

EXAMPLE 26B

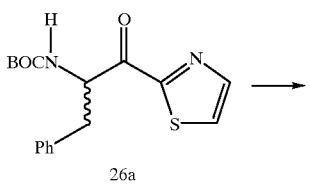

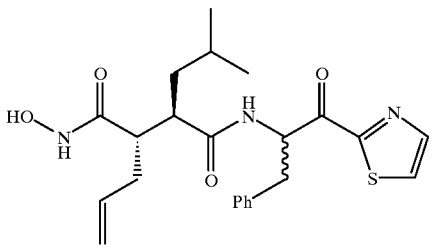

The desired compound was prepared according to the method of Examples 21B–E except substituting 26a for 21a. $^1$H NMR (300 MHz, DMSO-d6) δ0.55–0.92 (m, 7H), 1.18–1.40 (m, 2H), 1.80–2.29 (m, 3H), 2.75–2.90 (m, 1H), 4.66–4.95 (m, 2H), 5.30–5.76 (m, 2H), 7.13–7.38 (m, 5H), 8.22–8.30 (2H), 8.58–8.75 (2H). MS (DCI/NH$_3$) m/z 444 (M+H)$^+$.

EXAMPLE 27

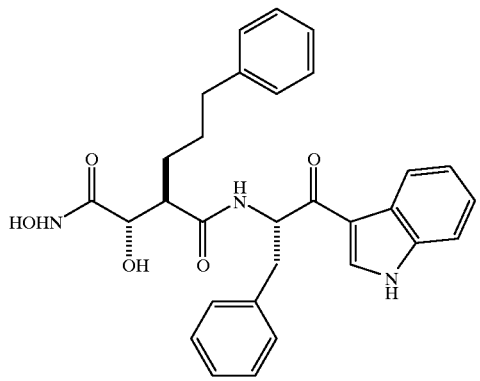

EXAMPLE 27A

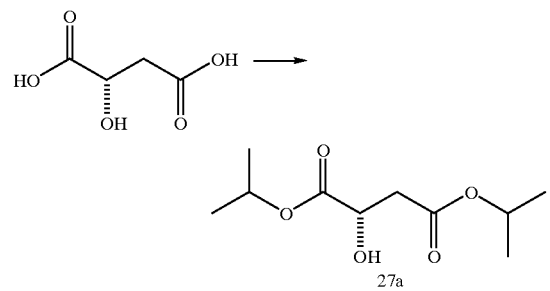

Malic acid (53.2 g, 0.397 mol) was dissolved in 400 mL of HCl saturated 2-propanol and the solution was heated at reflux for 22 hours. The solution was reduced in volume by rotary evaporation, diluted with EtOAc (1 L), and extracted twice with saturated aqueous $Na_2CO_3$. The organics were dried over $MgSO_4$ and concentrated to give diiso-propyl malate 27a (67 g).

EXAMPLE 27B

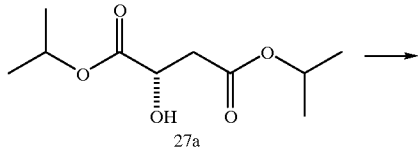

27a

27b

Diiso-propyl malate (27a, 25.6 g, 117 mmol) was added slowly to a 1 M solution of LDA in THF (235 mL, 235 mmol) at −78° C. The solution was allowed to slowly warm to −50° C. over 2 hours, and then was recooled to −78° C. Cinnamyl bromide (25.0 g, 127 mmol) in THF (50 mL) was added dropwise, and the solution was stirred at −78° C. for 15 hours. The dry ice bath was removed and the reaction was quenched with 1M HCl. The solution was diluted with ether and extracted twice with 1M HCl. After drying (Na$_2$SO$_4$) and solvent removal, the crude material was chromatographed on silica gel (15% ether-hexanes) to give 27b as a 10:1 mixture of diastereomers (9.5 g).

EXAMPLE 27C

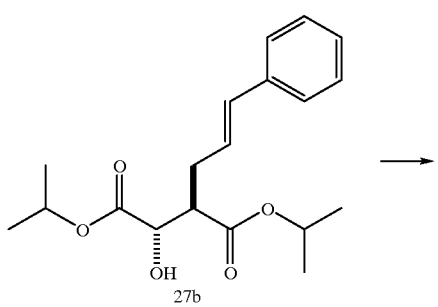
27b

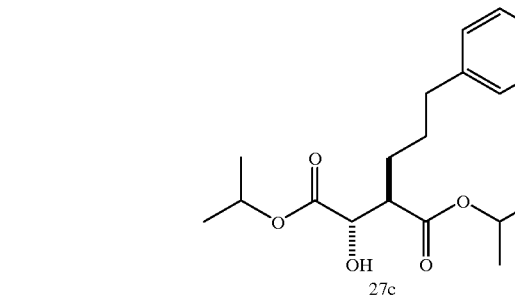
27c

A mixture of 27b (9.29 g) and 10% Pd/C (0.45 g) and were placed in a Parr shaker containing 150 mL methanol, and exposed to 4 atm pressure of hydrogen for 18 hours. Filtration and solvent removal provided 27c as a yellow liquid (9.39 g).

EXAMPLE 27D

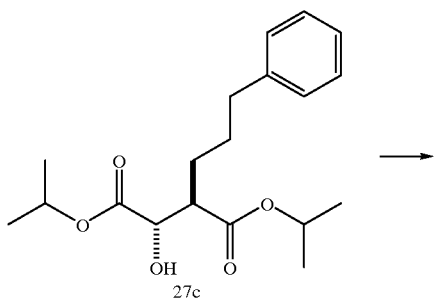
27c

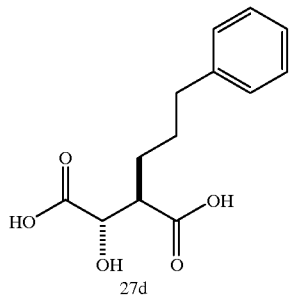
27d

A solution of 27c (9.39 g, 27.9 mmol) in 20 mL dioxane was treated with 3 M KOH (30 mL) and stirred overnight at 90° C. The solution was poured over ice and acidified to pH 3 with concentrated HCl. The reaction mixture was extracted twice with EtOAc, and the organics were dried over MgSO$_4$. Solvent removal gave 27d as a yellow liquid.

EXAMPLE 27E

27d

27e

To a solution of 27d (7.0 g, 28 mmol) DMF (50 mL) and 2,2-dimethoxypropane (180 mL) was added Dowex-50 resin and the mixture was stirred at ambient temp for 3 days. The resin was filtered off and the solution concentrated to give a DMF solution of 27e which was used as is in the next step.

EXAMPLE 27F

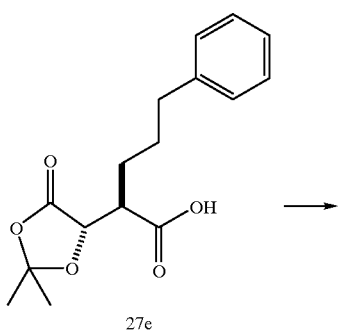

27e

↓

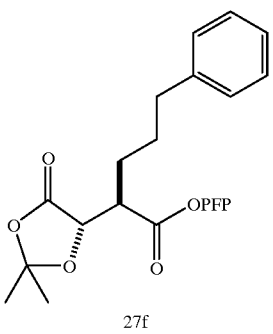

27f

Crude acid 27e (theoretical yield 28 mmol) with residual DMF was diluted with CH$_2$Cl$_2$ (110 mL) and cooled to 0° C. Pentafluorophenol (8.33 g, 45 mmol) was added, followed by EDCI (6.49 g, 33.8 mmol). The mixture was stirred at 0° C. for 2.5 hours, then extracted successively with saturated aqueous Na$_2$CO$_3$ and brine. The organic phase was reduced in volume in vacuo, diluted with ethyl acetate, washed three times with brine, dried over Na$_2$SO$_4$, filtered, and concentrated in vacuo. Chromatography on silica gel (gradient elution 10-15-20% ether-hexanes) gave 27f (8.88 g) as a 7:4 mixture of diastereomers.

EXAMPLE 27G

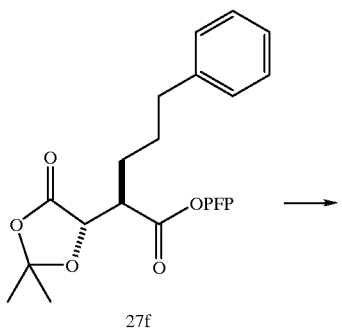

27f

→

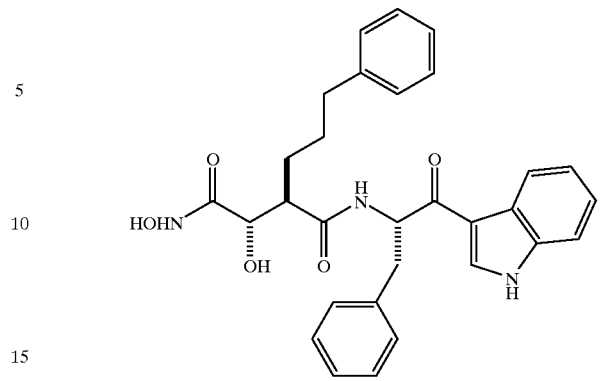

The desired compound was prepared according to the method of Example 10, except substituting 27f for 10a. mp 111°113° C. $^1$H NMR (300 MHz, DMSO-d6) δ1.23 (m, 3H), 1.37 (m, 1H), 2.25 (m, 1H), 2.38 (m, 1H), 2.62 (m, 1H), 2.90 (dd, 1H, J=6.6, 14.0 Hz), 3.21 (dd, 1H, J=7.3, 13.6 Hz), 3.84 (dd, 1H, J=6.6, 8.5 Hz), 5.24 (d, 1H, J=6.6 Hz), 5.44 (q, 1H, J=8.1 Hz), 6.77 (dd, 2H, J=1.5, 8.2 Hz), 6.96 (m, 3H), 7.15 (m, 3H), 7.22 (m, 6H), 7.47 (dd, 1H, J=1.9, 5.9 Hz), 8.19 (dd, 1H, J=2.2, 5.9 Hz), 8.32 (d, 1H, J=3.0 Hz), 8.52 (1H, J=8.4 Hz), 8.83 (bds, 1H), 10.63 (bds, 1H), 11.94 (d, 1H, J=2.6 Hz). $^{13}$C NMR (CD$_3$OD) δ30.03, 30.11, 36.55, 39.80, 50.99, 57.05, 73.04, 112.98, 116.67, 122.89, 123.37, 124.49, 126.50, 127.15, 127.50, 129.12, 129.20, 129.28, 130.45, 135.53, 138.43, 138.69, 143.14, 171.52, 175.07, 194.40. MS (APCI) m/e 514 (M+H)$^+$, 453. Anal calcd for C$_{30}$H$_{31}$N$_3$O$_5$. 0.8 H$_2$O: C, 68.24; H, 6.22; N, 7.96. Found: C, 68.40; H, 6.27; N, 7.56. [α]$_d$=−129 (CH$_3$OH, c=0.02).

EXAMPLE 28

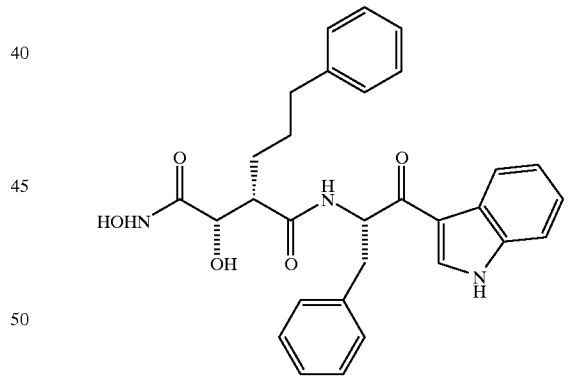

The desired compound was isolated in the purification of the compound of Example 27. mp 116–118° C. $^1$H NMR (300 MHz, DMSO-d6) δ1.18 (m, 2H), 1.28 (m, 1H), 1.53 (m, 1H), 2.01 (m, 2H), 2.70 (m, 1H), 2.89 (dd, 1H, J=4.1, 13.3 Hz), 3.12 (dd, 1H, J=4.8, 13.3 Hz), 3.97 (t, 1H, J=4.9 Hz), 5.21 (d, 1H, J=5.2 Hz), 5.38 (m, 1H), 7.04 (d, 2H, J=7.0 Hz), 7.1–7.3 (m, 10H), 7.47 (m, 1H), 8.20 (dd, 1H, J=2.3, 5.6 Hz), 8.41 (d, 1H, J=2.9 Hz), 8.51 (d, 1H, J=8.5 Hz), 8.63 (bds, 1H), 10.37 (bds, 1H), 11.97 (bds, 1H). MS (APCI) m/e 514 (M+H)$^+$, 453. Anal calcd for C$_{30}$H$_{31}$N$_3$O$_5$.0.5 H$_2$O: C, 68.95; H, 6.17; N, 8.04. Found: C, 69.11; H, 6.17; N, 7.92. [α]$_d$=−22.3 (CH$_3$OH, c=0.01).

EXAMPLE 29

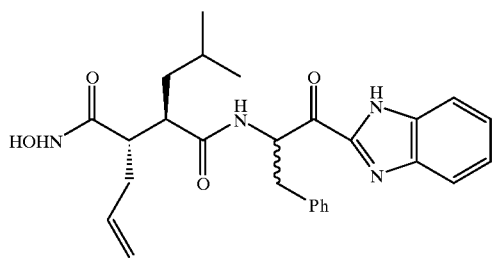

EXAMPLE 29A

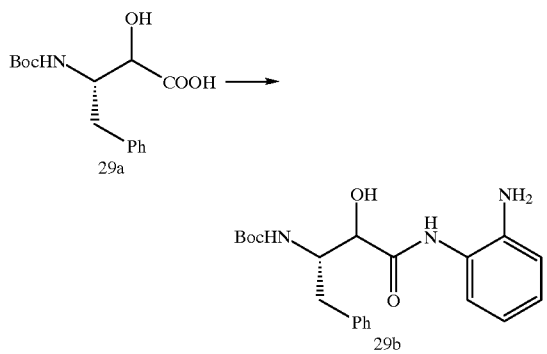

To a solution of 29a (0.32 g, 1.08 mmol) in DMF (6.0 mL) was added EDC (0.23 g, 1.19 mmol), HOBT (0.16 g, 1.19 mmol), NMM (0.13 mL, 1,19 mmol) and 1,2-phenethyldiamine (0.12 g, 1.13 mmol) and the reaction mixture was stirred for 6 hours, the reaction mixture was partitioned between ethyl acetate and brine. The aqueous layer was separated and extracted twice with ethyl acetate. The ethyl acetate extracts were combined, washed with brine, dried over MgSO$_4$, filtered and evaporated to dryness. The crude 29b was used for next reaction without purification.

EXAMPLE 29B

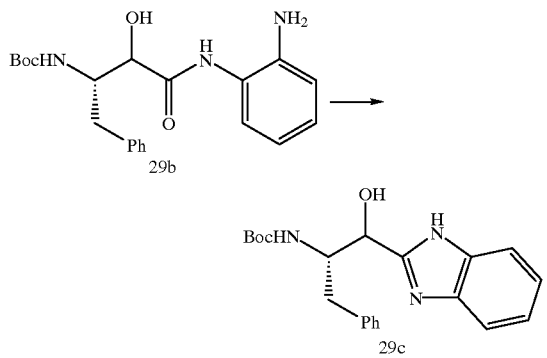

A mixture of 29b and camphorsulfonic acid (12 mg, mmol) in toluene (20 mL) was heated at 80° C. for 4 hours. The reaction mixture was evaporated to a small volume and partitioned between CH$_2$Cl$_2$, brine and saturated aqueous NaHCO$_3$. The aqueous layer was extracted with CH$_2$Cl$_2$. The CH$_2$Cl$_2$ layers were combined, dried (MgSO$_4$), filtered and evaporated to dryness. Flash chromatography (40%–80% ethyl acetate-hexanes) gave 29c (261 mg) as white crystals.

EXAMPLE 29C

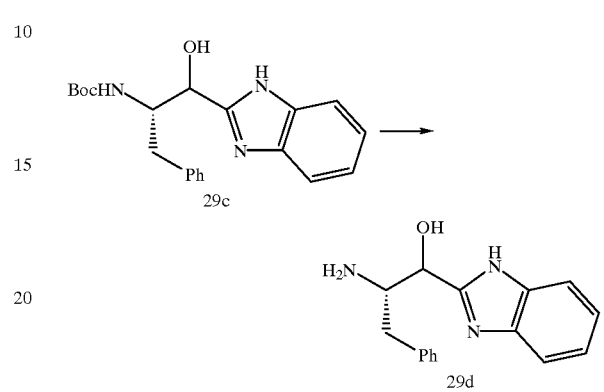

A mixture of 29c (255 mg, 0.69 mmol) and trifluoroacetic acid (1.5 mL) was stirred for 30 minutes, and then was evaporated to dryness. Residual trifluoroacetic was removed by azeotropic evaporation with toluene to give 29d as brownish crystals which was used without further purification.

EXAMPLE 29D

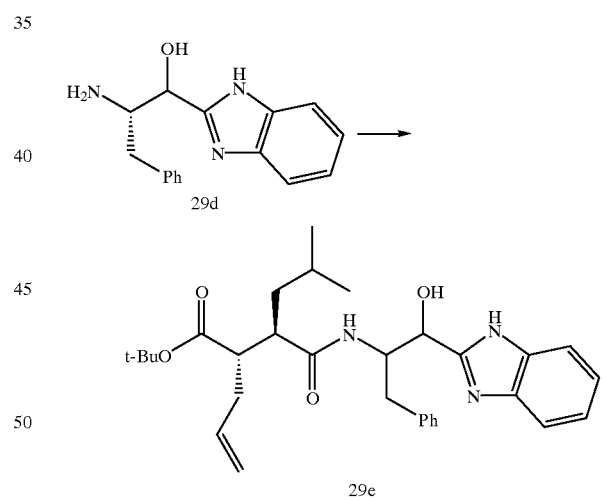

To a solution of succinate ester 2 (0.828 mmol) in DMF (2 mL) was added EDC (159 mg, 0.828 mmol), HOBT(112 mg, 0.828 mmol) and NMM (0.19 mL, 1.73 mmol). The reaction mixture was stirred at room temperature for 10 minutes and a solution of 29d (0.69 mmol) in DMF (2 mL) was added. The reaction mixture was stirred for 10 hours and then was partitioned between ethyl acetate and brine. The aqueous layer was separated and extracted twice with ethyl acetate. The combined ethyl acetate extracts were washed with brine, dried (MgSO$_4$), filtered and evaporated to dryness. Chromatography on silica gel (20–40% ethyl acetate-hexanes) gave 29e (156 mg) as yellow crystals.

EXAMPLE 29E

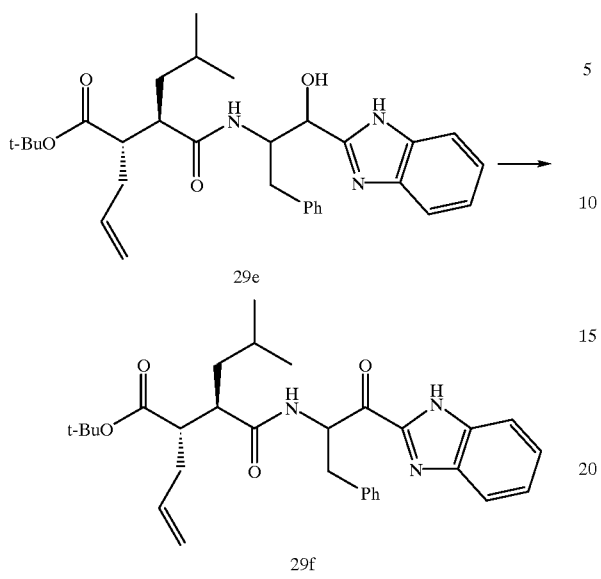

The desired compound was prepared according to the method of Example 25B, except substituting 29e for 25a.

EXAMPLE 29F

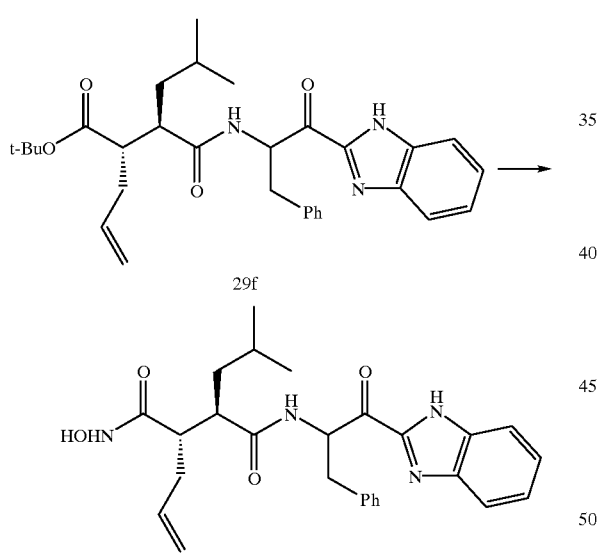

The desired compound was prepared according to the method of Examples 21D and E, except substituting 29f for 21c. Mixture of two stereoisomers: mp: 159.5–161.0° C. (dec). $^1$H NMR (300 MHz, DMSO-d6) δ0.58 (d, 3H, J=5.6 Hz), 0.65 (d, 3H, J=5.6 Hz), 0.72 (d, 3H, J=6.2 Hz), 0.87 (d, 3H, J=6.2 Hz), 0.79–0.89 (m, 1H), 0.70–0.89 (m, 1H), 1.20–1.30 (m, 2H), 1.30–1.42 (m, 2H), 1.83–2.17 (m, 3H), 1.83–2.17 (m, 3H), 2.78–2.87 (m, 1H), 2.78–2.87 (m, 1H), 3.40 (m, 2H), 3.45 (m, 2H), 4.70 (dd, 1H, J=16.5, 1.6 Hz), 4.81 (dd, 1H, J=10, 1.6 Hz), 4.88 (d, 1H, J=10.5 Hz), 4.89 (d, 1H, J=15.8 Hz), 5.38 (m, 1H), 5.55 (m, 1H), 5.79 (m, 1H), 5.84 (m, 1H), 7.21 (m, 2H), 7.26–7.32 (m, 5H), 7.41 (m, 2H), 7.36–7.43 (m, 5H), 7.58 (d, 2H, J=8.4 Hz), 7.89 (d, 2H, J=8.7 Hz), 8.61 (d, 1H, J=8.4 Hz), 8.70 (s, 1H), J=8.2 Hz), 8.72 (s, 1H), 8.72 (s, 1H), 10.40 (d, 1H, J=1.2 Hz), 10.42 (d, 1H, J=1.2 Hz), 13.52 (s, 1H), 13.52 (s, 1H). MS (DCI—NH3) m/e 477 (M+H)+, 433. Anal calcd for $C_{27}H_{32}N_4O_4$: C, 66.78; H, 6.84; N, 11.53. Found: C, 66.6; H, 6.69; N, 11.25.

EXAMPLE 30

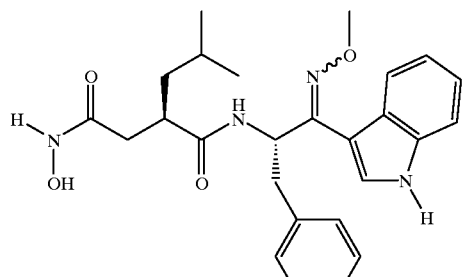

EXAMPLE 30A

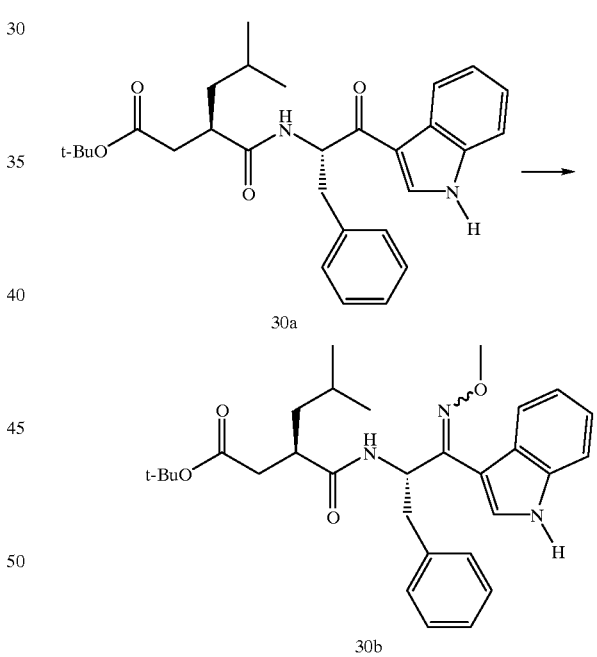

To a solution of 30a (2.45 g, 5.15×10$^{-3}$ mol), prepared by coupling of 2c and R-2-(i-butyl)-succinic acid-4-t-butyl ester according to the method of Example 2C, in pyridine (50 mL) was added O-methylhydroxylamine hydrochloride (0.80 g, 1.00×10$^{-2}$ mol) in one portion and the mixture was heated at 80° C. for 3 days. The pyridine was removed in vacuo. The residue was taken up in CH$_2$Cl$_2$ and the solvent was removed in vacuo. Flash chromatography (CH$_2$Cl$_2$) gave 30b as a mixture of oxime diastereomers.

EXAMPLE 30B

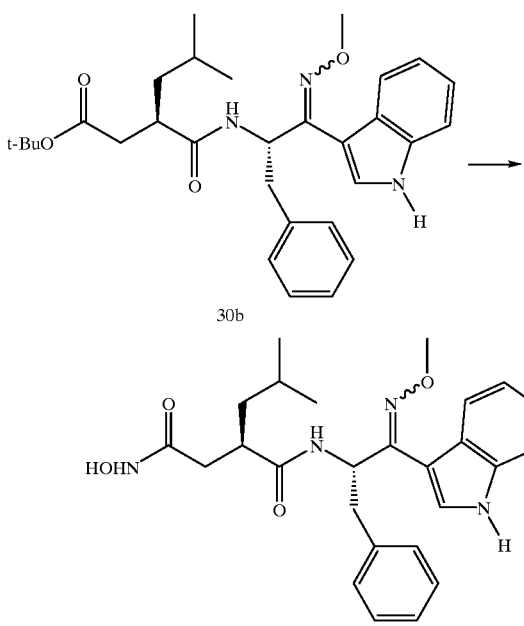

The desired compound was prepared according to the method of Examples 5A and B, except substituting 30b for the compound of Example 4. ¹H NMR (300 MHz, DMSO-d6) δ11.43 (s, 1H), 10.37 (s, 1H), 8.73 (s, 1H), 8.36 (d, 1H, J=8.1 Hz), 8.08 (d, 1H, J=7.7 Hz), 7.92 (d, 1H, J=2.6 Hz), 7.41–6.98 (m, 8H), 5.60–5.49 (m, 1H), 3.90 (s, 3H), 3.20–2.98 (m, 2H), 2.81–2.69 (m, 1H), 1.87–1.77 (m, 2H), 1.29–1.17 (m, 1H), 1.02–0.74 (m, 2H), 0.58–0.49 (m, 6H). MS (DCI—NH₃) m/e 465 (M+H)⁺. Anal calcd for $C_{26}H_{32}N_4O_4 \cdot 0.25 H_2O$: C, 66.57; H, 6.98; N, 11.94. Found: C, 66.72; H, 7.11; N, 11.85.

EXAMPLE 31

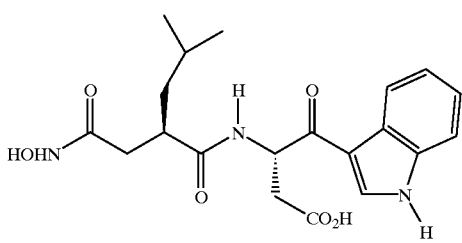

EXAMPLE 31A

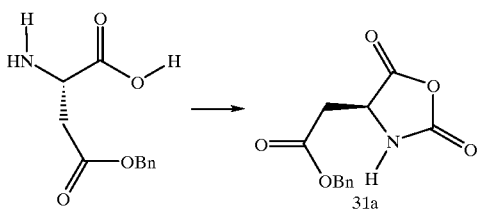

To a suspension in THF (25 mL) of OBn-Asp (1 g, 4.48 mmol) and activated charcoal (25 mg) was added diphosp-gene (0.416 mL, 3.45 mmol) via syringe at ambient temperature and the reaction mixture was heated at 55° C. for 1.5 hours. The solution was then filtered through celite, the filter cake was washed with EtOAc, and the solvent was removed in vacuo. The resulting solid was recrystallized (EtOAc-Hexane) to give the desired product in 55% yield.

EXAMPLE 31B

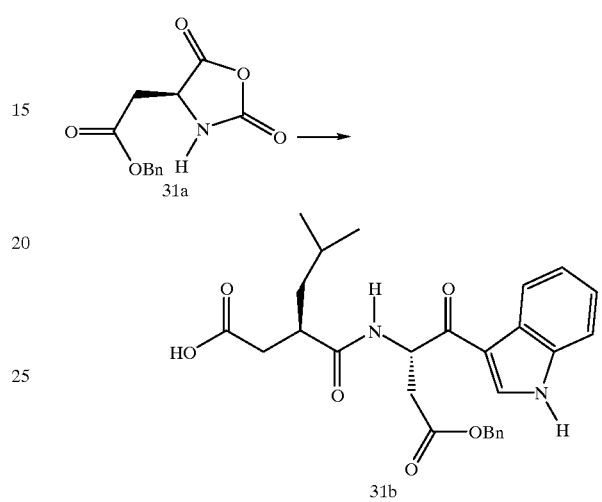

The desired compound was prepared according to the method of Examples 2A and B, except substituting 31a for 2b and substituting for R-2-(i-butyl)-succinic acid-4-t-butyl estersuccinate ester 4.

EXAMPLE 31C

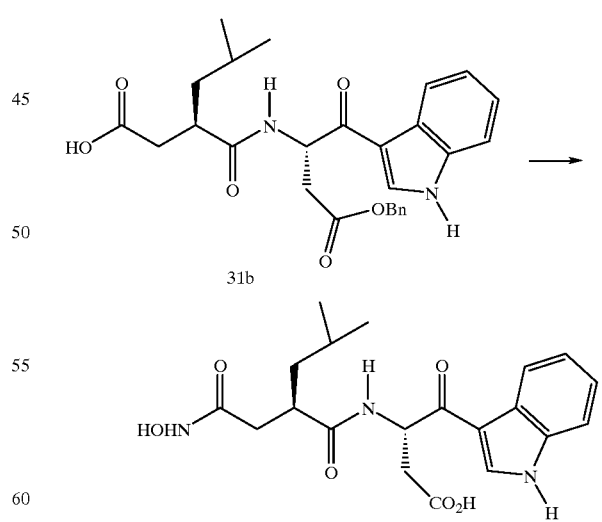

The desired compound was prepared according to the method of Example 5, except substituting 3b for the compound of Example 4.

EXAMPLE 32

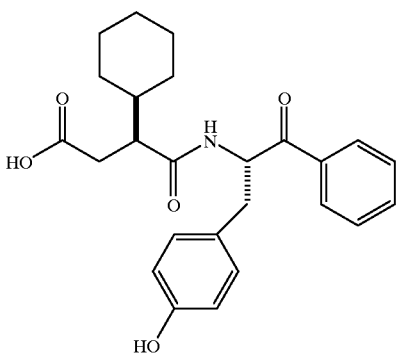

EXAMPLE 32A

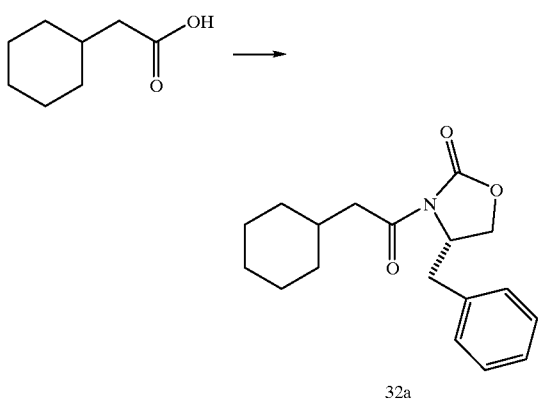

Cyclohexylacetic acid (25 g, 0.176 mol) was dissolved in 50 mL thionyl chloride, and the solution was heated at reflux for 1 hour. The solution was concentrated in vacuo and placed under vacuum for 1 hour. The acid chloride was then added to a −78° C. solution in THF (450 mL) of 1-lithio 2-(S)-benzyloxazolidinone (0.158 mol). After 10 minutes, the dry ice bath was removed, and after a further 30 minutes, the mixture was quenched with aqueous NH₄Cl solution. The solution was extracted with 1 M NaOH and washed with pH 7 buffer solution. The organic phase was dried over MgSO₄, filtered and concentrated in vacuo to give 32a as a white solid (42 g) which was used without further purification.

EXAMPLE 32B

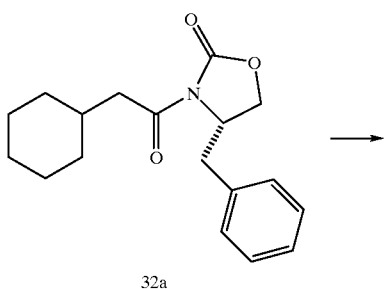

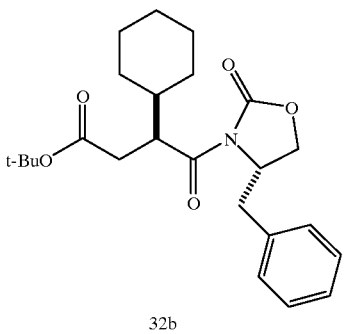

To a −78° C. solution in THF (420 mL) of acyl oxazolidinone 32a (42 g, 140 mmol) was added sodium hexamethyldisilazide (140 mL of a 1 M solution in THF, 140 mmol) dropwise over 40 minutes. After 30 minutes, a solution of tert-butyl bromoacetate (23 mL, 156 mmol) in 70 mL THF was added dropwise over 30 minutes. One hour after the addition was begun, the dry ice bath was removed and replaced with an ice bath. After 2 hours at 0° C., the reaction was quenched with aqueous NH₄Cl. The solution was concentrated, diluted with EtOAc and extracted twice with aqueous NH₄Cl. After drying (Na₂SO₄) and solvent removal, the crude material was recrystallized from 3:1 hexanes-EtOAc to give 32b (31.8 g) as white needles, mp 141–142° C. Flash chromatography of the mother liquors provided a further 2.60 g product.

EXAMPLE 32C

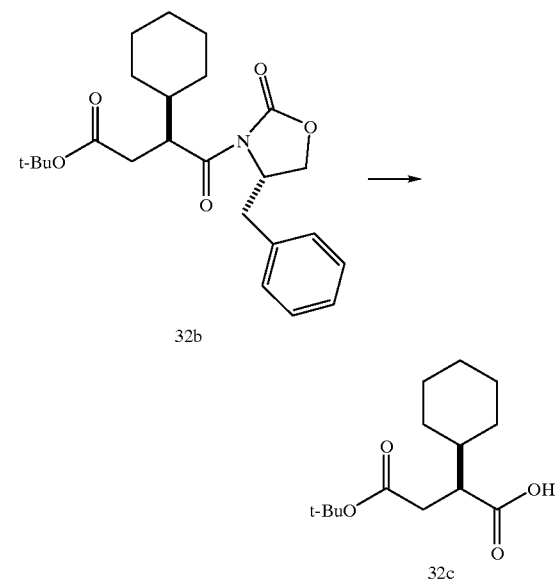

To a 0° C. solution of acyloxazolidinone 32b (34.4 g, 83 mmol) in 360 mL THF was added 30 mL water and 33 ml 30% hydrogen peroxide, followed by a solution of LiOH (5.28 g, 126 mmol) in 120 mL water. After 6.5 hours, the peroxides were quenched with NaHSO₃ (300 mmol), then KOH (300 mmol) was added. The solution volume was reduced in vacuo and the pH adjusted to 9 with 50% aqueous NaOH. The solution was extracted twice with methylene chloride, then acidified to pH3 with concentrated HCl. The aqueous phase was extracted with ethyl acetate. The organic phase was dried over Na$_2$SO$_4$, filtered and concentrated in vacuo to give 32c as a slightly yellow oil (10.4 g).

EXAMPLE 32D

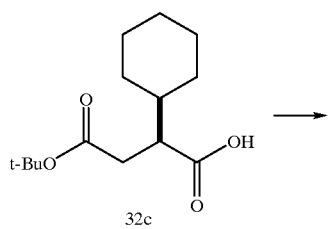

32c

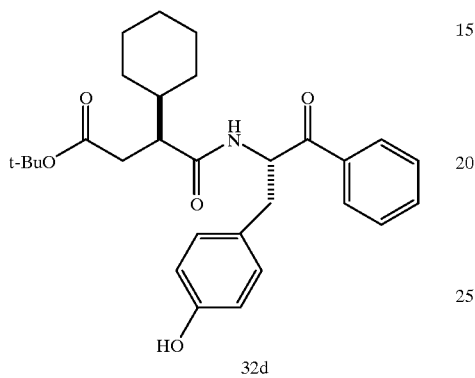

32d

The desired compound was prepared according to the method of Example 19C, except substituting 32c for succinate ester 3.

EXAMPLE 32E

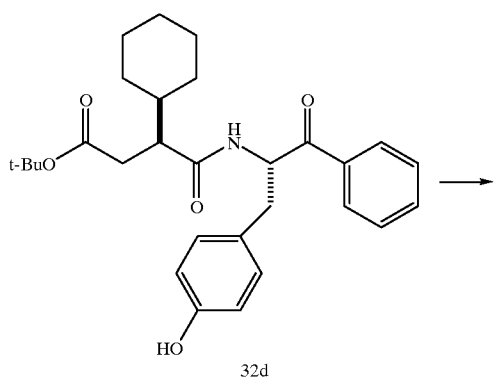

32d

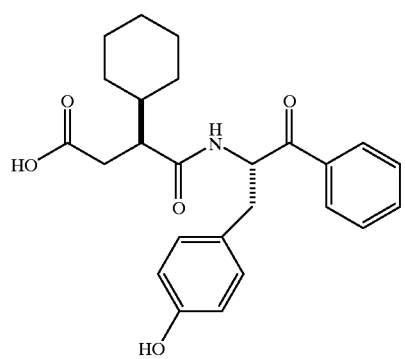

A solution of 32d (1.37 g, 2.86 mmol) in 30 mL HCl saturated acetic acid was stirred for 4 hours at ambient temperature. The reaction mixture was concentrated in vacuo and the residue was azeotroped twice with toluene. Vacuum drying provided the desired compound as a white foam. $^1$H NMR (300 MHz, CD$_3$OD) δ0.87 (m, 2H), 1.08 (m, 2H), 1.42 (m, 3H), 1.60 (m, 4), 2.5 (m, 3H), 2.87 (dd, 1H, J=6.7, 13.9 Hz), 3.07 (dd, 1H, J=6.8, 13.9 Hz), 5.62 (t, 1H, J=6.8 Hz), 6.61 (d, 2H, J=8.4 Hz), 6.98 (d, 2H, J=8.5 Hz), 7.42 (t, 2H, J=7.4 Hz), 7.55 (m, 1H), 7.89 (d, 2H, J=7.2 Hz). $^{13}$C NMR (CD$_3$OD) δ27.40, 31.29, 31.66, 34.72, 37.81, 41.63, 49.11, 56.37, 116.15, 129.07, 129.61, 129.70, 131.45, 134.45, 137.18, 157.08, 176.06, 176.35, 200.32. MS (DCI/NH$_3$) m/e 424 (M+H)$^+$, 195.

EXAMPLE 33

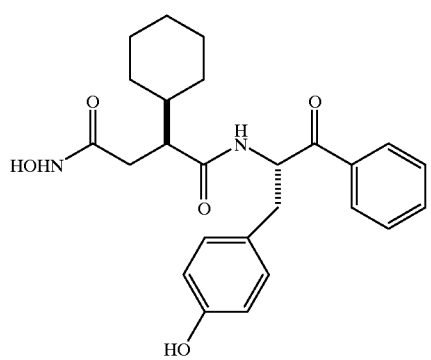

The desired compound was prepared according to the method of Example 5, except substituting the compound of Example 33 for the compound of Example 4. mp 144–145° C. $^1$H NMR (300 MHz, DMSO-d6) δ0.7–1.0 (bdm, 5H), 1.2–1.6 (bdm, 6H), 2.01 (m, 2H), 2.58 (m, 1H), 2.76 (dd, 1H, J=7.4, 13.9 Hz), 2.97 (dd, 1H, J=6.8, 13.9 Hz), 5.39 (q, 1H, J=7.1 Hz), 6.59 (d, 2H, J=8.5 Hz), 7.01 (d, 2H, J=8.4 Hz), 7.46 (t, 2H, J=7.8 Hz), 7.62 (m, 1H), 7.88 (d, 2H, J=7.1 Hz), 8.65 (s, 1H), 9.14 (s, 1H), 10.32 (s, 1H). MS (DCI/NH$_3$) m/e 456 (M+NH$_4$)$^+$, 439 (M+H)$^+$. Anal calcd for C$_{25}$H$_{30}$N$_2$O$_5$·0.75 H$_2$O: C, 66.43; H, 7.02; N, 6.20. Found: C, 66.53; H, 6.79; N, 6.22. [α]$_d$=–12° (CH$_3$OH, c=0.13 g/mL).

EXAMPLE 34

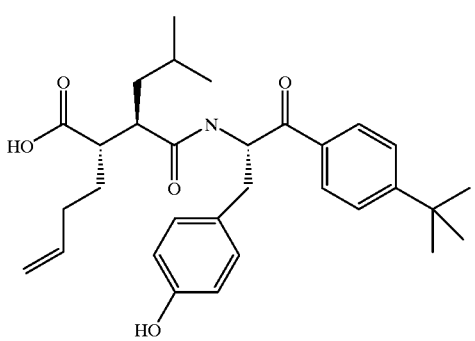

EXAMPLE 34A

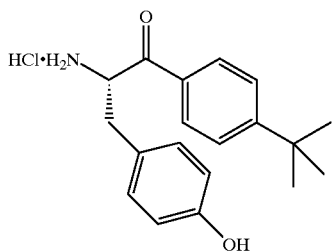

The desired compound was prepared by adding 4-bromo-tert-butylbenzene to a 0° C. solution of nBuLi in diethyl ether. The resulting 4-tert-butylphenyllithium solution was added to a −78° C. solution of N-BOC-tBu(OH) tyrosine in diethyl ether. The solution was stirred at −78° C. for 30 minutes, warmed to 0° over 1 hour and quenched with an aqueous solution of NH₄Cl. The aqueous layer was extracted twice with diether ether and the combined organics were washed with brine, dried (Na₂SO₄), filtered and concentrated in vacuo. Flash chromatography gave the BOC-protected compound which was immediately taken up in 4N HCl-dioxane and stirred for 30 minutes. The resulting slurry was diluted with diethyl ether, filtered and dried for 16 hours under high vacuum, to give 34a.

EXAMPLE 34B

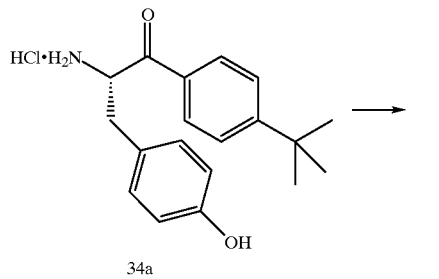

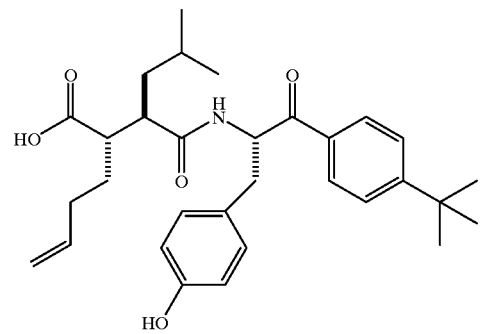

The desired compound was prepared according to the method of Examples 19C and 32E, except substituting 34a for 19b, and substituting succinate ester 1 for succinate ester 3. ¹H NMR (300 MHz, CD₃OD) δ0.67 (d, 3H, J=6.5 Hz), 0.75 (d, 3H, J=6.4 Hz), 0.95 (m, 3H), 1.16 (m, 1H), 1.35 (s, 9H), 1.52 (m, 1H), 1.82 (m, 1H), 1.94 (m, 1H), 2.34 (m, 1H), 2.46 (m, 1H), 2.81 (dd, 1H, J=6.2, 14.2 Hz), 3.11 (dd, 1H, J=4.7, 14.2 Hz), 4.89 (bds, 1H), 4.94 (m, 1H), 5.59 (m, 1H), 5.73 (m, 1H), 6.68 (d, 2H, J=8.5 Hz), 7.11 (d, 2H, J=8.4 Hz), 7.55 (d, 2H, J=6.7 Hz), 7.97 (d, 2H, J=6.8 Hz), 8.59 (d, 1H, J=5.6 Hz). MS (DCI/NH₃) m/e 508 (M+H)⁺.

EXAMPLE 35

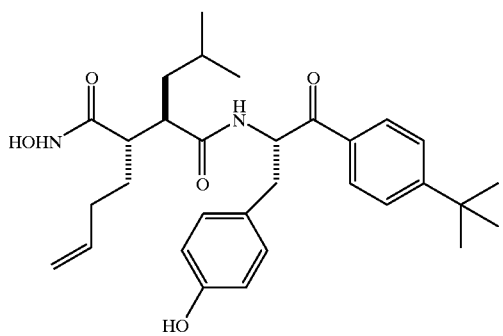

The desired compound was prepared according to the method of Example 1F, except substituting the compound of Example 34 for 1e. ¹H NMR (300 MHz, CD₃OD) δ0.67 (d, 3H, J=6.4 Hz), 0.74 (d, 3H, J=6.4 Hz), 0.86 (m, 2H), 0.95 (m, 1H), 1.14 (m, 1H), 1.34 (s, 9H), 1.42 (m, 1H), 1.77 (m, 1H), 2.03 (m, 1H), 2.43 (m, 1H), 2.83 (dd, 1H, J=9.8, 13.9 Hz), 3.10 (dd, 1H, J=4.4, 13.9 Hz), 4.80 (m, 1H), 4.92 (m, 1H), 5.53 (m, 1H), 5.77 (m, 1H), 6.69 (d, 2H, J=7.6 Hz), 7.13 (d, 2H, J=8.5 Hz), 7.54 (d, 2H, J=8.5 Hz), 7.97 (d, 2H, J=7.6 Hz). ¹³C NMR (CD₃OD) δ21.46, 24.45, 26.49, 30.55, 31.45, 32.29, 36.00, 37.37, 41.63, 47.08, 49.84, 56.31, 115.63, 116.28, 126.74, 129.24, 129.70, 131.31, 134.12, 138.71, 157.17, 158.54, 172.87, 176.02, 199.57. MS (DCI/NH₃) m/e 523 (M+H)⁺. Anal calcd for C₃₁H₄₂N₂O₅.0.5 H₂O: C, 70.03; H, 8.15; N, 5.27. Found: C, 69.92; H, 8.15; N, 5.21.

EXAMPLE 36

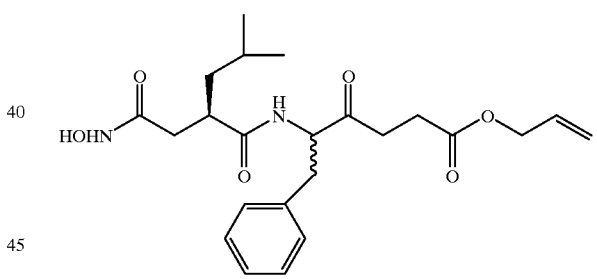

EXAMPLE 36A

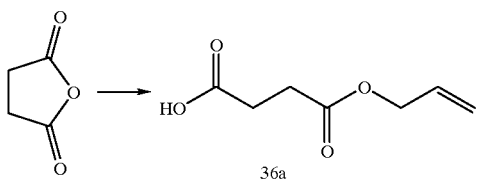

A suspension of succinic anhydride (4 g, 40 mmol), allyl alcohol (2.7 mL, 40 mmol) and DMAP (5.9 g, 48 mmol) in 200 mL toluene was refluxed for 4 hours and then cooled to ambient temperature and concentrated. The residue was partitioned between EtOAc and brine. The aqueous layer was extracted with EtOAc and then acidified to pH 2 with 6M HCl. The acidic aqueous phase was extracted with EtOAc (3×) to give an organic layer which was washed with brine (2x), dried (MgSO₄), filtered and concentrated to afford 36a (5.96 g) as a clear liquid which was used without further purification.

EXAMPLE 36B

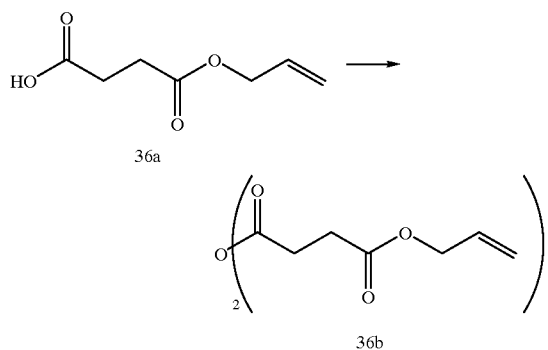

To a solution of carboxylic acid 36a (3 g, 19 mmol) in 95 mL CH₂Cl₂ was added EDC (1.8 g, 9.5 mmol). The reaction mixture was stirred for 3 hours and then poured into a separatory funnel containing 20 mL of ice water. The organic layer was washed with ice-cold water, saturated aqueous NaHCO₃ and brine, dried with MgSO₄, filtered and concentrated in vacuo to afford 36b (2.8 g) which was used without purification.

EXAMPLE 36C

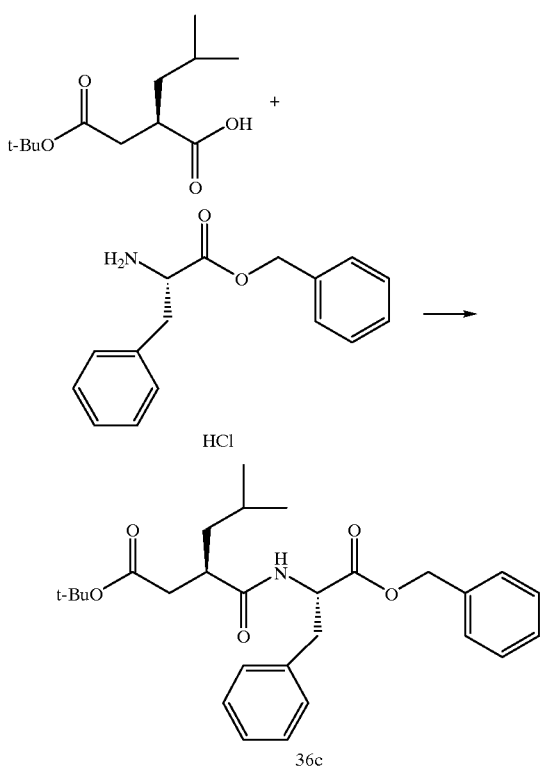

To a solution of R-2-(i-butyl)-succinic acid-4-t-butyl ester (1 g, 4.35 mmol), O-benzylphenylalanine hydrochloride salt (1.52 g, 5.22 mmol, Aldrich), HOBT (704 mg, 5.22 mmol) and NMM (1.4 mL, 13 mmol) in 22 mL DMF at 0° C. was added EDC (1g, 5.22 mmol) in a single portion. The resulting solution was allowed to slowly warm to ambient temperature and then was stirred for 3 days. The reaction mixture was partitioned between water and ethyl acetate. The aqueous layer was extracted with EtOAc (3x) and the combined organic layers were washed with 1M NaHSO₄, 1M NaHCO₃ and brine, dried with MgSO₄, filtered and concentrated in vacuo. The residue was purified by flash chromatography (CH₂Cl₂ then 2% MeOH—CH₂Cl₂) to give 36c (1.96 g) as a yellow oil.

EXAMPLE 36D

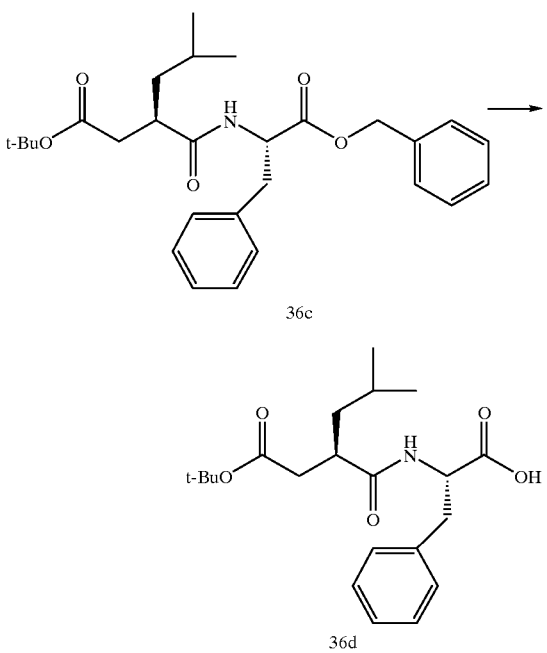

Hydrogenation of benzyl ester 36c (1.96 g, 4.2 mmol; 200 mg 10% Pd/C; methanol; 1 atm hydrogen) gave 36d (1.57 g) as a thick oil which was used without further purification.

EXAMPLE 36E

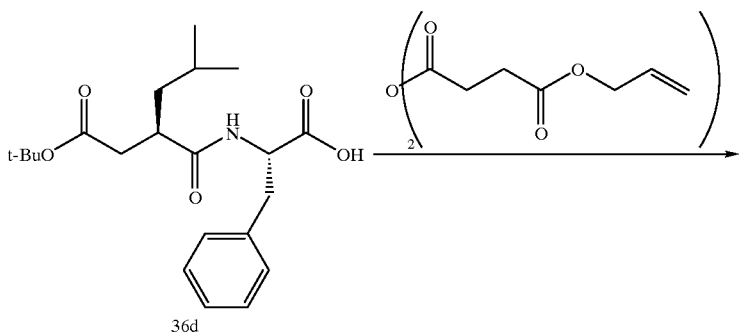

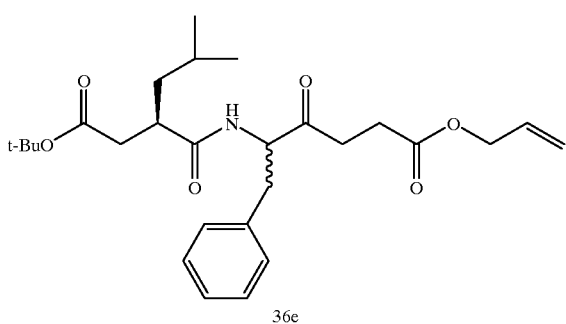

To neat anhydride 36b (2.7 g, 9 mmol) was added a solution of carboxylic acid 36d (1.57 g, 4.16 mmol) in 10 mL $CH_2Cl_2$, $Et_3N$ (864 uL, 6.24 mmol) and DMAP (21 mg, 9 mmol). The resulting yellow solution was refluxed in an oil bath at 50° C. for 3 hours, cooled, concentrated and then stirred in the presence of 50 mL 5% NaHCO3 for 30 minutes. This mixture was diluted with EtOAc and the separated aqueous layer was extracted with EtOAc. The combined organic layers were washed with 1M $NaHSO_4$ and brine, dried with $MgSO_4$, filtered and concentrated. The residue was purified by flash chromatographed (15% ethyl acetate-hexane then 35% ethyl acetate hexane) to give 36e (952 mg) as a yellow foam.

EXAMPLE 36E

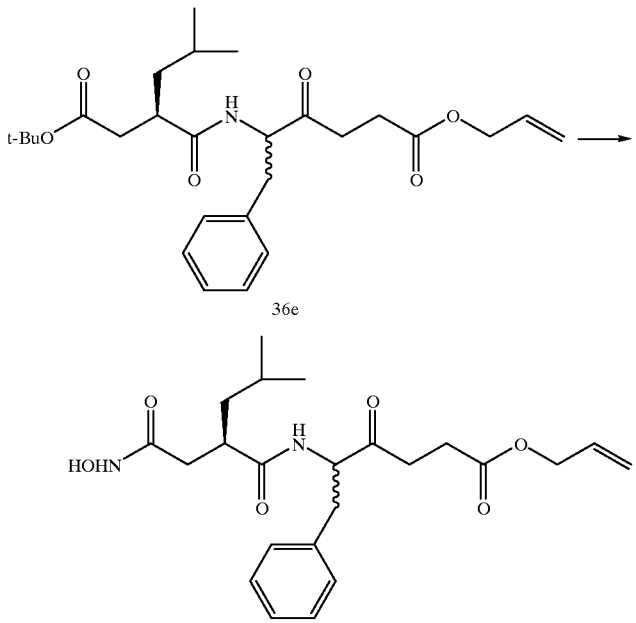

The desired compound was prepared according to the method of Examples 1E and F, except substituting 36e for 1d. mp 126–129° C. $^1$H NMR (300 MHz, DMSO-d6) δ0.6–1.0 (m, 8H), 1.1–1.4 (m, 2H), 1.8–2.2 (m, 2H), 2.6–3.2

(m, 6H), 4.2–4.6 (m, 3H), 5.2–5.4 (m, 2H), 5.8–6.0 (m, 1H), 7.1–7.3 (m, 5H), 8.4–8.6 (m, 1H), 8.45–8.55 (m, 1H), 8.70 and 8.73 (two s, 1H), 10.36 and 10.40 (two s, 1H). MS (DCI/NH₃) m/e 433 (M+H)⁺, 450 (M+NH₄)⁺.

EXAMPLE 37

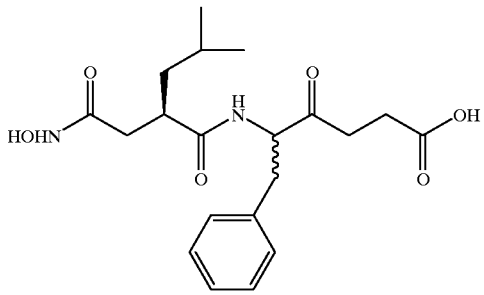

To a solution of the compound of Example 36 (329 mg, 0.76 mmol) in 6 mL THF was added palladium(0) bis(dibenzylideneacetone) (44 mg, 0.08 mmol), triphenylphosphine (42 mg, 0.16 mmol) and morpholine (662 uL, 7.6 mmol). The resulting clear, yellow solution was stirred for 1 hour and then concentrated. The residue was partitioned between CH₂Cl₂ and H₂O and the separated aqueous layer was extracted with CH₂Cl₂ (2×). The aqueous layer was concentrated, redissolved in H₂O, filtered and the desired compound (135 mg) was isolated by reverse-phase HPLC (0–30% CH₃CN/H₂O; 21 mm Dynamax 60A C18 column; 12 mL/minutes). mp 120–121° C. ¹H NMR (300 MHz, DMSO-d6) δ0.60 (d, 3H, J=5.4 Hz), 0.67 (d, 3H, J=5.7 Hz), 0.8–1.0 (m, 2H), 1.1–1.3 (m, 1H), 1.91 (dd, 1H, J=14.4,7.8 Hz), 2.10 (dd, 1H, J=14.4, 6.6 Hz), 2.36 (t, 2H, J=6.3 Hz), 2.6–2.9 (m, 5H), 2.70 (t, 4H, J=4.8 Hz), 3.05 (dd, 1H, J=14.1, 4.2 Hz), 3.52 (t, 4H, J=4.8 Hz), 4.4–4.5 (m, 1H), 7.1–7.3 (m, 5H), 8.47 (d, 1H, J=8.4 Hz). MS (DCI/NH₃) m/e 393 (M+H)⁺. Anal calcd for C₂₀H₂₈N₂O₆.1.0 H₂O: C, 57.93; H, 7.90; N, 8.44. Found: C, 57.91; H, 7.55; N, 8.76. [α]=+62° (c 0.3, MeOH).

EXAMPLE 38

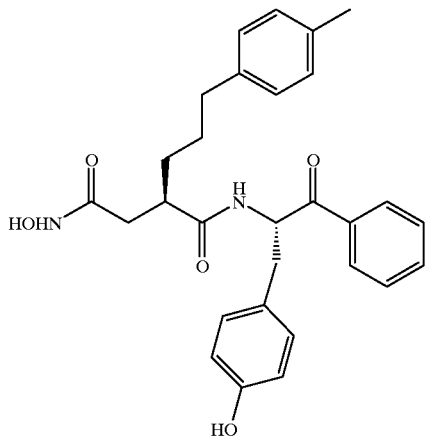

The desired compound was prepared according to the method of Example 6 substituting succinate ester 4 for 5 and ketone 19b for 2c. ¹H NMR (300 MHz, DMSO-d₆) d 9.18 (s, 1H), 8.76 (s, 1H), 8.5–8.4 (m, 1H), 7.92–7.88 (d, 2H, J=7.1 Hz), 7.58–7.57 (m, 1H), 7.48–7.45 (m, 1H), 7.03–6.98 (m, 3H), 6.85–6.82 (d, 2H, J=7.4 Hz), 6.61–6.58 (d, 2H, J=8.2 Hz), 5.45–5.40 (m, 1H), 3.10–2.87 (m, 2H), 2.8–2.6 (m, 3H), 2.23 (s, 3H), 1.88–187 (m, 1H), 1.2–1.15 (m, 2H). MS (ESI) m/e 487 (M–H)⁻. Anal. Calcd for: C₂₉H₃₂N₂O₅.0.75H₂O: C, 69.37; H, 6.72; N, 5.57. Found: C, 69.37; H, 6.74; N, 5.88.

EXAMPLE 39

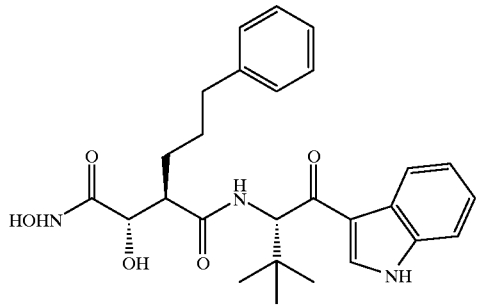

The desired compound was prepared according to the method of Examples 10A,10B and 5 except substituting 27f for 10a and 9a for 1c. ¹H NMR (300 MHz, DMSO-d₆) d 11.98 (s, 1H), 10.63 (s, 1H), 8.83 (s, 1H), 8.41 (s, 1H), 8.27–8.2 (m, 1H), 8.01–7.98 (d, 1H, J=9.5 Hz), 7.50–7.48 (m, 1H), 7.27–7.18 (m, 2H), 6.98–6.85 (m, 3H), 6.76–6.74 (d, 2H, J=8.4 Hz), 5.27–5.22 (d, 1H, J=8.4 Hz), 5.18–5.15 (d, 1H, J=9.6 Hz), 3.82–3.77 (t, 1H, J=9.5, 7.7 Hz), 2.80–2.75 (m, 1H), 2.40–2.33 (m, 1H), 2.25–2.21 (m, 1H), 1.41–1.30 (m, 1H), 1.25–1.20 (m, 3H), 1.00 (s, 9H). MS (ESI) m/e 480 (M+H)⁺, 478 (M–H)⁻. Anal. Calcd for: C₂₇H₃₃N₃O₄.0.50H₂O: C, 66.37; H, 7.01; N, 8.68. Found: C, 66.39; H, 6.96; N, 8.45.

EXAMPLE 40

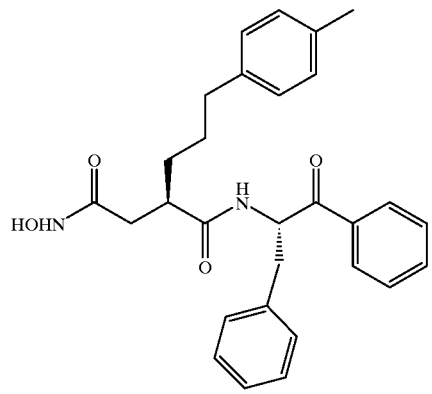

The desired compound was prepared according to the method of Example 6 substituting succinate ester 4 for 5 and ketone 15a for 2c. ¹H NMR (300 MHz, DMSO-d₆) d 10.31 (s, 1H), 8.61 (m, 1H), 8.55–8.52 (d, 1H, J=8.1 Hz), 7.94–7.91 (d, 2H, J=8.5 Hz), 7.58–7.55 (m, 1H), 7.48–7.45 (m, 2H), 7.25–7.14 (m, 5H), 7.00–6.98 (d, 2H, J=7.8 Hz), 6.85–6.82 d, 2H, J=7.9 Hz), 5.51–5.49 (m, 1H), 3.14–3.08 (m, 1H), 2.91–2.83 (m, 1H), 2.71–2.59 (m, 1H), 2.33–2.26 (m, 2H), 1.83–1.80 (m, 2H), 1.23–1.18 (m, 3H). MS (ESI) m/e 471 (M–H)⁻. Anal. Calcd for: C₂₉H₃₂N₂O₄.0.50H₂O: C, 72.32; H, 6.90; N, 5.81. Found: C, 72.57; H, 6.88; N, 5.80.

EXAMPLE 41

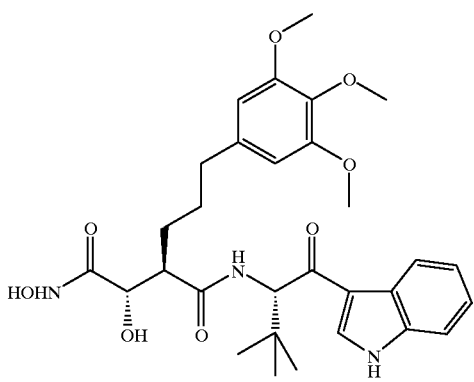

EXAMPLE 41A

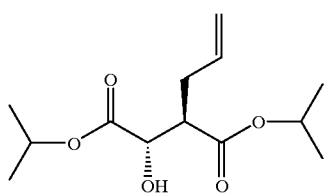

41a

The desired compounds was prepared according to the method of Example 27B, except substituting allyl bromide for cinnamyl bromide.

EXAMPLE 41b

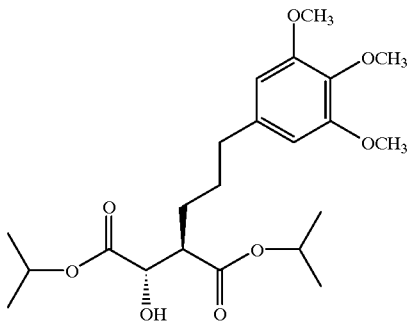

41b

A solution of 41a (5.0 g, 19.4 mmol) in THF (60 mL) at 0° C. was treated with 9-BBN, stirred at ambient temperature for 1.5 hours, treated sequentially with DMF, [1,1'-bis(diphenylphosphino)-ferrocene]dichloropalladium (790 mg, 0.97 mmol), 3,4,5-trimethoxybromobenzene (14.4 g, 58.3 mmol) and cesium carbonate (38.6 g, 118.5 mmol), stirred at 60° C. for 5.5 hours, cooled to room temperature and diluted with water, extracted with ethyl acetate, and the combined organic layers were washed with water and brine, dried ($Na_2SO_4$) and concentrated to an oil. The oil was purified on silica gel with 10% to 30% ethyl acetate/hexane to provide 4.95 g (59.9%) of 41b as a yellow oil. MS (APCI) m/e 427 (M+H)$^+$.

EXAMPLE 41C

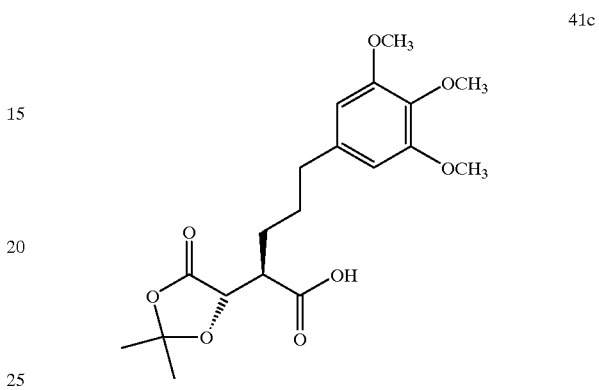

41c

The desired compound was prepared according to the method of Example 27D and 27E, except substituting 41b for 27c. MS (ESI) m/e 383 (M+H)$^+$.

EXAMPLE 41D

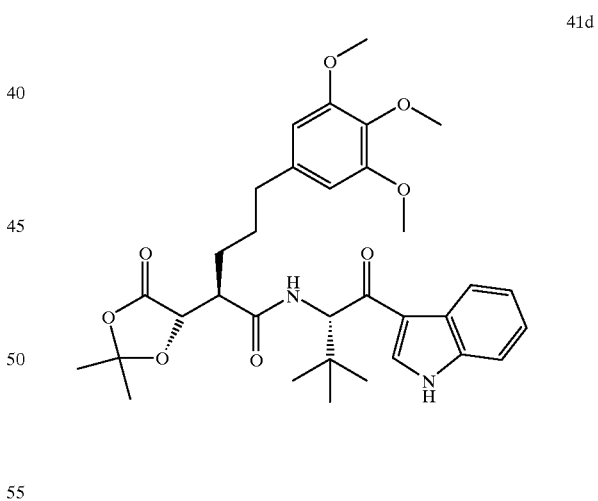

41d

A solution of 41C (755 mg, 1.97 mmol) in DMF (15 mL) at 0° C. was treated sequentially with HOBT (294 mg, 2.17 mmol), NMM (477 mL, 438.8 mg, 4.35 mmol), EDC (417 mg, 2.17 mmol) and indoleketone-tert-leucine, 10a (500 mg, 2.17 mmol), stirred at room temperature for 17 hours, and diluted with water, extracted with ethyl acetate. The combined organic layers were washed with water and brine, dried ($Na_2SO_4$), and concentrated. The residue was purified on silica gel with 50% ethyl acetate/hexane to provide 402 mg (34%) of the title compound as a pale yellow foam. MS (APCI) m/e 595 (M+H)$^+$.

EXAMPLE 41E

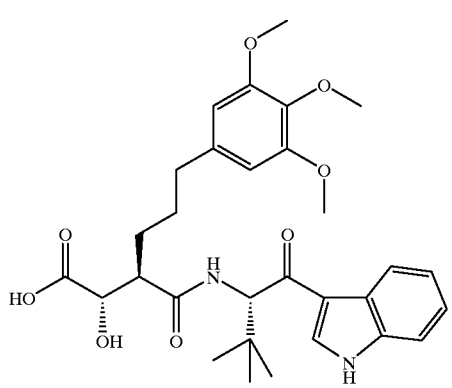

41e

A solution of 41d (400 mg, 0.673 mmol) in trifluoroacetic acid (3 mL) was stirred at room temperature for 4 hours, and concentrated. The residue was purified on silica gel with 0.1% acetic acid in 10% MeOH/CH$_2$Cl$_2$ to provide 353.4 mg (94.7%) of title compound as a white solid. MS (ESI) m/e 555 (M+H)$^+$.

EXAMPLE 41F

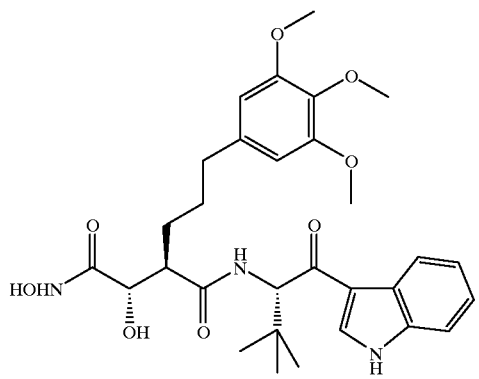

A solution of 41e (326 mg, 0.588 mmol) in DMF (15 mL) at 0° C. was treated sequentially with HOBT (103.4 mg, 0.765 mmol), NMM (168 mL, 154.6 mg, 1.53 mmol), EDC (146.6 mg, 0.765 mmol) and O-(tert-butyldimethyl-silyl) hydroxyamine (112.6 mg, 0.765 mmol), stirred at room temperature for 17 hours, and diluted with water, extracted with ethyl acetate. The combined organic layers were washed with water and brine, dried (Na$_2$SO$_4$), and concentrated. The residue was purified on silica gel with 7% MeOH/CH$_2$Cl$_2$ to provide 32 mg (9.56%) of the title compound as a pale pink solid. 1H NMR (300 MHz, DMSO-d$_6$) δ0.979 (s, 9H), 1.130–2.000 (m, 4H), 2.272–2.392 (m, 2H), 2.700 (m, 1H), 3.546 (s, 3H), 3.568 (s, 6H), 3.783 (t, 1H), 5.146 (d, 1H), 5.255 (d, 1H), 6.282 (s, 2H), 7.138–7.237 (m, 2H), 7.457 (d, 1H), 7.909 (d, 1H), 8.182 (d, 1H), 8.412 (s, 1H), 8.849 (s, 1H), 10.633 (s, 1H), 11.969 (s, 1H). MS (APCI) m/e 570 (M+H)$^+$. High resolution MS (FAB) m/e calcd for (M+H)$^+$: C$_{30}$H$_{40}$N$_3$O$_8$: 570.2815. Found: 570.2822.

EXAMPLE 42

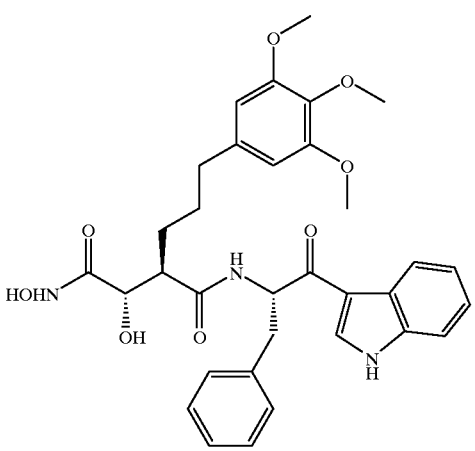

The desired compound was prepared according to the methods of Example 41, except substituting 2c for 10a in Example 41D. 1H NMR (300 MHz, DMSO-d$_6$) δ1.236–1.377 (m, 4H), 2.274–2.441 (m, 2H), 2.918–2.988 (dd, 1H), 3.111–3.183 (dd, 1H), 3.570 (s, 3H), 3.638 (s, 6H), 3.826 (t, 1H), 5.222 (d, 1H), 5.387 (q, 1H), 6.343 (s, 2H), 7.118–7.276 (m, 9H), 7.439 (d, 1H), 8.125 (d, 1H), 8.297 (s, 1H), 8.435 (d, 1H). MS (APCI) m/e 604 (M+H)$^+$. Anal. calcd for C$_{33}$H$_{37}$N$_3$O$_8$·HOAc: C, 63.33; H, 6.22; N, 6.33. Found: C, 63.10; H, 6.05; N, 6.05.

EXAMPLE 43

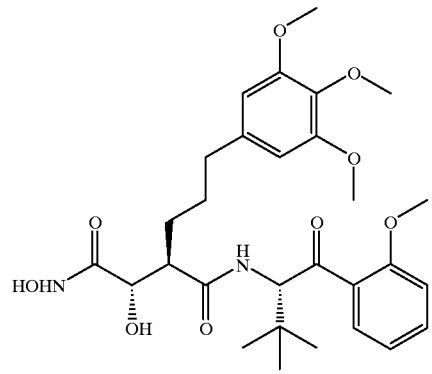

EXAMPLE 43A

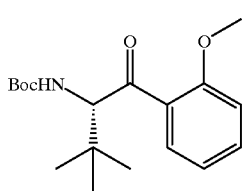

43a

A solution of Boc-tert-leucine-N-methoxyl-N'-methylamide (1.15 g, 4.2 mmol) in ethyl ether (70 mL) at −78° C. was treated with 2-lithioanisole (prepared by addition of 2-bromoanisole (1.57 mL, 2.36 g, 12.6 mmol) to a solution of n-butyllithium (2.5M/hexane, 5.04 mL, 12.6 mmol) in ethyl ether (15 mL) at 0° C.), stirred at −30° C. to −45° C. for 1 hour and poured onto 1:1 Et₂O: 0.1M HCl. The aqueous layer was separated, and extracted with ether, the combined organic layers were washed with brine, dried (Na₂SO₄), and concentrated. The residue was purified on silica gel with 2%–5%–10% ethyl acetate/hexane to provide 788 mg (58%) of the title compound as a colorless oil. MS (DCI/NH₃) m/e 322 (M+H)⁺.

EXAMPLE 43B

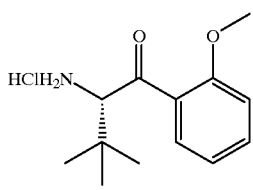

43b

A solution of 43a (786 mg, 2.45 mmol) in HCl/dioxane (4M, 6 mL) was stirred at room temperature for 1 hour, diluted with ether, filtered. The filtrate was washed with ether, and dried under high vacuum to provide 550.6 mg (87.3%) of the title compound as a white solid. MS (APCI) m/e 222 (M−HCl+H)⁺.

EXAMPLE 43C

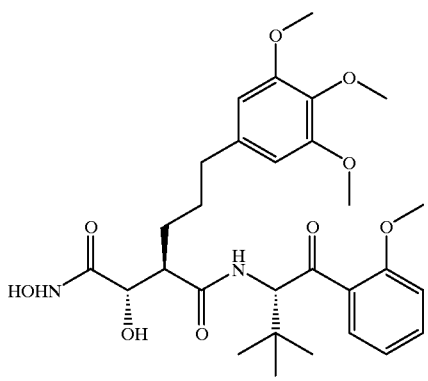

The desired compound was prepared according to the method of Examples 41D–F, except substituting ketone 43b for 10a. 1H NMR (300 MHz, DMSO-d₆) δ0.883 (s, 9H), 1.171–1.399 (m, 4H), 2.291–2.515 (m, 2H), 2.728–2.833 (m, 1H), 3.575 (s, 3H), 3.635 (s, 6H), 3.797 (s, 3H), 3.772–3.813 (m, 1H), 5.199 (d, 1H), 5.304 (d, 1H), 6.388 (s, 2H), 6.960–7.009 (t, 1H), 7.104 (d, 1H), 7.449–7.501 (t, 1H), 7.550–7.588 (dd, 1H), 7.929 (d, 1H), 8.852 (s, 1H), 10.645 (s, 1H). MS (ESI) m/e 561 (M+H)⁺. Anal. calcd for C₂₉H₄₀N₂O₉: C, 62.12; H, 7.19; N, 4.99. Found: C, 62.20; H, 7.22; N, 4.71.

EXAMPLE 44

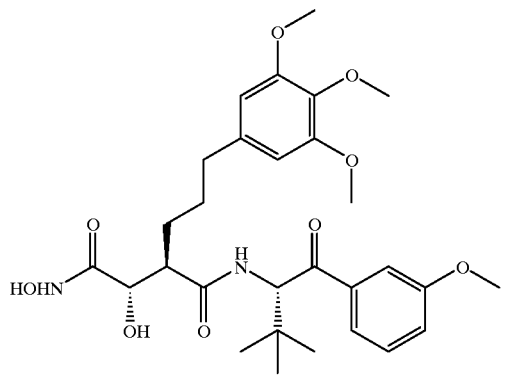

EXAMPLE 44A

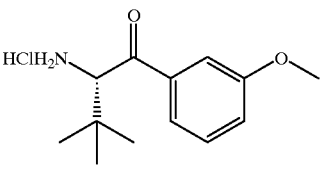

The desired compound was prepared following the methods of Examples 43A and 43B, except substituting 3-lithioanisole for 2-lithio anisole. MS (ESI) m/e 222 (M−HCl+H)⁺.

EXAMPLE 44B

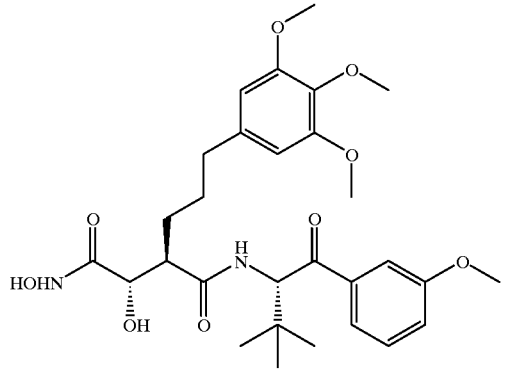

The desired compound was prepared following the methods of Example 43C, except substituting 44a for 43a. 1H NMR (300 MHz, DMSO-d₆) δ0.933 (s, 9H), 1.138–1.328 (m, 4H), 2.244–2.428 (m, 2H), 2.794–2.826 (m, 1H), 3.584 (s, 3H), 3.666 (s, 6H), 3.793 (s, 3H),3.774–3.812 (m, 1H), 5.223 (d, 1H), 5.298 (d, 1H), 6.339 (s, 2H), 7.151–7.187 (dd, 1H), 7.388–7.441 (m, 2H), 7.571 (d, 1H), 8.137 (d, 1H), 8.859 (s, 1H), 10.655 (s, 1H). MS (ESI) m/e 561 (M+H)⁺. Anal. calcd for C₂₉H₄₀N₂O₉.0.25H₂O: C, 61.63; H, 7.22; N, 4.95. Found: C, 61.78; H, 7.48; N, 4.58.

EXAMPLE 45

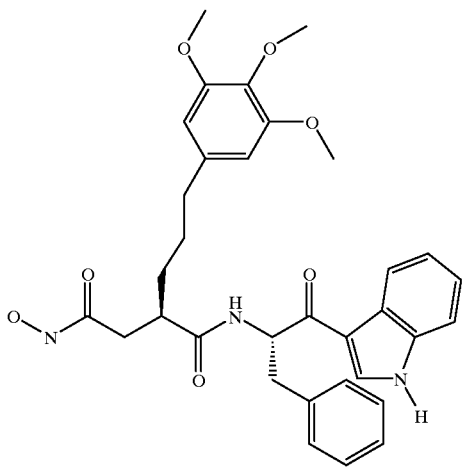

EXAMPLE 45A

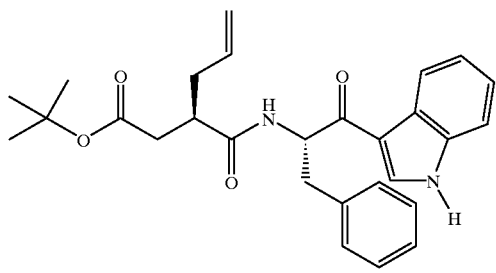

45a

The desired compound was prepared according to the method of Example 2C, except coupling succinate 7 instead of 4 with ketone 2c. MS (ESI) m/e 461 (M+H)$^+$.

EXAMPLE 45B

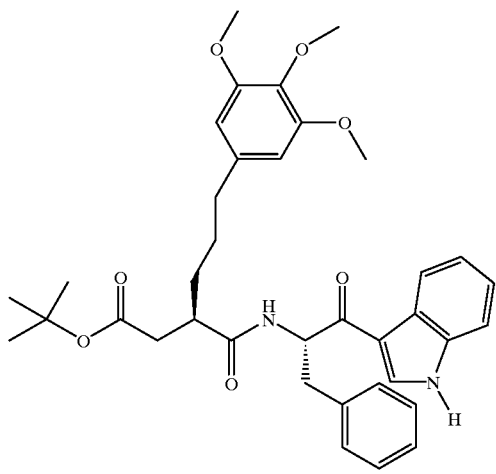

45b

The desired compound was prepared according to the method of Example 41B, except using 45a instead of 41a.

EXAMPLE 45C

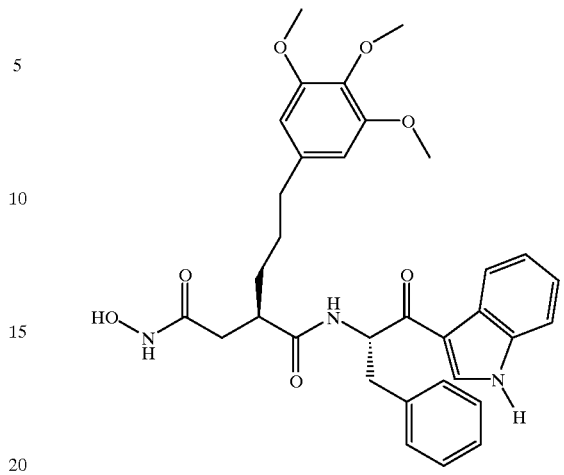

The desired compound was prepared according to the method of Examples 1E and 5A–B except substituting 45b from above for 1d. mp 104° C. $^1$H NMR (300 MHz, DMSO-d$_6$) 11.92 (s, 1H), 10.35 (d, 1H, J=0.7 Hz), 8.70 (d, 1H, J=1.4 Hz), 8.47 (d, 1H, J=8.5 Hz), 8.36 (d, 1H, J=3.0 Hz), 8.18–8.14 (m, 1H), 7.47–7.42 (m, 1H), 7.32–7.11 (m, 7H), 6.33 (s, 2H), 5.41–5.31 (m, 1H), 3.63 (s, 6H), 3.56 (s, 3H), 3.16–3.07 (m, 1H), 2.98–2.88 (m, 1H), 2.77–2.65 (m, 1H), 2.77–2.65 (m, 3H), 1.93–1.87 (m, 1H), 1.44–1.18 (m, 4H). MS (ESI) m/e 588 (M+H)$^+$.

EXAMPLE 46

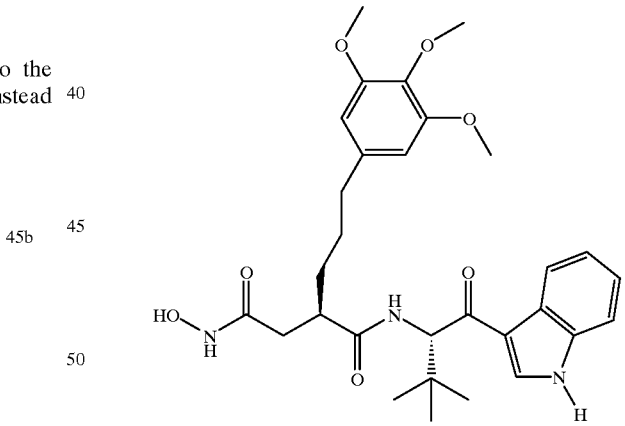

The desired compound was prepared according to the method of Example 45A–45C, except substituting ketone 9a for 2c in Example 45A. mp 126° C. $^1$H NMR (300 MHz, DMSO-d$_6$) 11.96 (d, 1H, J=2.2 Hz), 10.37 (d, 1H, J=1.4 Hz), 8.69 (d, 1H, J=1.5 Hz), 8.39 (d, 1H, J=2.9 Hz), 8.18 (d, 1H, J=7.4 Hz), 8.05 (d, 1H, J=9.2 Hz), 7.48–7.43 (m, 1H), 7.24–7.13 (m, 2H), 6.32 (s, 2H), 5.09 (d, 1H, J=8.8 Hz), 3.60 (s, 6H), 3.56 (s, 3H), 2.96–2.87 (m, 1H), 2.47–2.27 (m, 2H), 2.22–1.98 (m, 2H), 1.47–1.24 (m, 4H), 0.97 (s, 9H). $^{13}$C NMR (300 MHz, DMSO-d$_6$) 193.9, 174.0, 152.5, 137.7, 136.6, 135.4, 134.4, 125.5, 122.9, 121.7, 121.4, 116.9, 112.1, 105.3, 60.3, 59.9, 41.0, 35.3, 34.2, 31.5, 28.2, 27 1. MS (APCI) m/e 554 (M+H)$^+$.

EXAMPLE 47

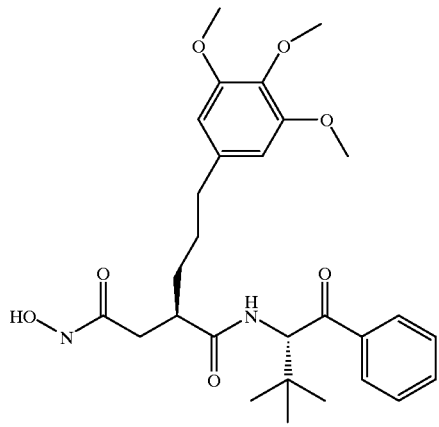

EXAMPLE 47A

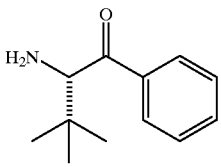

47a

The desired compound was prepared according to the method of Example 43A and 43B, except using phenyl lithium in place of 3-lithioanisole.

EXAMPLE 47B

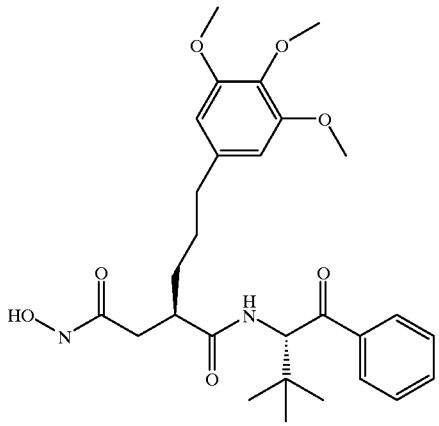

The desired compound was prepared according to the method of Example 45A–45C, except substituting ketone 47a for 2c in Example 45A. mp 146° C. $^1$H NMR (300 MHz, DMSO-d$_6$) 10.36 (s, 1H), 8.67 (s, 1H), 8.22 (d, 1H, J=8.0 Hz), 7.97–7.92 (m, 2H), 7.63–7.45 (m, 3H), 6.38 (s, 2H), 5.27 (d, 1H, J=8.1 Hz), 3.68 (s, 6H), 3.59 (s, 3H), 2.98–2.87 (m, 1H), 2.46–2.26 (m, 2H), 2.22–1.96 (m, 2H), 1.44–1.30 (m, 4H), 0.92 (s, 9H). $^{13}$C NMR (300 MHz, DMSO-d$_6$) 200.3, 174.4, 167.6, 164.8, 152.6, 138.2, 137.8, 135.4, 133.0, 128.6, 128.0, 105.3, 59.9, 59.5, 55.7, 40.6, 35.3, 35.2, 34.0, 31.6, 28.0, 26.9.

EXAMPLE 48

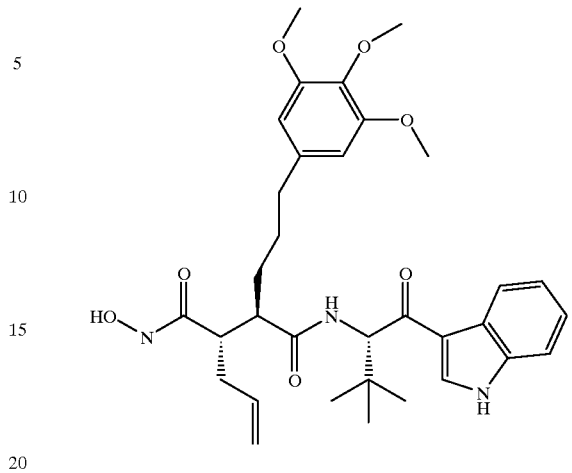

The desired compound was prepared according to the method of Example 2C and 2D, except coupling succinate 9 instead or 4 with ketone 9a instead of 2c.

$^1$H NMR (300 MHz, DMSO-d$_6$) 11.93 (s, 1H), 10.48 (d, 1H, J=1.7 Hz), 8.74 (d, 1H, J=1.7 Hz), 8.42 (d, 1H, J=3.1 Hz), 8.16 (t, 2H, J=8.1 Hz), 7.47–7.43 (m, 1H), 7.23–7.11 Hz), (m, 2H), 7.23–7.11 (m, 2H), 6.28 (s, 2H), 5.76–5.56 (m, 1H), 5.14 (d, 1H, J=8.5 Hz), 4.96–4.90 (m, 2H), 3.58 (s, 6H), 3.56 (s, 3H), 2.80–2.70 (m, 1H), 2.46–2.33 (m, 1H), 2.33–2.13 (m, 3H), 2.10–1.98 (m, 1H), 1.38–1.18 (m, 4H), 1.00 (s, 9H). MS (ESI) m/e 594 (M+H)$^+$. Anal. Calcd for: $C_{33}H_{43}N_3O_7 \cdot 0.50H_2O$: C, 65.76; H, 7.35; N, 6.97. Found: C, 65.70; H, 7.46; N, 6.98.

EXAMPLE 49

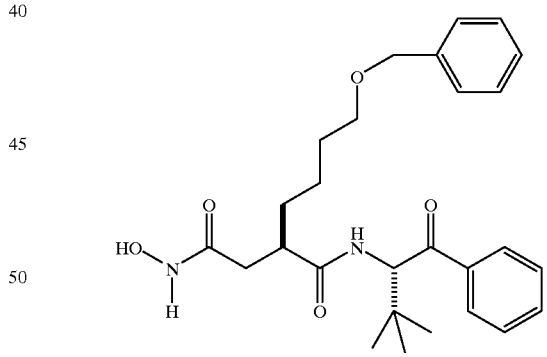

The desired compound was prepared according to the method of Example 2C and 2D, except coupling succinate 10 instead of 4 with ketone 9a instead of 2c.

$^1$H NMR (DMSO-d6) δ0.93 (s, 9H), 1.0–1.43 (m, 6H), 1.95–2.02 (m, 1H), 2.10–2.21 (m, 1H), 2.78–2.90 (m, 1H), 3.21 (t, 2H, J=9 Hz), 4.34 (s, 2H), 7.28 (d, 1H, J=9 Hz), 7.21–7.36 (m, 5H), 7.44–7.50 (m, 2H), 7.53–7.62 (m, 1H), 7.94 (d, 2H, J=8 Hz), 8.24 (d, 1H, J=9 Hz), 8.68 (s, 1H), 10.38 (s, 1H). MS (DCI/NH$_3$) m/e 469 (M+H)$^+$. Anal. calcd for: $C_{27}H_{36}N_2O_5$: C, 69.20; H, 7.74; N, 5.99. Found: C, 69.35; H, 7.70; N, 6.02.

EXAMPLE 50

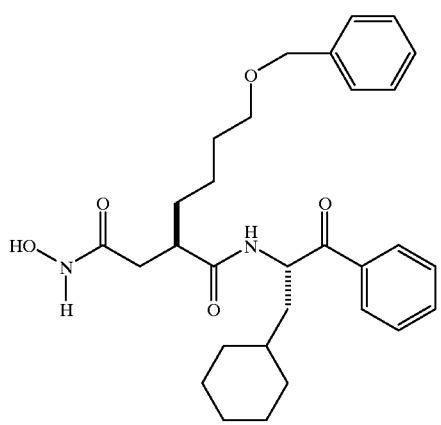

EXAMPLE 50A

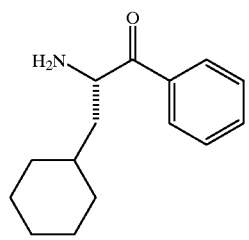

50a

The desired compound was prepared according to the methods of Examples 18A and B, except substituting N-Boc-alpha-cyclohexyl alanine for N-Boc-phenylalanine.

EXAMPLE 50B

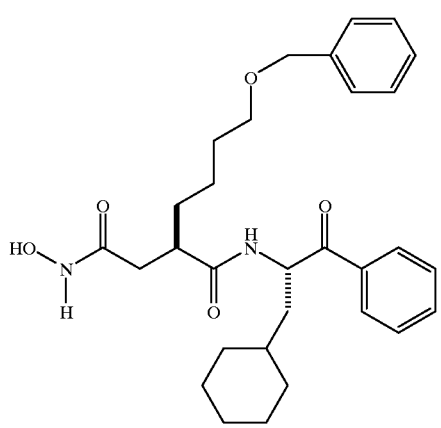

The desired compound was prepared according to the method of Example 2C and 2D, except coupling succinate 10 instead or 4 with ketone 50a instead of 2c. $^1$H NMR (300 MHz, DMSO-d6) δ0.78–1.0 (m, 2H), 1.03–1.68 (m, 16H), 1.78–1.90 (m, 1H), 1.91–2.13 (m, 2H), 2.60–2.74 (m, 1H), 3.21–3.29 (m, 2H), 4.4 (s, 2H), 5.20–5.37 (m, 1H), 7.20–7.39 (m, 5H), 7.41–7.52 (m, 2H), 7.55–7.63 (m, 1H), 7.90 (d, 2H, J=8 Hz), 8.38 (d, 1H, J=8 Hz), 8.70 (s, 1H), 10.38 (s, 1H); MS (DCI/NH$_3$) m/e 509 (M+H)+. Anal. calcd for: $C_{30}H_{40}N_2O_5$: C, 70.83; H, 7.92; N, 5.50. Found: C, 70.63; H, 8.13; N, 5.63.

EXAMPLE 51

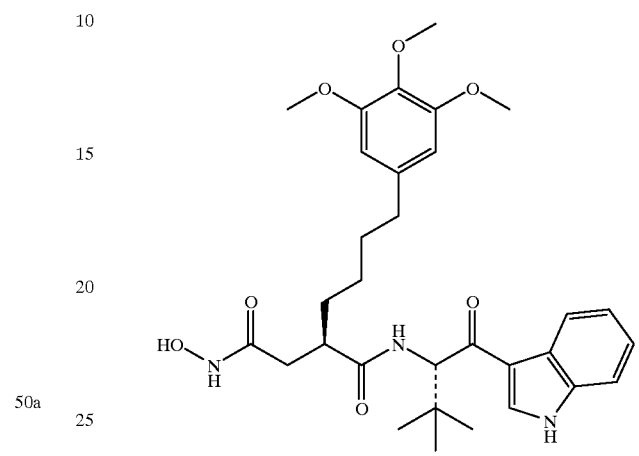

EXAMPLE 51A

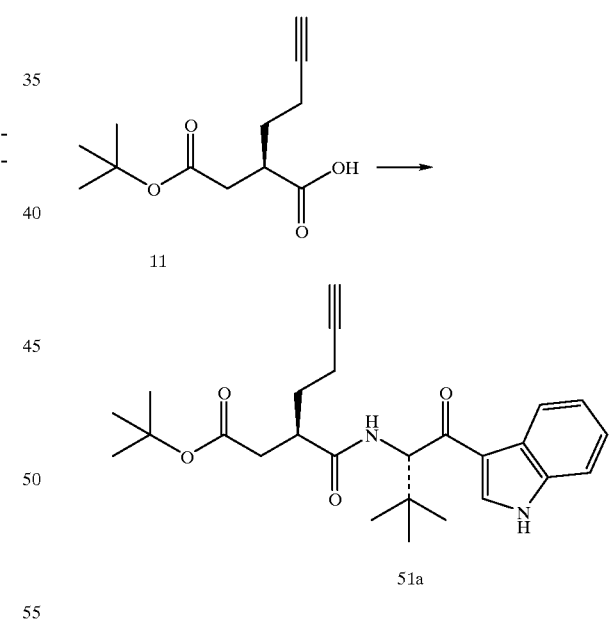

51a

The desired compound was prepared according to the method of Example 2C except substituting succinate ester 11 for 4 and ketone 9a for 2c.

$^1$H NMR (300 MHz, DMSO-d$_6$) δ8.39 (s, 1H), 8.21 (d, 1H), 8.06 (d, 1H), 7.47 (d, 1H), 7.24–7.18 (m, 2H), 5.10 (d, 1H), 2.89–2.87 (m, 1H), 2.69)t, 1H), 2.45 (dd, 1H), 2.29 (dd, 1H), 2.07–1.91 (m, 2H), 1.58–1.42 (m, 2H), 1.37)s, 9H), 0.97 (s, 9H). MS (DCI/NH$_3$) m/e 439 (M+1)$^+$.

EXAMPLE 51B

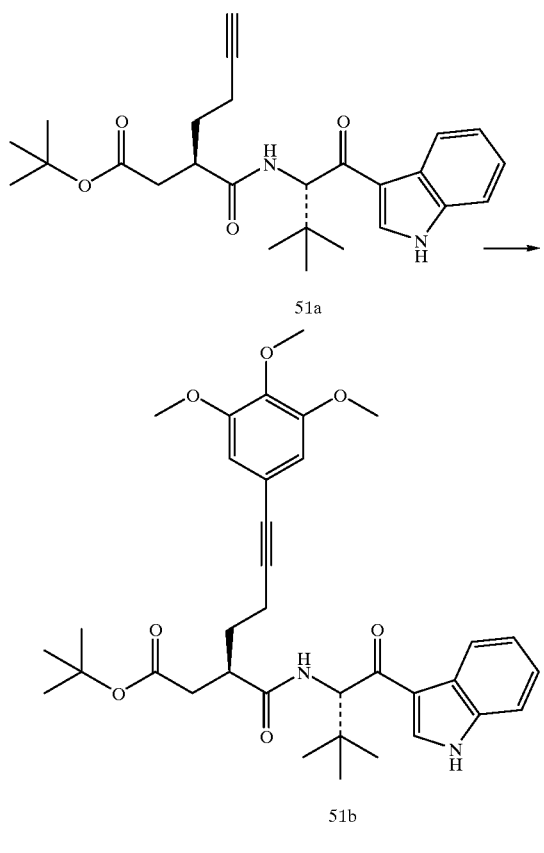

A solution of the alkyne 51a (211 mg, 0.48 mmol) and 1-bromo-3,4,5-trimethoxybenzene (131 mg, 0.528 mmol) in 2:1 triethylamine/acetonitrile (4.8 mL) was degassed with $N_2$ for 20 minutes, treated with 10% palladium on activated carbon (20 mg, 0.0192 mmol) and copper iodide (5 mg, 0.024 mmol), heated at reflux for 24 hours, cooled to 23° C., filtered through Celite, and concentrated to a residue. The residue was purified on silica gel with 50% ethyl acetate/hexane to provided 130 mg of 51b as a white solid. $^1$H NMR (300 MHz, DMSO-$d_6$) δ8.41 (s, 1H), 8.22 (d, 1H), 8.08 (d, 1H), 7.47 (d, 1H), 7.22–7.18 (m, 2H), 6.63 (s, 2H), 5.14 (d, 1H), 3.73 (s, 6H), 3.63 (s, 3H), 2.96–2.90 (m, 1H), 2.37–2.10 (m, 4H), 1.65–1.55 (m, 2H), 1.38 (s, 9H), 0.98 (s, 9H). MS (DCI/$NH_3$) m/e 605 $(M+1)^+$.

EXAMPLE 51c

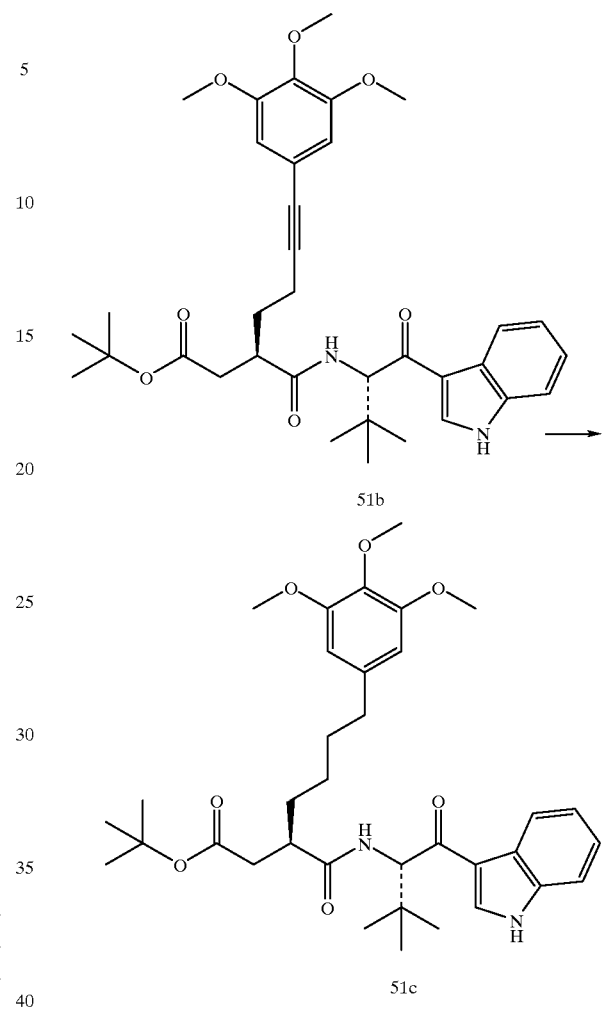

A solution of the alkyne 51b (115 mg, 0.19 mmol) in 1:1 methanol/ethyl acetate (4 mL) was treated with 10% palladium on activated carbon (20 mg, 0.019 mmol) under an atmosphere of hydrogen ($H_2$ balloon) for 16 hours, filtered through Celite, and concentrated to provide 115 mg of 51c. $^1$H NMR (300 MHz, DMSO-$d_6$) δ8.35 (s, 1H), 8.24 (d, 1H), 8.11 (d, 1H), 7.48 (d, 1H), 7.24–7.14 (m, 2H), 6.29 (s, 2H), 5.12 (d, 1H), 3.69 (s, 6H), 3.57 (s, 3H), 282–2.81 (m, 1H), 2.42 (dd, 1H), 2.20 (dd, 1H), 2.13 (t, 1H), 1.37 (s, 9H), 1.33–1.24 (m, 6H), 0.98 (s, 9H). MS (ESI) m/e 607 $(M-1)^+$.

EXAMPLE 51D

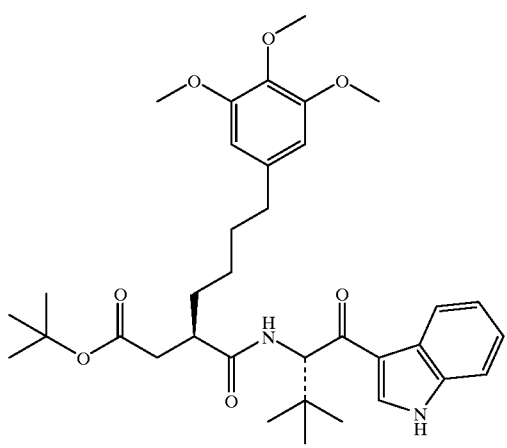

The ester 51c was converted to the desired compound following the procedures described in Examples 1E, 5A and 5B. $^1$H NMR (300 MHz, DMSO-d$_6$) δ8.68 (s, 1H), 8.36 (d, 1H), 8.24 (d, 1H), 8.07 (d, 1H), 7.48 (d, 1H), 7.24–7.14 (m, 2H), 6.29 (s, 2H), 5.10 (d, 1H), 3.69 (s, 6H), 3.57 (s, 3H), 2.82 (m, 1H), 2.21–1.98 (m, 4H), 1.40–1.18 (m, 6H), 0.99 (s, 9H). MS (DCI/NH$_3$) m/e 568 (M+1)$^+$.

Anal. calcd for C$_{31}$H$_{41}$N$_3$O$_7$·H$_2$O: C, 63.57; H, 7.40; N, 7.17. Found: C, 63.52; H, 7.15; N, 6.67.

EXAMPLE 52

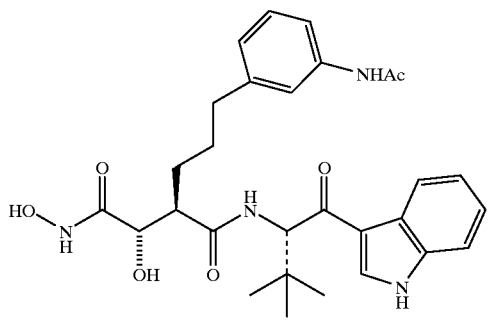

EXAMPLE 52A

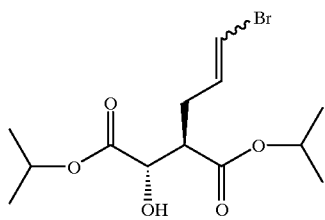

The desired compound was prepared according to the method of Example 27B, except substituting 1,3-dibromo-1-propene for cinnamyl bromide.

EXAMPLE 52B

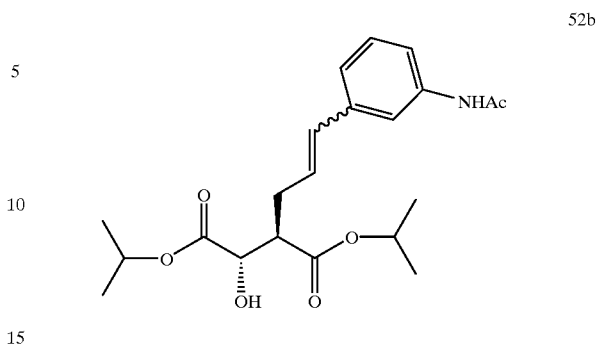

A solution of Example 52a (3.0 g, 8.9 mmol) in DMF (100 mL) at room temperature was treated with [1'-bis (diphenylphosphino)-ferrocene]dichloropalladium (363 mg, 0.445 mmol), 3-acetimidobenzenoboronic acid (2.39 g, 13.35 mmol) and cesium carbonate (8.7 g, 26.7 mmol), stirred at 60° C. for 7 hours, cooled to room temperature and diluted with water, extracted with ethyl acetate, and the combined organic layers were washed with water and brine, dried (Na$_2$SO$_4$) and concentrated to an oil. The oil was purified on silica gel with 50% ethyl acetate/hexane to provide 716.9 mg (20%) of 52b as a yellow oil. MS (ESI) m/e 392 (M+H)$^+$.

EXAMPLE 52C

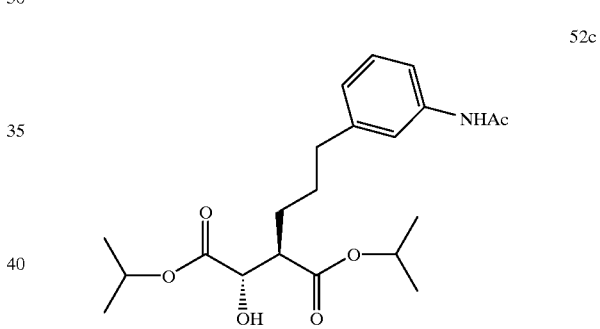

The olefin 52b was converted to the desired compound 52c following the procedure of Example 51C.

EXAMPLE 52D

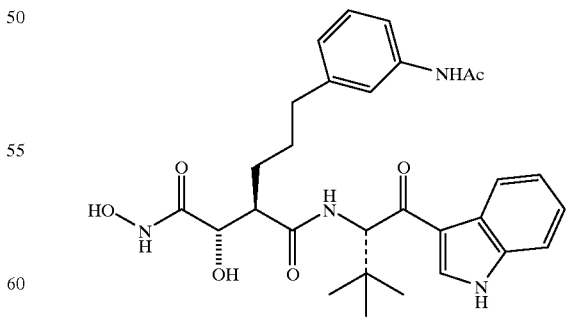

The desired compound was prepared according to the methods of Example 41C–F, except substituting 52c for 41b. $^1$H NMR (DMSO-d6) δ0.989 (s, 9H), 1.23–1.39 (m, 4H), 1.98 (s, 3H), 2.19–2.36 (m, 2H), 2.72–2.76 (m, 1H), 3.77–3.83 (t, 1H, J=8.1 Hz), 5.12–5.16 (d, 1H), J=6 Hz), 5.26–5.29 (d, 1H, J=7.5 Hz), 6.37–6.39 (d, 1H, J=7.8 Hz), 6.72–6.77 (t, 1H, J=7.8 Hz), 7.16–7.25 (m, 4H), 7.45–7.48 (1H), 7.94–7.97 (d, 1H, J=9.6 Hz), 8.21–8.24 (1H), 8.38 (s, 1H), 8.80 (s, 1H), 9.71 (s, 1H), 10.6 (s, 1H), 11.94 (s, 1H). MS (ESI) 537 (M+H)$^+$, 559 (M+Na)$^+$.

EXAMPLE 53

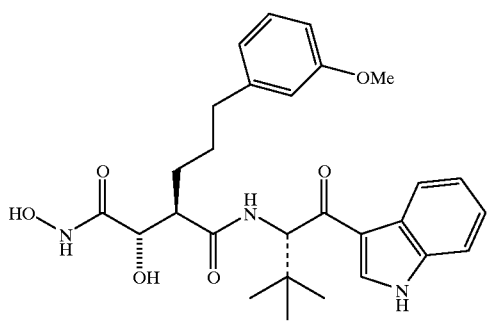

The desired compound was prepared according to the method of Example 52B–D except substituting 3-methoxybenzenoboronic acid for 3-acetimidobenzenoboronic acid. $^1$H NMR (DMSO-d6) δ0.99 (s, 9H), 1.22–1.27 (m, 4H), 2.27–2.39 (m, 2H), 2.74 (dt, 1H), 3.59 (s, 3H), 3.76–3.81(t, 1H, J=8.4 Hz), 5.13–5.16 (d, 1H, J=9.6 Hz), 5.25–5.27 (d, 1H, J=7.2 Hz), 6.31–6.33 (d, 1H, J=7.2 Hz), 6.55–6.68 (2H), 6.75–6.81 (t, 1H, J=7.8 Hz), 7.18–7.23 (m, 2H), 7.45–7.48 (d, 1H, J=8.7 Hz), 7.94–7.98 (d, 1H, J=9.3 Hz), 8.21–8.24 (d, 1H, J=9.6 Hz), 8.40 (s, 1H), 8.84 (s, 1H), 10.63 (s, 1H), 11.97 (s, 1H). MS (ESI) 510(M+H )$^+$, 532 (M+Na)$^+$.

EXAMPLE 54

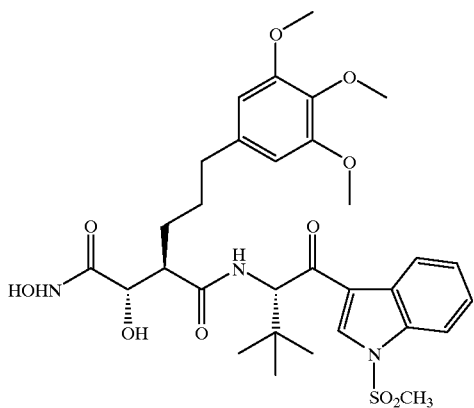

EXAMPLE 54A

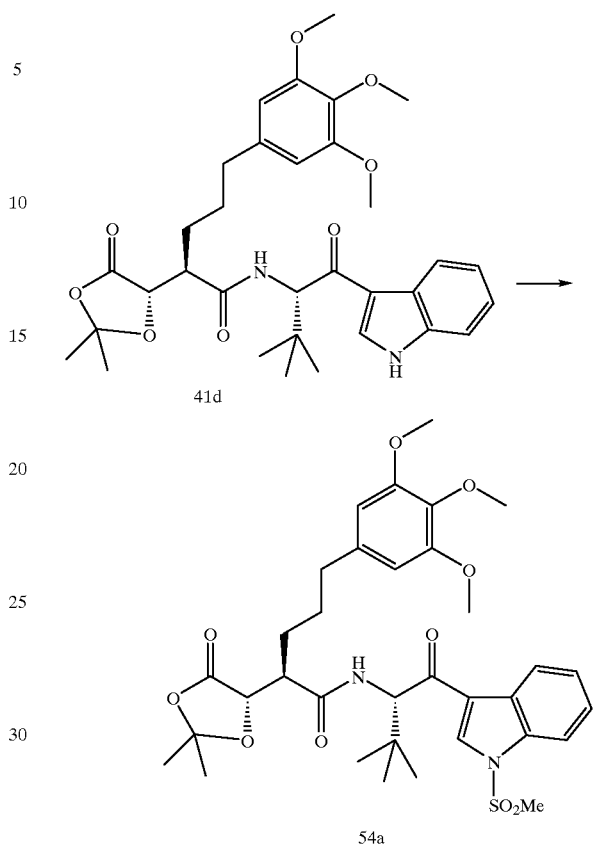

A solution of 41d (249 mg, 0.419 mmol) in dichloromethane (5 mL) at room temperature was treated with methanesulfonyl chloride (144.2 mg, 97.4 ml, 1.26 mmol), and triethylamine (127 mg, 175 ml, 1.26 mmol), stirred for 6 hours, and quenched with water, extracted with dichloromethane, dried (Na$_2$SO$_4$) and concentrated. The residue was purified on silica gel with 40% to 60% ethyl acetate/hexane to provide 239.4 mg (85%) of 54a as a white foam. MS (ESI) m/e 673 (M+H)$^+$.

EXAMPLE 54B

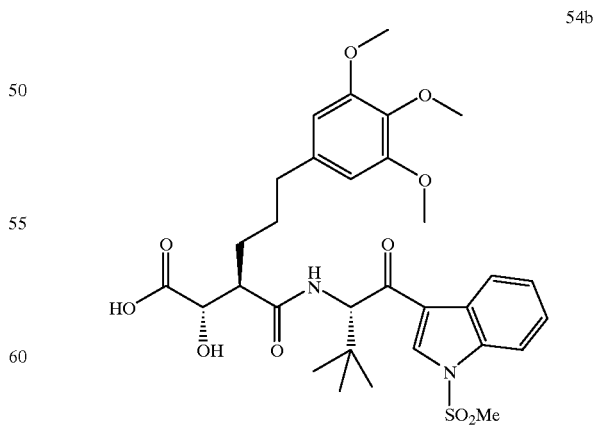

A solution of 54a (237 mg, 0.353 mmol) in THF (4.5 mL) at 0° C. was treated with 1N HCl (4.5 mL), stirred at room temperature for 17 hours, and concentrated. The residue was extracted with dichloromethane, dried (Na$_2$SO$_4$), and concentrated. The residue was purified on silica gel with 0.1% acetic acid in 10% MeOH/CH$_2$Cl$_2$ to provide 177 mg (79%) of 54b as a white solid. MS (ESI) m/e 631 (M−H)$^-$.

EXAMPLE 54C

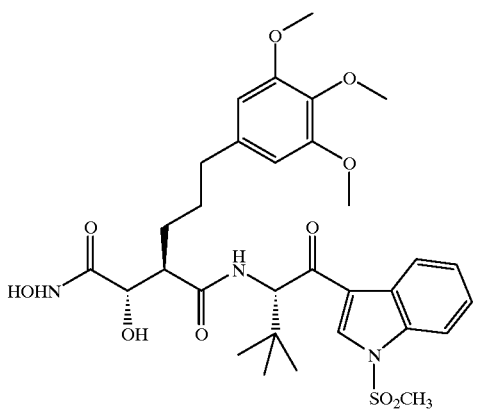

The desired compound was prepared according to the method of Examples 5A–B, except substituting 54b for 4. 1H NMR (DMSO-d6) δ1.004 (s, 9H), 1.247–1.347 (m, 4H), 2.269–2.418 (m, 2H), 2.800–2.833 (m, 1H), 3.554 (s, 3H), 3.593 (s, 6H), 3.649 (s, 3H), 3.768–3.822 (1H), 5.100–5.127 (d, 1H, J=8.1 Hz), 5.232–5.256 (d, 1H, J=7.2 Hz), 6.301 (s, 2H), 7.403–7.464 (m, 2H), 7.874–7.900 (d, 1H, J=7.8 Hz), 8.136–8.165 (d, 1H, J=8.7 Hz), 8.215–8.240 (d, 1H, J=7.5 Hz), 8.634 (s, 1H), 8.855 (s, 1H), 10.652 (s, 1H). MS (ESI) 648 (M+H)$^+$, 665 (M+NH4)$^+$.

We claim:
1. A compound of formula

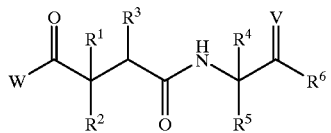

or pharmaceutically acceptable salt, ester or prodrug thereof wherein
W is NHOH or —OH;
R$^1$ and R$^4$ are independently selected at each occurrence from hydrogen or alkyl of one to four carbon atoms;
V is O or NOR$^1$;
R$^2$ is selected from the group consisting of
(a) hydrogen,
(b) hydroxy,
(c) alkoxy of one to six carbon atoms,
(d) alkyl of one to six carbon atoms,
(e) alkyl of one to six carbon atoms substituted with
 (1) halogen,
 (2) hydroxy,
 (3) alkoxy of one to six carbon atoms,
 (4) cycloalkyl of three to eight carbon atoms,
 (5) alkanoyloxy wherein the alkyl portion is of one to four carbon atoms,
 (6) pyridyl,
 (7) pyridyl substituted with alkyl of one to four carbon atoms,
 (8) phenoxy wherein the phenyl ring is unsubstituted or substituted with 1, 2 or 3 substituents independently selected from
  alkyl of one to four carbon atoms,
  hydroxy,
  alkoxy of one to four carbon atoms,
  halogen,
  haloalkyl of one to four carbon atoms,
  cyano,
  cyanoalkyl,
  —CO$_2$R$^7$ wherein R$^7$ is hydrogen or alkyl of one to four carbon atoms,
  —CONR$^7$R$^8$ wherein R$^7$ is defined above and R$^8$ is selected from
   hydrogen,
   alkanoyl of one to four carbon atoms,
   alkyl of one to four carbon atoms,
   phenyl, and
   phenyl substituted with 1, 2, or 3 substituents independently selected from alkyl of one to four carbon atoms,
    hydroxy,
    alkoxy of one to four carbon atoms,
    halogen,
    haloalkyl of one to four carbon atoms,
    cyano,
    cyanoalkyl,
   —CONR$^9$R$^{10}$ wherein R$^9$ and R$^{10}$ are independently selected from hydrogen and alkyl of one to four carbon atoms, and
   —CO$_2$R$^9$, and (9)

[structure]

(10) —S(O)$_n$R$^{11}$ wherein n is 0, 1 or 2 and R$^{11}$ is selected from
 (a) alkyl of one to six carbon atoms,
 (b) phenyl,
 (c) phenyl substituted with 1, 2 or 3 substituents independently selected from
  alkyl of one to four carbon atoms,
  hydroxy,
  alkoxy of one to four carbon atoms,
  halogen,
  haloalkyl of one to four carbon atoms,
  cyano,
  cyanoalkyl,
  —CO$_2$R$^7$,
  —CONR$^7$R$^8$,
 (d) thienyl,
 (e) thienyl substituted with alkyl of one to four carbon atoms,
 (f) phenylalkyl wherein the alkyl portion is of one to four carbon atoms,
 (g) phenylalkyl wherein the alkyl portion is of one to four carbon atoms, and the phenyl ring is substituted with 1, 2 or 3 substituents independently selected from alkyl of one to four carbon atoms,
  hydroxy,
  alkoxy of one to four carbon atoms,
  halogen,
  haloalkyl of one to four carbon atoms, cyano,
cyanoalkyl,
—CO$_2$R$^7$, and
—CONR$^7$R$^8$,
(h) thienylalkyl wherein the alkyl portion is of one to four carbon atoms, and
(i) thienylalkyl wherein the alkyl portion is of one to four carbon atoms and the thienyl ring is substituted with alkyl of one to four carbon atoms, and
(11) —NR$^{12}$R$^{13}$ wherein R$^{12}$ is hydrogen or alkyl of one to four carbon atoms and R$^{13}$ is selected from
(a) hydrogen,
(b) alkyl of one to four carbon atoms,
(c) —CO$_2$R$^{14}$ wherein R$^{14}$ is independently selected at each occurrence from alkyl of one to four carbon atoms,
haloalkyl of one to four carbon atoms,
phenyl,
phenyl substituted with 1, 2, or 3 substituents independently selected from alkyl of one to four carbon atoms,
alkoxy of one to four carbon atoms,
halogen,
haloalkyl of one to four carbon atoms,
nitro,
cyano,
cyanoalkyl,
—SO$_2$NH$_2$,
—CO$_2$R$^7$, and
—CONR$^7$R$^8$,
phenylalkyl wherein the alkylene portion is of one to four carbon atoms,
phenylalkyl wherein the alkylene portion is of one to four carbon atoms, and the phenyl ring is substituted with 1, 2, or 3 substituents independently selected from
alkyl of one to four carbon atoms,
alkoxy of one to four carbon atoms,
halogen,
haloalkyl of one to four carbon atoms,
cyano,
cyanoalkyl,
—SO$_2$NH$_2$,
—CO$_2$R$^7$, and
—CONR$^7$R$^8$,
heteroarylalkyl wherein the alkylene portion is of one to four carbon atoms, and the heteroaryl group is selected from
furyl,
pyridyl,
thienyl,
benzimidazolyl,
imidazolyl,
thiazolyl, and
benzothiazolyl
wherein the heteroaryl group is unsubstituted or substituted with alkyl of one to four carbon atoms, and
(d) —SO$_2$R$^{14}$,
or R$^{12}$ and R$^{13}$, together with the N atoms to which they are attached define a heterocycle selected from
morpholinyl,
thiomorpholinyl,
thiomorpholinyl sulfone,
pyrrolidinyl,
piperazinyl,
piperidinyl,
succinimidyl,
maleimidyl,
glutarimidyl,
phthalimidyl,
naphthalimidyl,

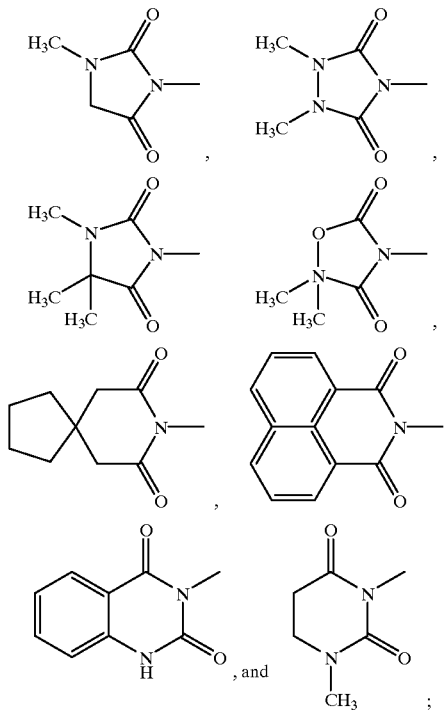

(f) alkenyl of two to six carbon atoms,
(g) alkenyl of two to six carbon atoms substituted with
(1) halogen,
(2) hydroxy,
(3) alkoxy of one to six carbon atoms,
(4) cycloalkyl of three to eight carbon atoms,
(5) alkanoyloxy wherein the alkyl portion is of one to four carbon atoms,
(6) pyridyl,
(7) pyridyl substituted with alkyl of one to four carbon atoms,
(8) phenoxy wherein the phenyl ring is unsubstituted or substituted with 1, 2 or 3 substituents independently selected from
alkyl of one to four carbon atoms,
hydroxy,
alkoxy of one to four carbon atoms,
halogen,
haloalkyl of one to four carbon atoms,
cyano,
cyanoalkyl,
—CO$_2$R$^7$,
—CONR$^7$R$^8$,
phenyl, and
phenyl substituted with 1, 2, or 3 substituents independently selected from alkyl of one to four carbon atoms,
hydroxy,
alkoxy of one to four carbon atoms,
halogen,
haloalkyl of one to four carbon atoms, cyano,
cyanoalkyl,
—CO$_2$R$^9$, and
—CONR$^9$R$^{10}$, (9) 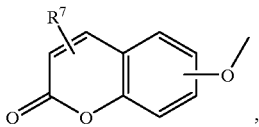

(10) —S(O)$_n$R$^{11}$ and
(11) —NR$^{12}$R$^{13}$;

R$^3$ is selected from the group consisting of
(a) alkyl of one to ten carbon atoms,
(b) alkenyl of two to ten carbon atoms,
(c) cycloalkyl of three to eight carbon atoms,
(d) (cycloalkyl)alkyl wherein the cycloalkyl portion is of three to eight carbon atoms, and the alkylene portion is of one to six carbon atoms,
(e) cycloalkylene of five to eight carbon atoms,
(f) (cycloalkylene)alkyl wherein the cycloalkylene portion is of three to eight carbon atoms, and the alklene portion is of one to six carbon atoms,
(g) phenyl wherein the phenyl ring is unsubstituted or substituted with 1, 2 or 3 substituents independently selected from
alkyl of one to four carbon atoms,
alkoxy of one to four carbon atoms,
halogen,
haloalkyl of one to four carbon atoms,
cyano,
cyanoalkyl,
—CO$_2$R$^7$,
—CO$_2$NR$^7$R$^8$,
phenyl substituted with 1, 2, or 3 substituents independently selected from alkyl of one to four carbon atoms,
hydroxy,
alkoxy of one to four carbon atoms,
halogen,
haloalkyl of one to four carbon atoms,
cyano,
cyanoalkyl,
—CO$_2$R$^9$, and
—CONR$^9$R$^{10}$,
(h) phenylalkyl wherein the alkylene portion is of one to six carbon atoms, and the phenyl ring is unsubstituted or substituted with 1, 2 or 3 substituents independently selected from
alkyl of one to four carbon atoms,
alkoxy of one to four carbon atoms,
halogen,
haloalkyl of one to four carbon atoms,
cyano,
cyanoalkyl,
—CO$_2$R$^7$,
—CO$_2$NR$^7$R$^8$,
alkoxyalkyloxy,
phenyl, and
phenyl substituted with 1, 2, or 3 substituents independently selected from
alkyl of one to four carbon atoms,
alkoxy of one to four carbon atoms,
halogen,
haloalkyl of one to four carbon atoms,
cyano,
cyanoalkyl,
—CO$_2$R$^7$ and
—CO$_2$NR$^7$R$^8$,
(i) —(CH$_2$)$_m$—T—(CH$_2$)$_n$—R$^{15}$ wherein m and n are independently 0, 1, 2, 3 or 4,
T is O or S, and
R$^{15}$ is selected from the group consisting of
alkyl of one to four carbon atoms,
phenyl, and
phenyl substituted with 1, 2, or 3 substituents selected from
alkyl of one to four carbon atoms,
hydroxy,
alkoxy of one to four carbon atoms,
alkoxyalkyloxy
halogen,
haloalkyl of one to four carbon atoms,
cyano,
cyanoalkyl,
—CO$_2$R$^7$, and
—CONR$^7$R$^8$,
phenyl, and
phenyl substituted with 1, 2, or 3 substituents independently selected from
alkyl of one to four carbon atoms,
hydroxy,
alkoxy of one to four carbon atoms,
halogen,
haloalkyl of one to four carbon atoms,
cyano,
cyanoalkyl,
—CO$_2$R$^7$,
—CONR$^7$R$^8$, and
(j) fluorenylalkyl wherein the alkylene portion is of one to four carbon atoms,
R$^5$ is selected from the group consisting of
(a) alkyl of one to six carbon atoms,
(b) alkyl of one to six carbon atoms substituted with cycloalkyl of three to eight carbon atoms,
hydroxy,
alkoxy,
—SR$^7$,
—NR$^7$R$^8$,
—CO$_2$R$^7$,
—CONR$^7$R$^8$,
guanidyl,
phenyl,
phenyl substituted with 1, 2, or 3 substituents independently selected from
alkyl of one to four carbon atoms,
hydroxy,
alkoxy of one to four carbon atoms,
halogen,
haloalkyl of one to four carbon atoms,
nitro,
cyano,
cyanoalkyl,
carboxyalkyloxy,
—S(O)$_n$R$^{16}$ wherein n is 0, 1 or 2 and R$^{16}$ is alkyl of one to four carbon atoms, —$SO_2NH_2$,
—$CO_2R^7$, and
—$CONR^7R^8$, and
phenyl substituted with 1, 2, or 3 substituents independently selected from
  alkyl of one to four carbon atoms,
  hydroxy,
  alkoxy of one to four carbon atoms,
  halogen, and
  haloalkyl of one to four carbon atoms,
naphthyl,
naphthyl substituted with 1, 2, or 3 substituents independently selected from
  alkyl of one to four carbon atoms,
  hydroxy,
  alkoxy of one to four carbon atoms,
  halogen,
  haloalkyl of one to four carbon atoms,
indolyl,
indolyl substituted with
  alkyl of one to four carbon atoms,
  hydroxy,
  alkoxy of one to four carbon atoms,
  halogen,
  haloalkyl of one to four carbon atoms,
  —$SO_2R^{13}$,
  —$SO_2NH_2$,
  —$CO_2R^7$ and
  —$CONR^7R^8$,
pyridyl,
pyridyl substituted with alkyl of one to four carbon atoms,
pyrazolyl,
pyrazolyl substituted with alkyl of one to four carbon atoms,
5-oxadiazolyl,
imidazolyl, and
imidazolyl substituted with alkyl of one to four carbon atoms,
(c) phenyl and
(d) phenyl substituted with 1, 2, or 3 substituents independently selected from
  alkyl of one to four carbon atoms,
  hydroxy,
  alkoxy of one to four carbon atoms,
  halogen, and
  haloalkyl of one to four carbon atoms;
$R^6$ is selected from the group consisting of
  (a) alkyl of one to six carbon atoms,
  (b) alkyl of one to six carbon atoms substituted with
  hydroxy,
  alkoxy,
  halogen, and
  —$CO_2R^{17}$ wherein $R^{17}$ is selected from
    hydrogen,
    alkyl of one to four carbon atoms and
    alkenyl of two to four carbon atoms,
  (c) phenyl,
  (d) phenyl substituted with 1, 2, or 3 substituents selected from
    alkyl of one to four carbon atoms,
    halogen,
    hydroxy,
    hydroxyalkyl of one to four carbon atoms,
    haloalkyl of one to four carbon atoms,
    alkoxy of one to four carbon atoms,
    cyano,
    —$NR^7R^8$,
    —$SO_2NR^7R^8$,
    —$SO_2R^{16}$,
    —$CH_2NR^{18}R^{19}$, wherein $R^{18}$ and $R^{19}$ are independently selected at each occurrence from hydrogen and alkyl of one to four carbon atoms,
      or $R^{18}$ and $R^{19}$ together with the N atom to which they are attached define a a 5- or 6-membered heterocyclic ring selected from
    (1) morpholinyl,
    (2) thiomorpholinyl,
    (3) thiompholinyl sulfone,
    (4) pyrrolidinyl,
    (5) piperazinyl,
    (6) 3-ketopiperazinyl and
    (7) piperidinyl,
    —$CONR^7R^8$,
    —$CO_2R^7$, and
    phenyl, wherein the phenyl ring may be substituted with 1, 2, or 3 substituents selected from
      alkyl of one to four carbon atoms,
      halogen, and
      haloalkyl of one to four carbon atoms,
  (e) 1,3-benzodioxole,
  (f) indolyl,
  (g) indolyl substituted with
    alkyl of one to four carbon atoms,
    halogen,
    haloalkyl of one to four carbon atoms,
    alkoxy of one to four carbon atoms,
    —$SO_2NR^7R^8$,
    —$CO_2R^7$, and
    phenyl, wherein the phenyl ring may be substituted with 1, 2, or 3 substituents selected from
      alkyl of one to four carbon atoms,
      halogen,
      haloalkyl of one to four carbon atoms, and
      alkoxy of one to four carbon atoms,
  (h) pyrrolyl,
  (i) pyrrolyl substituted with alkyl of one to four carbon atom
  (j) imidazolyl,
  (k) imidazolyl substituted with alkyl of one to four carbon atoms,
  (l) benzimidazolyl,
  (m) benzimidazolyl substituted with 1, 2 or 3 substituents independently selected from
    alkyl of one to four carbon atoms,
    halogen and
    haloalkyl of one to four carbon atoms,
provided that in (f)–(m) above, when the heterocycle is attached at a carbon atom, the N atom may bear a substituent selected from the group consisting of
  alkyl of one to six carbon atoms
  —$CONR^7R^8$,
  —$SO_2NR^7R^8$ and —SO$_2$R$^{14}$,
(n) pyridyl,
(o) pyridyl substituted with alkyl of one to four carbon atoms,
(p) thienyl,
(q) thienyl substituted with
   halogen,
   alkyl of one to four carbon atoms, and
   haloalkyl of one to four carbon atoms,
(r) thiazolyl,
(s) thiazolyl substituted with
   halogen,
   alkyl of one to four carbon atoms, and
   haloalkyl of one to four carbon atoms,
(t) oxazolyl,
(u) oxazolyl substituted with
   halogen,
   alkyl of one to four carbon atoms, and
   haloalkyl of one to four carbon atoms,
(v) furyl,
(w) furyl substituted with
   halogen,
   alkyl of one to four carbon atoms, and
   haloalkyl of one to four carbon atoms,
(x) benzofuryl,
(y) benzofuryl substituted with 1, 2, or 3 substituents selected from
   alkyl of one to four carbon atoms,
   halogen, and
   haloalkyl of one to four carbon atoms,
(z) benzothiazolyl, and
(aa) benzothiazolyl substituted with 1, 2, or 3 substituents selected from
   alkyl of one to four carbon atoms,
   halogen, and
   haloalkyl of one to four carbon atoms.

2. A compound pharmaceutically acceptable salt, ester or prodrug thereof as defined in claim 1 wherein R$^6$ is selected from the group consisting of
(a) alkyl of one to six carbon atoms, and
(b) alkyl of one to six carbon atoms substituted with
   hydroxy,
   alkoxy,
   halogen, and
   —CO$_2$R$^{17}$ wherein R$^{17}$ is selected from
      hydrogen,
      alkyl of one to four carbon atoms and
      alkenyl of two to four carbon atoms.

3. A compound pharmaceutically acceptable salt, ester or prodrug thereof as defined in claim 1 wherein R$^6$ is selected from the group consisting of
(c) phenyl,
(d) phenyl substituted with 1, 2, or 3 substituents selected from
   alkyl of one to four carbon atoms,
   halogen,
   hydroxy,
   hydroxyalkyl of one to four carbon atoms,
   haloalkyl of one to four carbon atoms,
   alkoxy of one to four carbon atoms,
   cyano,
   —NR$^7$R$^8$,
   —SO$_2$NR$^7$R$^8$,
   —SO$_2$R$^{16}$,
   —CH$_2$NR$^{18}$R$^{19}$, wherein R$^{18}$ and R$^{19}$ are independently selected at each occurrence from hydrogen and alkyl of one to four carbon atoms,
      or R$^{18}$ and R$^{19}$ together with the N atom to which they are attached define a a 5- or 6-membered heterocyclic ring selected from
      (1) morpholinyl,
      (2) thiomorpholinyl,
      (3) thiompholinyl sulfone,
      (4) pyrrolidinyl,
      (5) piperazinyl,
      (6) 3-ketopiperazinyl and
      (7) piperidinyl,
   —CONR$^7$R$^8$,
   —CO$_2$R$^7$, and
   phenyl, wherein the phenyl ring may be substituted with 1, 2, or 3 substituents selected from
      alkyl of one to four carbon atoms,
      halogen, and
      haloalkyl of one to four carbon atoms, and
(e) 1,3-benzodioxole.

4. A compound pharmaceutically acceptable salt, ester or prodrug thereof as defined in claim 1 wherein R$^6$ is selected from the group consisting of
(f) indolyl,
(g) indolyl substituted with
   alkyl of one to four carbon atoms,
   halogen,
   haloalkyl of one to four carbon atoms,
   alkoxy of one to four carbon atoms,
   —SO$_2$NR$^7$R$^8$,
   —CO$_2$R$^7$, and
   phenyl, wherein the phenyl ring may be substituted with 1, 2, or 3 substituents selected from
      alkyl of one to four carbon atoms,
      halogen,
      haloalkyl of one to four carbon atoms, and
      alkoxy of one to four carbon atoms,
(h) pyrrolyl,
(i) pyrrolyl substituted with alkyl of one to four carbon atom
(j) imidazolyl,
(k) imidazolyl substituted with alkyl of one to four carbon atoms,
(l) benzimidazolyl,
(m) benzimidazolyl substituted with 1, 2 or 3 substituents independently selected from
   alkyl of one to four carbon atoms,
   halogen and
   haloalkyl of one to four carbon atoms,
provided that in (f)—(m) above, when the heterocycle is attached at a carbon atom, the N atom may bear a substituent selected from the group consisting of
   alkyl of one to six carbon atoms
   —CONR$^7$R$^8$,
   —SO$_2$NR$^7$R$^8$ and
   —SO$_2$R$^{14}$,
(n) pyridyl,
(o) pyridyl substituted with alkyl of one to four carbon atoms, (p) thienyl,
(q) thienyl substituted with
  halogen,
  alkyl of one to four carbon atoms, and
  haloalkyl of one to four carbon atoms,
(r) thiazolyl,
(s) thiazolyl substituted with
  halogen,
  alkyl of one to four carbon atoms, and
  haloalkyl of one to four carbon atoms,
(t) oxazolyl,
(u) oxazolyl substituted with
  halogen,
  alkyl of one to four carbon atoms, and
  haloalkyl of one to four carbon atoms,
(v) furyl,
(w) furyl substituted with
  halogen,
  alkyl of one to four carbon atoms, and
  haloalkyl of one to four carbon atoms,
(x) benzofuryl,
(y) benzofuryl substituted with 1, 2, or 3 substituents selected from
  alkyl of one to four carbon atoms,
  halogen, and
  haloalkyl of one to four carbon atoms,
(z) benzothiazolyl, and
(aa) benzothiazolyl substituted with 1, 2, or 3 substituents selected from
  alkyl of one to four carbon atoms,
  halogen, and
  haloalkyl of one to four carbon atoms.

5. A compound pharmaceutically acceptable salt, ester or prodrug thereof as defined in claim 1 wherein
$R^1$ and $R^4$ are hydrogen;
$R^2$ is selected from the group consisting of
(a) hydrogen,
(b) hydroxy,
(c) alkoxy of one to six carbon atoms,
(d) alkyl of one to six carbon atoms,
(e) alkyl of one to six carbon atoms substituted with

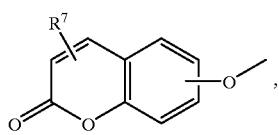
(1)

(2) —S(O)$_n$R$^{11}$ wherein n is 0, 1 or 2 and R$^{11}$ is selected from
  (a) phenyl,
  (b) phenyl substituted with 1, 2 or 3 substituents independently selected from
    alkyl of one to four carbon atoms,
    hydroxy,
    alkoxy of one to four carbon atoms,
    halogen,
    haloalkyl of one to four carbon atoms,
    cyano,
    cyanoalkyl,
    —CO$_2$R$^7$,
    —CONR$^7$R$^8$,
  (c) thienyl and
  (d) thienyl substituted with alkyl of one to four carbon atoms and
(3) —NR$^{12}$R$^{13}$ wherein R$^{12}$ and R$^{13}$ are independently selected from hydrogen and alkyl of one to four carbon atoms and
  or R$^{12}$ and R$^{13}$, together with the N atoms to which they are attached define a heterocycle of formula

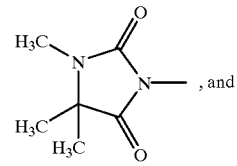
, and (f) alkenyl of two to six carbon atoms;
$R^3$ is selected from the group consisting of
(a) alkyl of one to ten carbon atoms,
(b) cycloalkyl of three to eight carbon atoms, and
(c) phenylalkyl wherein the alkylene portion is of one to six carbon atoms, and the phenyl ring is unsubstituted or substituted with 1, 2 or 3 substituents independently selected from
  alkyl of one to four carbon atoms,
  alkoxy of one to four carbon atoms,
  halogen,
  haloalkyl of one to four carbon atoms,
  cyano,
  cyanoalkyl,
  —CO$_2$R$^7$,
  —CO$_2$NR$^7$R$^8$,
  phenyl, and
  phenyl substituted with 1, 2, or 3 substituents independently selected from
    alkyl of one to four carbon atoms,
    alkoxy of one to four carbon atoms,
    halogen,
    haloalkyl of one to four carbon atoms,
    cyano,
    cyanoalkyl,
    —CO$_2$R$^7$ and
    —CO$_2$NR$^7$R$^8$; and
$R^5$ is selected from the group consisting of
(a) alkyl of one to six carbon atoms,
(b) alkyl of one to six carbon atoms substituted with
  cycloalkyl of three to eight carbon atoms,
  —CO$_2$R$^7$,
  —SR$^7$,
  phenyl, and
  phenyl substituted with 1, 2, or 3 substituents independently selected from
    alkyl of one to four carbon atoms,
    hydroxy,
    alkoxy of one to four carbon atoms,
    halogen,
    haloalkyl of one to four carbon atoms,
    nitro,
    cyano,
    cyanoalkyl,
    —S(O)$_n$R$^{16}$ wherein n is 0, 1 or 2 and R$^{16}$ is alkyl of one to four carbon atoms,
    —SO$_2$NH$_2$, —CO$_2$R$^7$, and
—CONR$^7$R$^8$.

6. A compound pharmaceutically acceptable salt, ester or prodrug thereof as defined by claim 5 wherein W is NHOH and V is O.

7. A compound pharmaceutically acceptable salt, ester or prodrug thereof as defined in claim 6 wherein
R$^2$ is selected from the group consisting of
hydrogen,
hydroxy,
alkenyl of two to six carbon atoms;
R$^3$ is selected from the group consisting of
isobutyl,
cyclohexyl,
3-phenylpropyl,
3-(4-tolyl)propyl,
biphenyloxy,
4-(phenylmethoxy)butyl,
4-(3,4,5-trimethoxyphenyl)butyl, and
3-(3,4,5-trimethoxyphenyl)propyl;
R$^5$ is selected from the group consisting of
(a) alkyl of one to six carbon atoms,
(b) alkyl of one to six carbon atoms substituted with
   cycloalkyl of three to eight carbon atoms,
   carboxy,
   phenyl, and
   hydroxyphenyl.

8. A compound or pharmaceutically acceptable salt, ester or prodrug thereof as defined by claim 7 wherein
R$^6$ is selected from the group consisting of
(a) alkyl of one to six carbon atoms,
(b) alkyl of one to six carbon atoms substituted with —CO$_2$R$^{17}$,
(c) phenyl,
(d) phenyl substituted with 1, 2, or 3 substituents selected from
   alkyl of one to four carbon atoms,
   halogen,
   hydroxy,
   hydroxyalkyl of one to four carbon atoms,
   haloalkyl of one to four carbon atoms,
   alkoxy of one to four carbon atoms,
   —NR$^7$R$^8$,
   cyano,
   —SO$_2$NR$^7$R$^8$,
   —SO$_2$R$^{16}$,
   —CH$_2$NR$^{18}$R$^{19}$,
   —CONR$^7$R$^8$ and
   —CO$_2$R$^7$,
(e) indolyl,
(f) indolyl substituted with
   alkyl of one to four carbon atoms,
   halogen,
   haloalkyl of one to four carbon atoms,
   alkoxy of one to four carbon atoms and
   phenyl, wherein the phenyl ring may be substituted with 1, 2, or 3 substituents selected from
      alkyl of one to four carbon atoms,
      halogen,
      haloalkyl of one to four carbon atoms, and
      alkoxy of one to four carbon atoms,
(g) pyrrolyl,
(h) pyrrolyl substituted with alkyl of one to four carbon atoms,
(i) benzimidazolyl,
(j) benzimidazolyl substituted with 1, 2 or 3 substituents independently selected from
   alkyl of one to four carbon atoms,
   halogen and
   haloalkyl of one to four carbon atoms,
   provided that in (e)–(j) above, when the heterocycle is attached at a carbon atom,
the N atom may bear a substituent selected from the group consisting of
   alkyl of one to six carbon atoms,
   —SO$_2$R$^{14}$,
   —CONR$^7$R$^8$ and
   —SO$_2$NR$^7$R$^8$,
(k) thienyl,
(l) thienyl substituted with
   halogen,
   alkyl of one to four carbon atoms, and
   haloalkyl of one to four carbon atoms,
(m) thiazolyl,
(n) thiazolyl substituted with
   halogen,
   alkyl of one to four carbon atoms, and
   haloalkyl of one to four carbon atoms,
(o) oxazolyl and
(p) oxazolyl substituted with
   halogen,
   alkyl of one to four carbon atoms, and
   haloalkyl of one to four carbon atoms.

9. A compound or pharmaceutically acceptable salt, ester or prodrug thereof as defined by claim 8 wherein
R$^6$ is selected from the group consisting of
(a) phenyl,
(b) phenyl substituted with 1, 2, or 3 substituents selected from
   alkyl of one to four carbon atoms,
   halogen,
   hydroxy,
   hydroxyalkyl of one to four carbon atoms,
   haloalkyl of one to four carbon atoms,
   alkoxy of one to four carbon atoms,
   —NR$^7$R$^8$,
   cyano,
   —SO$_2$NR$^7$R$^8$,
   —SO$_2$R$^{16}$,
   —CH$_2$NR$^{18}$R$^{19}$,
   —CONR$^7$R$^8$ and
   —CO$_2$R$^7$,
(c) indolyl,
(d) indolyl substituted with
   alkyl of one to four carbon atoms,
   halogen,
   haloalkyl of one to four carbon atoms,
   alkoxy of one to four carbon atoms and
   phenyl, wherein the phenyl ring may be substituted with 1, 2, or 3 substituents selected from
      alkyl of one to four carbon atoms, halogen,
haloalkyl of one to four carbon atoms, and
alkoxy of one to four carbon atoms,
(e) pyrrolyl,
(f) pyrrolyl substituted with alkyl of one to four carbon atoms,
(g) benzimidazolyl,
(h) benzimidazolyl substituted with 1, 2 or 3 substituents independently selected from
alkyl of one to four carbon atoms,
halogen and
haloalkyl of one to four carbon atoms,
provided that in (c)–(h) above, when the heterocycle is attached at a carbon atom,
the N atom may bear a substituent selected from the group consisting of
alkyl of one to six carbon atoms,
—$SO_2R^{14}$,
—$CONR^7R^8$ and
—$SO_2NR^7R^8$,
(i) thienyl,
(j) thienyl substituted with
halogen,
alkyl of one to four carbon atoms, and
haloalkyl of one to four carbon atoms,
(k) thiazolyl,
(l) thiazolyl substituted with
halogen,
alkyl of one to four carbon atoms, and
haloalkyl of one to four carbon atoms,
(m) oxazolyl and
(n) oxazolyl substituted with
halogen,
alkyl of one to four carbon atoms, and
haloalkyl of one to four carbon atoms.

10. A compound or pharmaceutically acceptable salt, ester or prodrug thereof as defined by claim 9 wherein $R^6$ is selected from the group consisting of
(a) phenyl and
(b) phenyl substituted with 1, 2, or 3 substituents selected from
alkyl of one to four carbon atoms,
halogen,
hydroxy,
hydroxyalkyl of one to four carbon atoms,
haloalkyl of one to four carbon atoms,
alkoxy of one to four carbon atoms,
—$NR^7R^8$,
cyano,
—$SO_2NR^7R^8$,
—$SO_2R^{16}$,
—$CH_2NR^{18}R^{19}$,
—$CONR^7R^8$, and
—$CO_2R^7$.

11. A compound or pharmaceutically acceptable salt, ester or prodrug thereof as defined by claim 1 selected from the group consisting of

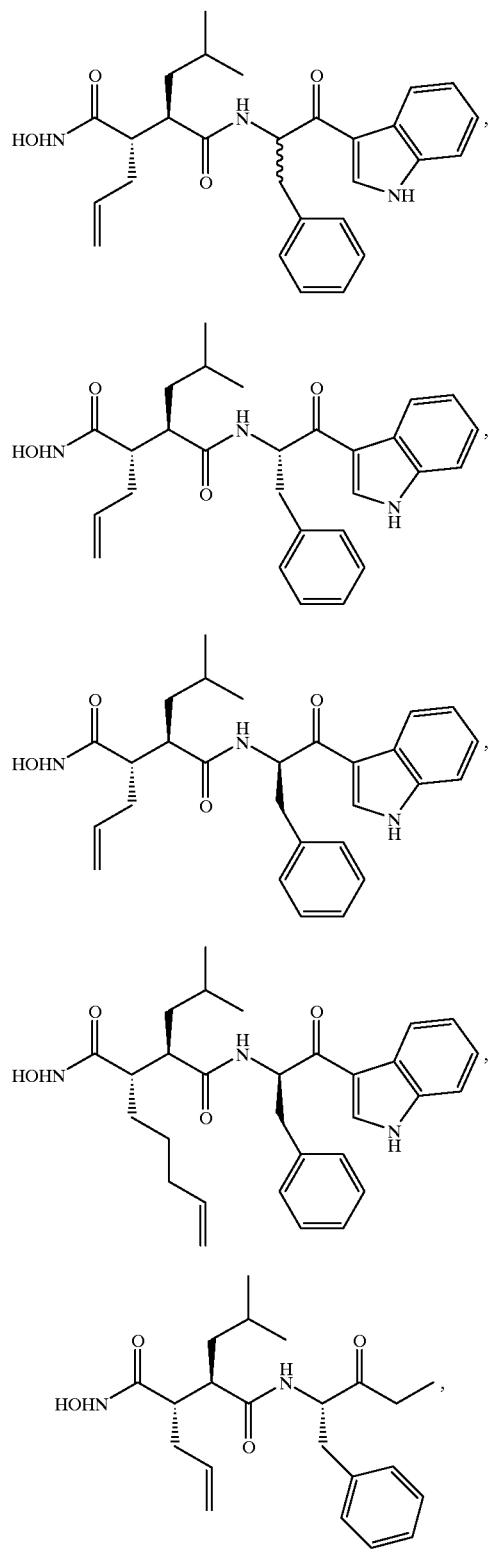

121
-continued
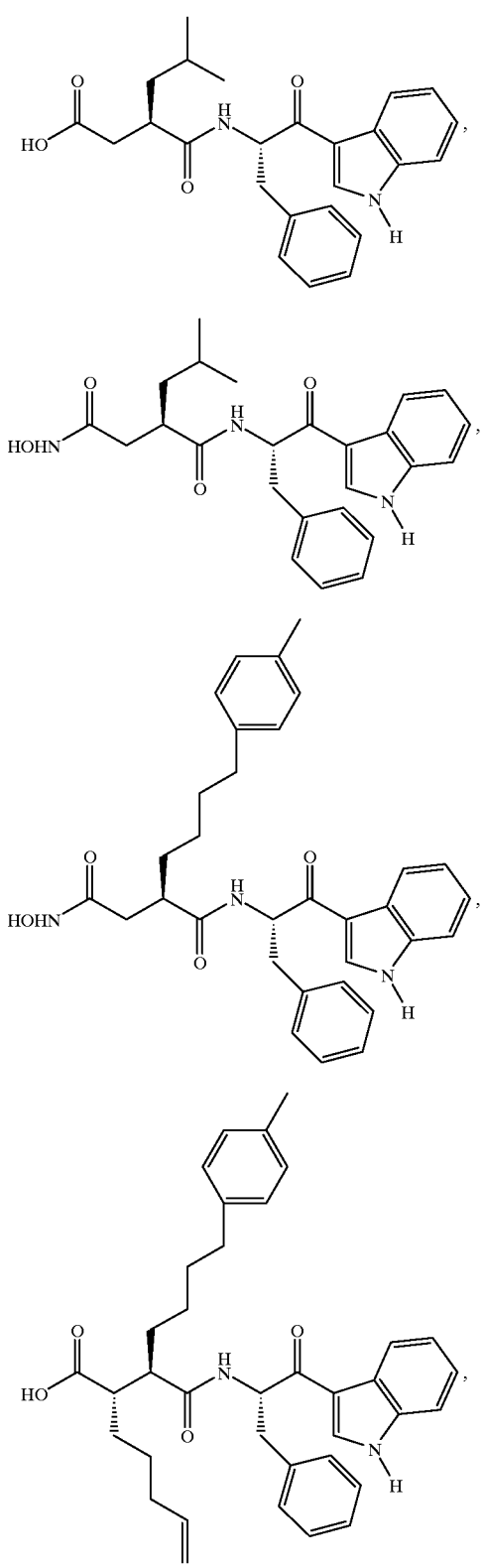
122
-continued
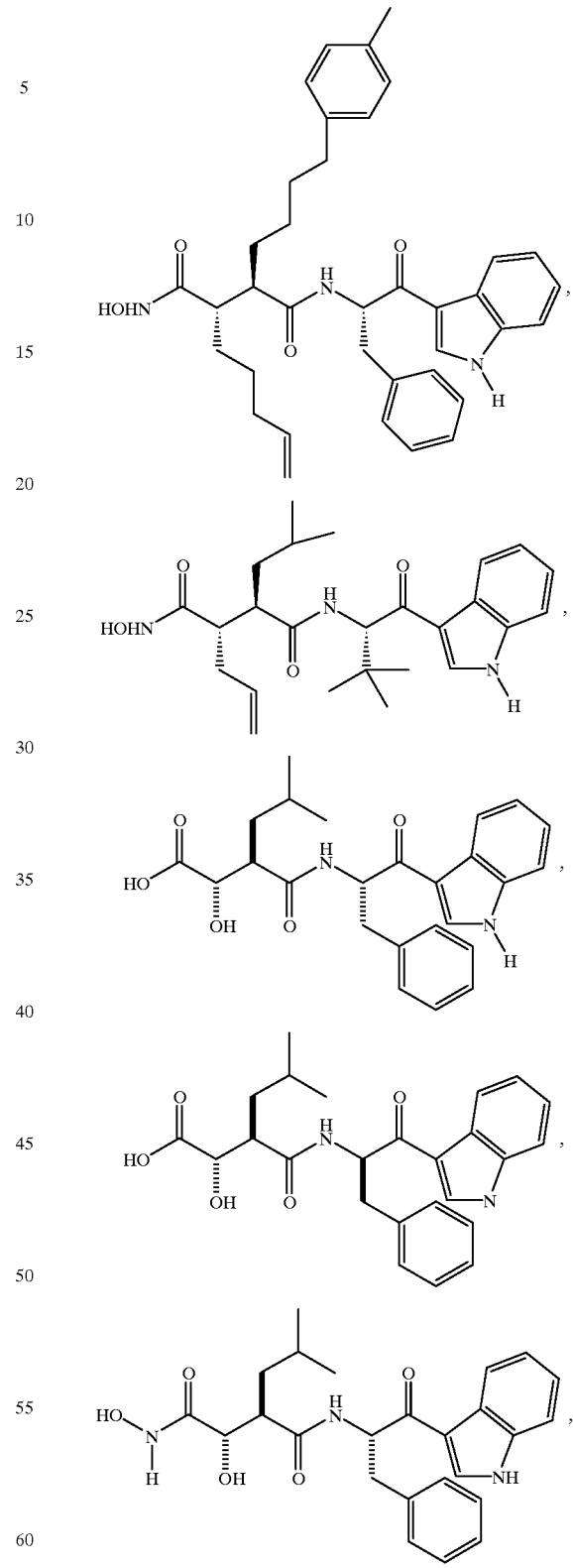

123
-continued
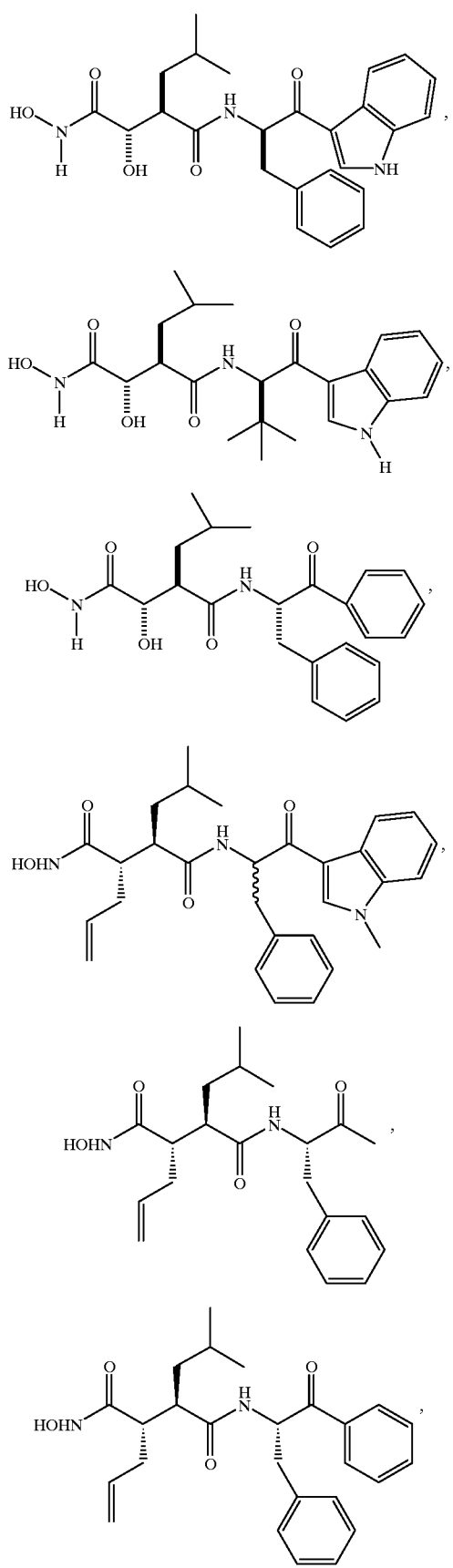
124
-continued
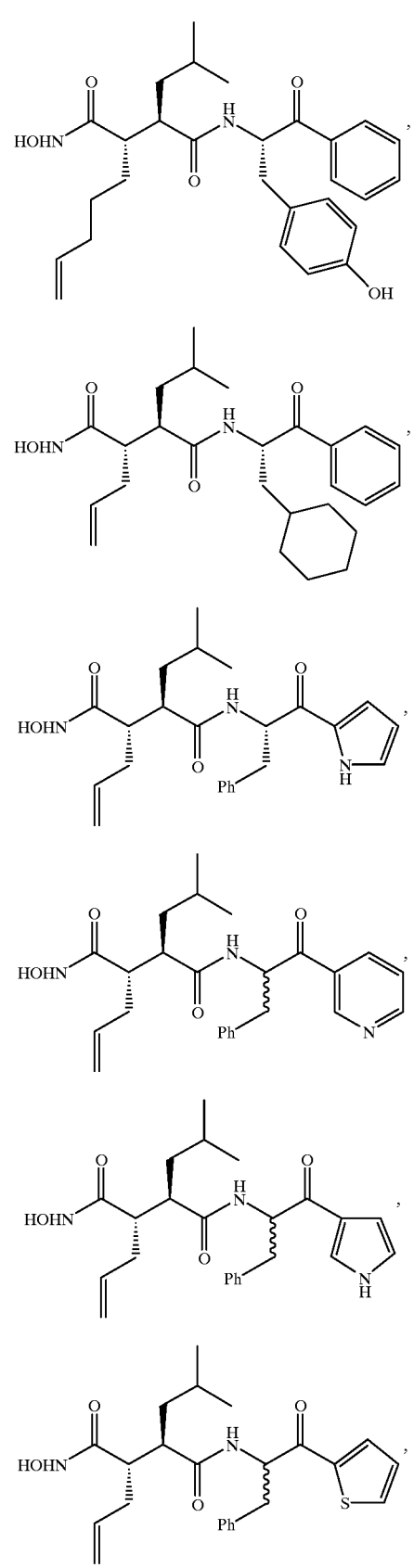

125
-continued
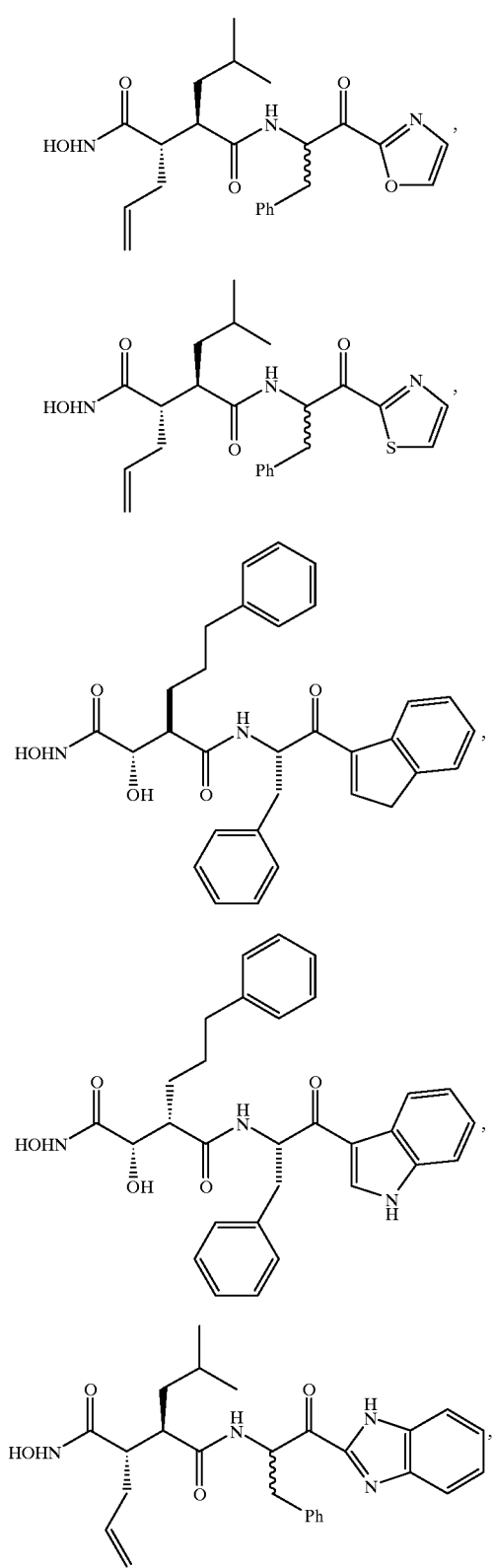
126
-continued
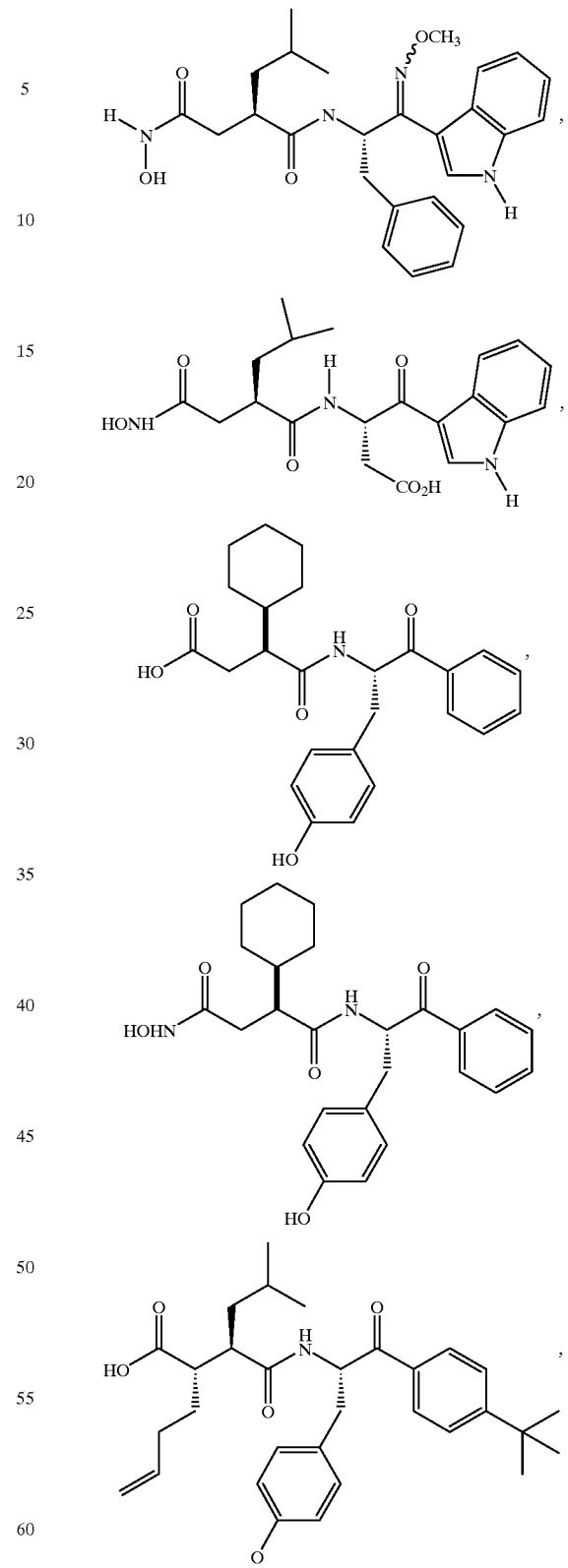

127
-continued
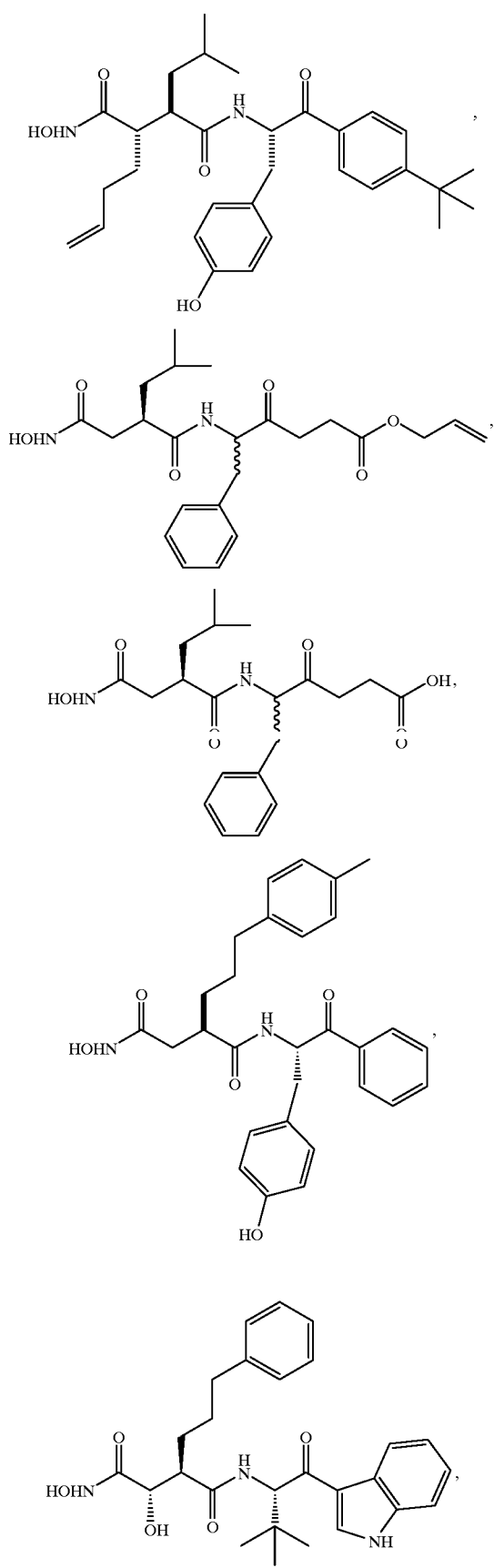
128
-continued
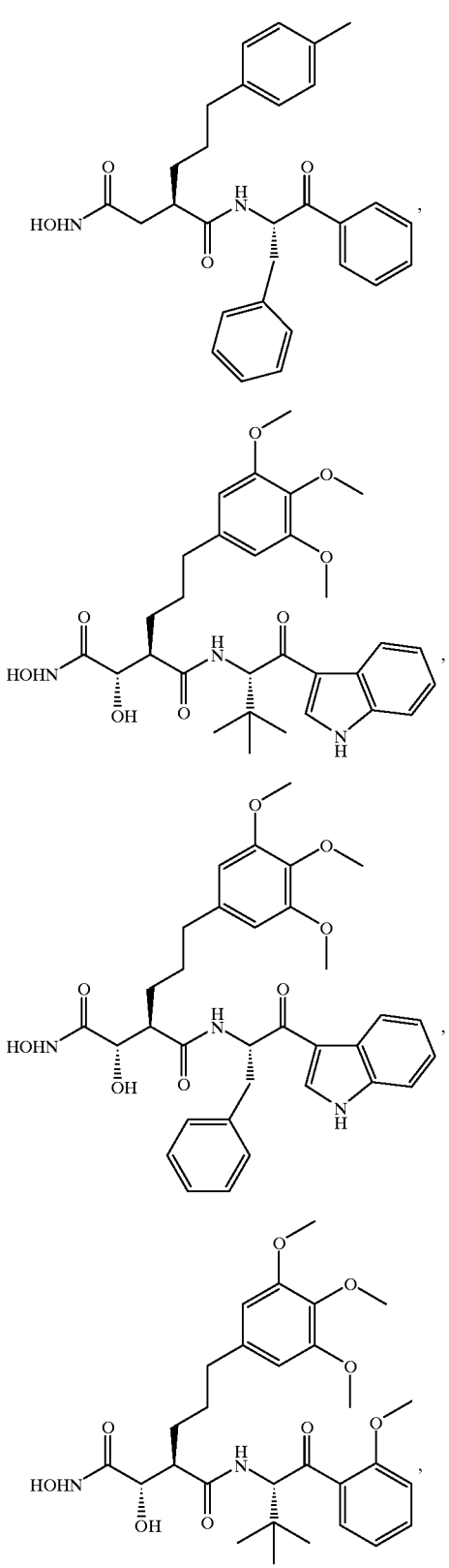

129
-continued
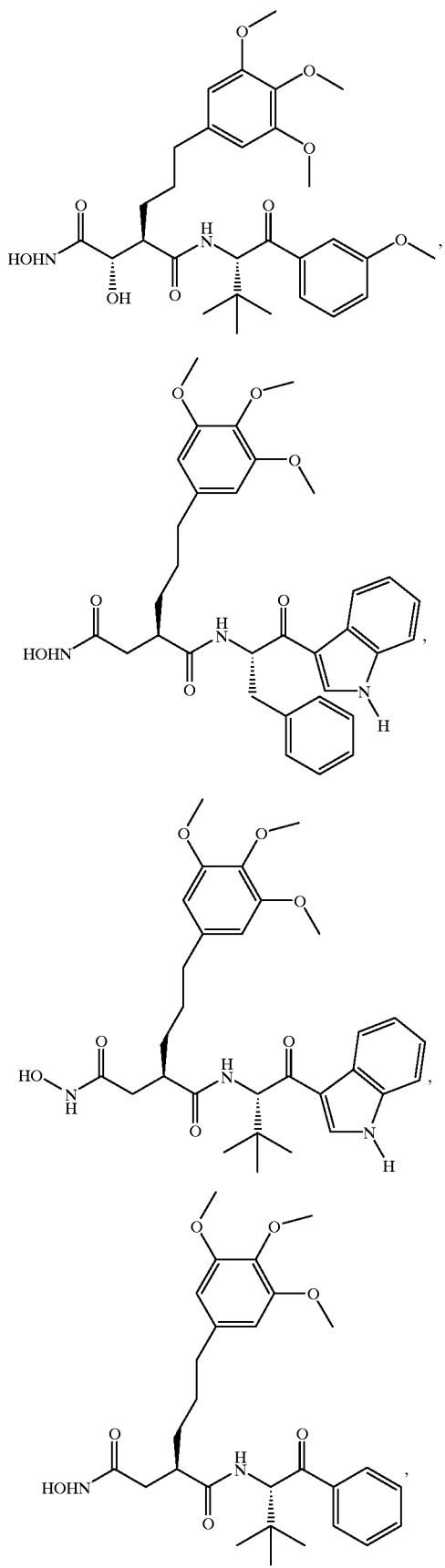
130
-continued
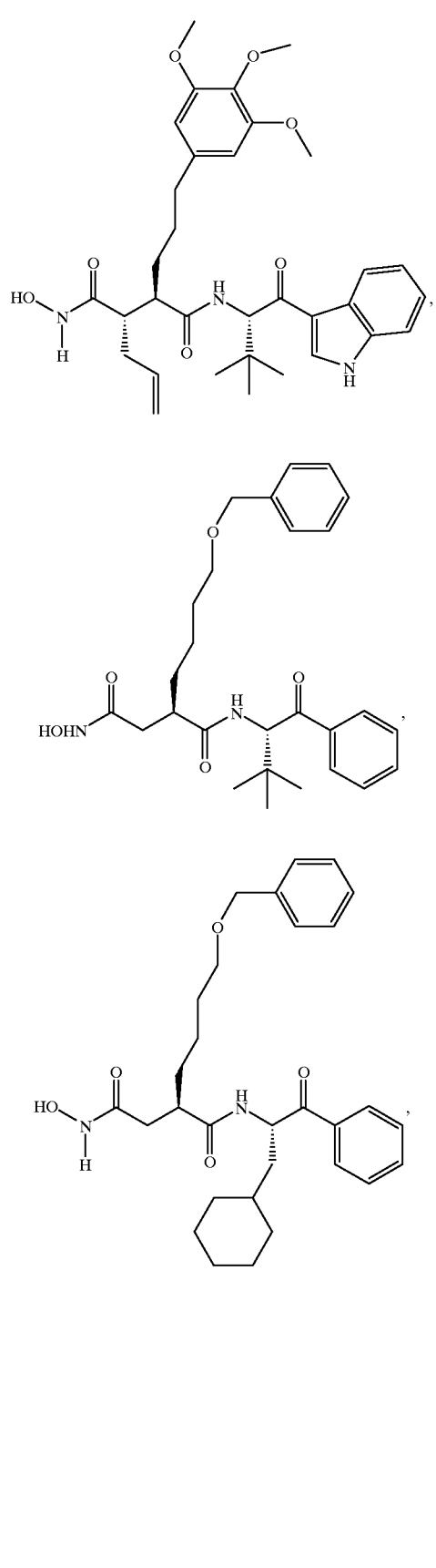

131
-continued

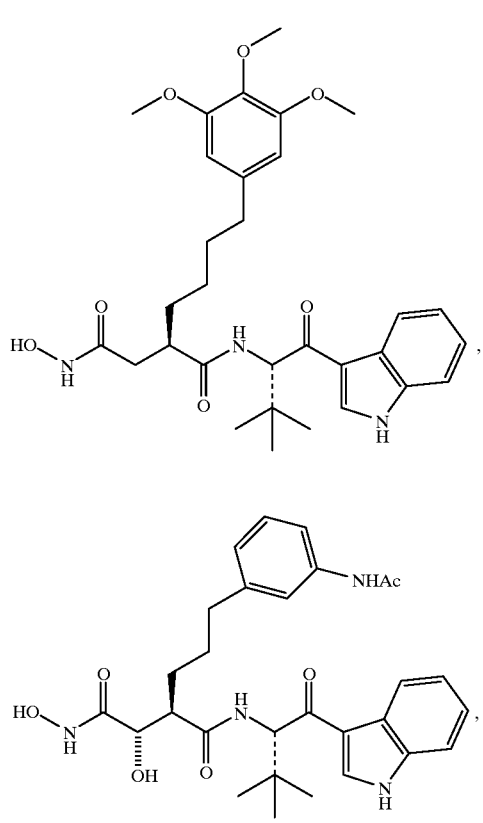

132
-continued

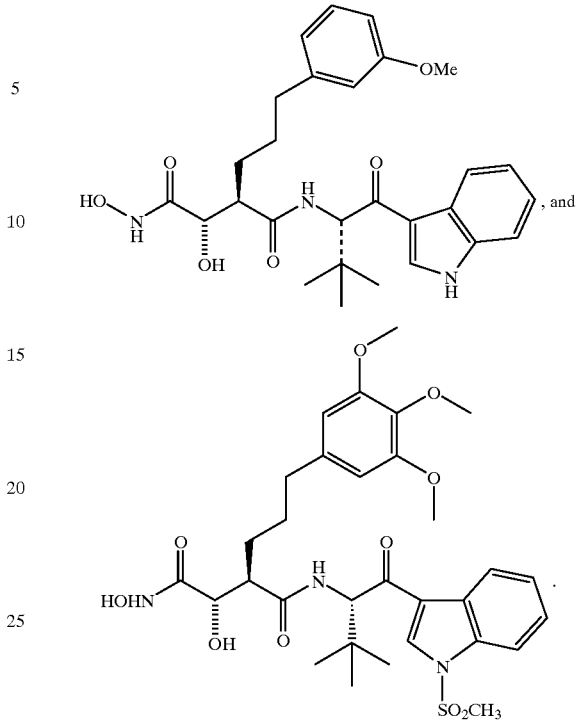

12. A method for inhibiting matrix metalloproteinases in a mammal in need of such treatment, comprising administering to the mammal a therapeutically effective amount of a compound of claim 1.

13. A composition for inhibiting matrix metalloproteinase comprises a pharmaceutical carrier and a therapeutically effective amount of a compound of claim 1.

* * * * *

UNITED STATES PATENT AND TRADEMARK OFFICE
CERTIFICATE OF CORRECTION

PATENT NO. : 5,985,911
DATED : November 16, 1999
INVENTOR(S) : Steven K. Davidson et al.

Page 1 of 3

It is certified that error appears in the above-indentified patent and that said Letters Patent is hereby corrected as shown below:

Col. 108, line 6
replace "
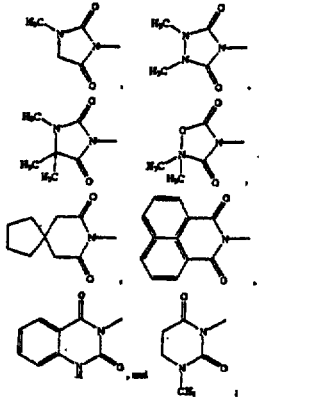
"

with --
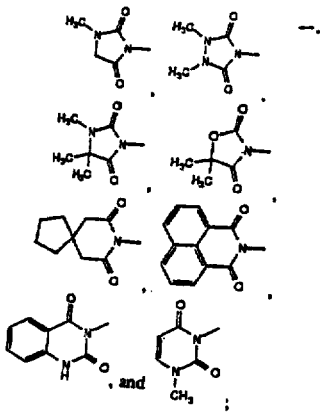
--.

UNITED STATES PATENT AND TRADEMARK OFFICE
CERTIFICATE OF CORRECTION

PATENT NO. : 5,985,911
DATED : November 16, 1999
INVENTOR(S) : Steven K. Davidson et al.

It is certified that error appears in the above-indentified patent and that said Letters Patent is hereby corrected as shown below:

Col. 109, line 26
replace "alklene"
with --alkylene--.
Col. 112, line 12
replace "define aa 5-"
with --define a 5---.
Col. 114, line 8
replace "define aa 5-"
with -- define a 5---.
Col. 125, line 22
replace " 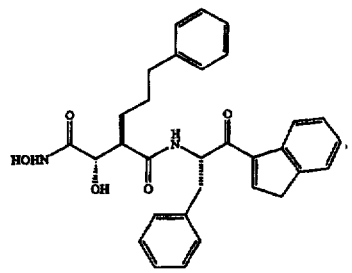 "

with -- 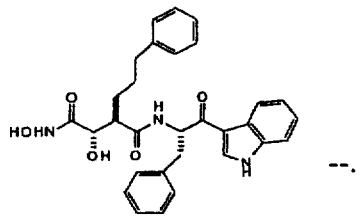 --.

UNITED STATES PATENT AND TRADEMARK OFFICE
CERTIFICATE OF CORRECTION

PATENT NO. : 5,985,911
DATED : November 16, 1999
INVENTOR(S) : Steven K. Davidson et al.

It is certified that error appears in the above-indentified patent and that said Letters Patent is hereby corrected as shown below:

Col. 132, line 35
replace "metalloproteinase"
with --metalloproteinases--.
Col. 132, line 36
replace "comprises"
with --comprising--.

Signed and Sealed this

Tenth Day of April, 2001

Attest:

NICHOLAS P. GODICI

Attesting Officer        Acting Director of the United States Patent and Trademark Office